(12) United States Patent
Luke et al.

(10) Patent No.: US 11,975,066 B2
(45) Date of Patent: May 7, 2024

(54) UNGULATE-DERIVED POLYCLONAL IMMUNOGLOBULIN SPECIFIC FOR CORONAVIRUS PROTEIN AND USES THEREOF

(71) Applicant: SAB Biotherapeutics, Inc., Sioux Falls, SD (US)

(72) Inventors: Tom Luke, Sioux Falls, SD (US); Christoph L. Bausch, Sioux Falls, SD (US); Eddie J. Sullivan, Sioux Falls, SD (US); Hua Wu, Sioux Falls, SD (US); Kristi A. Egland, Sioux Falls, SD (US)

(73) Assignee: SAB Biotherapeutics, Inc., Sioux Falls, SD (US)

( * ) Notice: Subject to any disclaimer, the term of this patent is extended or adjusted under 35 U.S.C. 154(b) by 0 days.

(21) Appl. No.: 17/364,278

(22) Filed: Jun. 30, 2021

(65) Prior Publication Data

US 2022/0062405 A1    Mar. 3, 2022

Related U.S. Application Data

(60) Provisional application No. 63/180,935, filed on Apr. 28, 2021, provisional application No. 63/144,784, filed on Feb. 2, 2021, provisional application No. 63/076,121, filed on Sep. 9, 2020, provisional application No. 63/072,683, filed on Aug. 31, 2020.

(51) Int. Cl.
*A61K 39/215* (2006.01)
*A61K 39/39* (2006.01)
*A61K 45/06* (2006.01)

(52) U.S. Cl.
CPC ............ *A61K 39/215* (2013.01); *A61K 39/39* (2013.01); *A61K 45/06* (2013.01)

(58) Field of Classification Search
CPC ...... A61K 39/215; A61K 39/39; A61K 45/06; A61K 2039/505; A61K 2039/53; A61K 2039/545; A61K 2039/55566; A61K 2039/55577; A61K 39/12; C07K 16/10; C07K 2317/10; C07K 2317/14; C07K 2317/21; C07K 2317/41; C07K 2317/732; C07K 2317/734; C07K 2317/76; C12N 2770/20034
See application file for complete search history.

(56) References Cited

U.S. PATENT DOCUMENTS

| | | | |
|---|---|---|---|
| 7,074,983 B2 | 7/2006 | Robl et al. | |
| 7,253,334 B2 | 8/2007 | Collas et al. | |
| 7,429,690 B2 | 9/2008 | Robl et al. | |
| 7,491,867 B2 | 2/2009 | Robl et al. | |
| 7,652,192 B2 | 1/2010 | Forsberg et al. | |
| 7,803,981 B2 | 9/2010 | Robl et al. | |
| 7,807,863 B2 | 10/2010 | Robl et al. | |
| 7,928,285 B2 | 4/2011 | Robl et al. | |
| 9,315,824 B2 | 4/2016 | Kuroiwa et al. | |
| 9,775,332 B2 | 10/2017 | Kuroiwa et al. | |
| 9,902,970 B2 | 2/2018 | Kuroiwa et al. | |
| 10,822,379 B1 * | 11/2020 | Dimitrov | C07K 14/165 |
| 11,072,649 B2 | 7/2021 | Hooper et al. | |
| 2002/0199213 A1 | 12/2002 | Tomizuka et al. | |
| 2015/0346208 A1 | 12/2015 | Couto et al. | |
| 2017/0233459 A1 * | 8/2017 | Hooper, W | A61K 39/12 800/6 |
| 2017/0253661 A1 | 9/2017 | Malik et al. | |
| 2018/0009902 A1 | 1/2018 | Stavenhagen et al. | |

FOREIGN PATENT DOCUMENTS

| | | | |
|---|---|---|---|
| WO | WO-2004/061104 A2 | 7/2004 | |
| WO | WO-2004/061104 A3 | 7/2004 | |
| WO | WO-2015/036004 A1 | 3/2015 | |
| WO | WO-2019/222796 A1 | 11/2019 | |
| WO | WO-2021236980 A1 * | 11/2021 | |

OTHER PUBLICATIONS

Luke T, Wu H, Zhao J, Channappanavar R, Coleman CM, Jiao JA, Matsushita H, Liu Y, Postnikova EN, Ork BL, Glenn G, Flyer D, Defang G, Raviprakash K, Kochel T, et. al. Human polyclonal immunoglobulin G from transchromosomic bovines inhibits MERS-CoV in vivo. Sci Transl Med. Feb. 17, 2016;8(326):326ra21. (Year: 2016).*

Kuroiwa Y, Kasinathan P, Sathiyaseelan T, Jiao JA, Matsushita H, Sathiyaseelan J, Wu H, Mellquist J, Hammitt M, Koster J, Kamoda S, Tachibana K, Ishida I, Robl JM. Antigen-specific human polyclonal antibodies from hyperimmunized cattle. Nat Biotechnol. Feb. 2009;27(2):173-81. Epub Jan. 18, 2009. (Year: 2009).*

SAb Biotherapeutics, Inc. ClinicalTrials.gov. NCT04469179: Safety, Tolerability, and Pharmacokinetics of SAB-185 in Ambulatory Participants With COVID-19. Jul. 13, 2020. (Year: 2020).*

Liu Z, Wu H, Egland KA, Gilliland TC, Dunn MD, Luke TC, Sullivan EJ, Klimstra WB, Bausch CL, Whelan SPJ. Human immunoglobulin from transchromosomic bovines hyperimmunized with SARS-CoV-2 spike antigen efficiently neutralizes viral variants. Hum Vaccin Immunother. Jul. 6, 2021:1-10. Epub ahead of print. (Year: 2021).*

Sheikhshahrokh A, Ranjbar R, Saeidi E, Safarpoor Dehkordi F, Heiat M, Ghasemi-Dehkordi P, Goodarzi H. Frontier Therapeutics and Vaccine Strategies for SARS-CoV-2 (COVID-19): A Review. Iran J Public Health. Apr. 2020;49(Suppl 1):18-29. (Year: 2020).*

Mitch L. This cow's antibodies could be the newest weapon against COVID-19. Science. (Jun. 5, 2020). 10.1126/science.abd1902. (Year: 2020).*

SAB Biotherapeutics. "SAB Biotherapeutics Confirms Neutralizing Antibodies to SARS-CoV-2 and Begins Clinical Manufacturing of Novel COVID-19 Therapeutic Candidate." May 28, 2020. https://www.sabbiotherapeutics.com/ (Year: 2020).*

(Continued)

*Primary Examiner* — Rachel B Gill
(74) *Attorney, Agent, or Firm* — DLA PIPER LLP (US)

(57) ABSTRACT

Provided are human polyclonal immunoglobulin products for use in treating or preventing coronavirus disease. Further provided are methods for making such compositions in a transgenic ungulate, e.g. using a transchromosomic bovine (TcB) system.

9 Claims, 24 Drawing Sheets

Specification includes a Sequence Listing.

(56) References Cited

OTHER PUBLICATIONS

Gilliland T, Liu Y, Li R, Dunn M, Cottle E, Terada Y, Ryckman Z, Alcorn M, Vasilatos S, et. al. Protection of human ACE2 transgenic Syrian hamsters from SARS CoV-2 variants by human polyclonal IgG from hyper-immunized transchromosomic bovines. bioRxiv [Preprint]. Jul. 26, 2021:2021.07.26.453840. (Year: 2021).*

SAb Biotherapeutics, Inc. "Safety, Tolerability, and Pharmacokinetics of SAB-185 in Healthy Participants." ClinicalTrials.gov Identifier: NCT04468958. First Posted: Jul. 13, 2020. (Year: 2020).*

"SAB Biotherapeutics Awarded $35.6M From U.S. Department of Defense for COVID-19 and Scaling Rapid Response Antibody Program." Aug. 6, 2020. BusinessWire.com. https://www.businesswire.com/news/home/20200806005558/en/SAB-Biotherapeutics-Awarded-35.6M-U.S.-Department-Defense. (Year: 2020).*

"SAB Biotherapeutics Advances Therapeutic for COVID-19 in Partnership with Department of Defense and BARDA." Apr. 16, 2020. BusinessWire.com. https://www.businesswire.com/news/home/20200416005729/en/SAB-Biotherapeutics-Advances-Therapeutic-COVID-19-Partnership-Department (Year: 2020).*

"SAB Biotherapeutics Awarded $27M Contract to Develop Novel Rapid Response Capability for U.S. Department of Defense." Mar. 31, 2020. BusinessWire.com. https://www.businesswire.com/news/home/20200331005569/en/SAB-Biotherapeutics-Awarded-27M-Contract-Develop-Rapid. (Year: 2020).*

"BARDA, Department of Defense, and SAb Biotherapeutics to Partner to Develop a Novel COVID-19 Therapeutic." MedicalCountermeasures.gov. https://www.medicalcountermeasures.gov/newsroom/2020/sab-185/. (Year: 2020).*

"CSL Behring and SAB Biotherapeutics Join Forces to Deliver New Potential COVID-19 Therapeutic." Apr. 8, 2020. CSL Behring. https://www.cslbehring.com/newsroom/2020/sab-covid-19 (Year: 2020).*

"JPEO-CBRND, BARDA Partner with SAb Biotherapeutics to Develop COVID-19 Therapeutic." Apr. 1, 2020. GlobalBiodefense.com. https://globalbiodefense.com/2020/04/01/jpeo-cbrnd-barda-partner-with-sab-biotherapeutics-to-develop-covid-19-therapeutic/ (Year: 2020).*

Ellis J. "Sioux Falls company launches human trials for COVID-19 treatment." Aug. 11, 2020. Sioux Falls Argus Leader. https://www.argusleader.com/story/news/2020/08/11/sab-biotherapeutics-starts-human-trials-covid-19-treatment/3349162001/ (Year: 2020).*

Borrega R, Nelson DKS, Koval AP, Bond NG, Heinrich ML, Rowland MM, Lathigra R, Bush DJ, Aimukanova I, Phinney WN, Koval SA, Hoffmann AR, et. al. Cross-Reactive Antibodies to SARS-CoV-2 and MERS-CoV in Pre-COVID-19 Blood Samples from Sierra Leoneans. Viruses. Nov. 21, 2021;13(11):2325. (Year: 2021).*

SAb Biotherapeutics, Inc. ClinicalTrials.gov. NCT04518410: ACTIV-2: A Study for Outpatients With COVID-19. Aug. 19, 2020. (Year: 2020).*

Riley TP, Chou HT, Hu R, Bzymek KP, Correia AR, Partin AC, Li D, Gong D, Wang Z, Yu X, Manzanillo P, Garces F. Enhancing the Prefusion Conformational Stability of SARS-CoV-2 Spike Protein Through Structure-Guided Design. Front Immunol. Apr. 22, 2021;12:660198. (Year: 2021).*

Sheridan C. Convalescent serum lines up as first-choice treatment for coronavirus. Nat Biotechnol. Jun. 2020;38(6):655-658. (Year: 2020).*

SAb Biotherapeutics. "SAB Biotherapeutics Confirms Neutralizing Antibodies to SARS-CoV-2 and Begins Clinical Manufacturing of Novel COVID-19 Therapeutic Candidate." Sioux Falls, SD. May 28, 2020. (Year: 2020).*

Kastenhuber ER, Mercadante M, Nilsson-Payant B, Johnson JL, Jaimes JA, Muecksch F, Weisblum Y, Bram Y, Chandar V, Whittaker GR, tenOever BR, Schwartz RE, Cantley L. Coagulation factors directly cleave SARS-CoV-2 spike and enhance viral entry. Elife. Mar. 23, 2022;11:e77444. Epub Jul. 30, 2021 (Year: 2021).*

Proteintech. "Polyclonal vs. monoclonal antibodies." https://www.ptglab.com/news/blog/polyclonal-vs-monoclonal-antibodies/#:~:text=To%20answer%20different%20research%20needs,one%20epitope%20(Figure%201.). Accessed Feb. 2, 2023 (Year: 2023).*

Addgene. Weinstein A. "Antibodies 101: Polyclonal Antibodies". Retrieved from Addgene on Feb. 2, 2023 from https://blog.addgene.org/antibodies-101-polyclonal-antibodies. (Year: 2023).*

Ullerich M. "SAB Biotherapeutics Announces First Participant Dosed in Phase 1 Clinical Trial of SAB-185 for the Treatment and Prevention of COVID-19." BusinessWire.com, Aug. 11, 2020, https://www.businesswire.com/news/home/20200811005520/en/SAB-Biotherapeutics-Announces-Participant-Dosed-Phase-1 (Year: 2020).*

Tirumalaraju D. "SAB Biotherapeutics begins dosing in Covid-19 trial." https://www.clinicaltrialsarena.com/news/sab-covid-trial-dosing/. Aug. 24, 2020. Accessed Aug. 14, 2023. (Year: 2020).*

Ullerich M. "SAB Biotherapeutics Announces First Patient Dosed in Phase 1b Clinical Trial of SAB-185 for the Treatment of COVID-19." https://www.sab.bio/2020/08/21/sab-biotherapeutics-announces-first-patient-dosed-in-phase-1b-clinical-trial-of-sab-185-for-the-treatment-of-covid-19/. Aug. 21, 2020. (Year: 2020).*

Ullerich M. "SAB Biotherapeutics Confirms Neutralizing Antibodies to SARS-CoV-2 and Begins Clinical . . . " https://www.sab.bio/2020/05/28/sab-biotherapeutics-confirms-neutralizing-antibodies-to-sars-cov-2-and-begins-clinical-manufacturing-of-novel-covid-19-therapeutic-candidate/. May 28, 2020. (Year: 2020).*

Palca J. "Cows Help With COVID-19 Treatment, No Bull." https://www.sab.bio/2020/06/17/cows-help-with-covid-19-treatment-no-bull/. Jun. 17, 2020. Accessed Aug. 14, 2023. (Year: 2020).*

Leslie M. "This Cow's Antibodies could be the newest weapon against COVID-19." https://www.sab.bio/2020/06/05/this-cows-antibodies-could-be-the-newest-weapon-against-covid-19/ Jun. 5, 2020. Accessed Aug. 14, 2023. (Year: 2020).*

Greenwood, J; host. "Herd" Immunity. I Am Bio. Podcast. Guest: SAB Biotherapeutics, Inc. President & CEO, Eddie J. Sullivan. https://iambio.simplecast.com/episodes/herd-immunity-erRBMwDW. Aired May 7, 2020. Accessed Aug. 14, 2023. (Year: 2020).*

Laguipo, ABB. "Human trials to commence using SARS-CoV-2 antibodies from cow's blood." https://www.news-medical.net/news/20200619/Human-trials-to-commence-using-SARS-CoV-2-antibodies-from-cows-blood.aspx. Jun. 19, 2020. Accessed Aug. 14, 2023. (Year: 2020).*

Kulkus E. "Upstate begins COVID-19 antibody clinical trial." https://www.upstate.edu/news/articles/2020/2020-08-20-kptrial.php. Aug. 20, 2020. Accessed Aug. 14, 2023. (Year: 2020).*

Mackenzie RJ. "Cow-derived COVID-19 Candidate Treatment Produces Four Times More Neutralizing Antibody, Suggests Data." https://www.technologynetworks.com/neuroscience/news/cow-derived-covid-19-candidate-treatment-produces-four-times-more-neutralizing-antibody-suggests-336015. Jun. 11, 2020. (Year: 2020).*

Cohen E. "Human trials expected to start next month for Covid-19 treatment derived from cows' blood." https://www.cnn.com/2020/06/16/health/cow-blood-coronavirus-treatment/index.html. Jun. 16, 2020. Accessed Aug. 14, 2023. (Year: 2020).*

Yang L, Liu W, Yu X, Wu M, Reichert JM, Ho M. COVID-19 antibody therapeutics tracker: a global online database of antibody therapeutics for the prevention and treatment of COVID-19. Antib Ther. Jul. 2020;3(3):205-212. Epub Aug. 19, 2020. (Year: 2020).*

Ellis J. "Manufacturing under way in Sioux Falls for potential COVID-19 therapeutic." https://www.argusleader.com/story/news/business-journal/2020/05/29/manufacturing-under-way-sioux-falls-potential-covid-19-therapeutic/5286860002/. May 29, 2020. Accessed Aug. 14, 2023. (Year: 2020).*

Mulder JT. "How Syracuse researchers are using cows to fight coronavirus." https://www.syracuse.com/coronavirus/2020/08/how-syracuse-researchers-are-using-cows-to-fight-coronavirus.html. Aug. 25, 2020. Accessed Aug. 14, 2023. (Year: 2020).*

Wong S. "Behind SAB's Rapid Response to COVID-19." Apr. 24, 2020. https://www.sab.bio/2020/04/24/behind-sabs-rapid-response-to-covid-19/. Accessed Aug. 14, 2023. (Year: 2020).*

Mitra P. Inhibiting fusion with cellular membrane system: therapeutic options to prevent severe acute respiratory syndrome coronavirus-2 infection. Am J Physiol Cell Physiol. Sep. 1, 2020;319(3):C500-C509. Epub Jul. 20, 2020. (Year: 2020).*

(56) References Cited

OTHER PUBLICATIONS

Saha RP, Sharma AR, Singh MK, Samanta S, Bhakta S, Mandal S, Bhattacharya M, Lee SS, Chakraborty C. Repurposing Drugs, Ongoing Vaccine, and New Therapeutic Development Initiatives Against COVID-19. Front Pharmacol. Aug. 19, 2020;11:1258. (Year: 2020).*
Brown L. "Human trials to start on coronavirus drug derived from cow blood." https://www.foxnews.com/health/human-trials-to-start-on-coronavirus-drug-derived-from-cow-blood. Jun. 18, 2020. Accessed Aug. 14, 2023. (Year: 2020).*
Cohen E. CNN.com. "Researchers using cows to develop antibody treatment." https://www.cnn.com/videos/health/2020/05/15/cow-antibodies-coronavirus-treatment-cohen-pkg-newday-vpx.cnn. May 15, 2020. Accessed Aug. 14, 2023. (Year: 2020).*
Sheridan C. "Convalescent Serum Lines up as First-Choice Treatment for Coronavirus." https://www.sab.bio/2020/05/01/convalescent-serum-lines-up-as-first-choice-treatment-for-coronavirus/. May 1, 2020. Accessed Aug. 14, 2023. (Year: 2020).*
Schwan J. "Jodi's Journal: The Little Biotech Company That Could Beat COVID-19." https://www.sab.bio/2020/04/26/jodis-journal-the-little-biotech-company-that-could-beat-covid-19/. Apr. 26, 2020. Accessed Aug. 14, 2023. (Year: 2020).*
Pfankuch B. "Sioux Falls Biotech Firm Rushing to Develop Coronavirus Treatment." https://www.sab.bio/2020/03/12/sioux-falls-biotech-firm-rushing-to-develop-coronavirus-treatment/. Mar. 12, 2020. Accessed Aug. 14, 2023. (Year: 2020).*
Boudousquie, C. et al. (Nov. 2017). "Polyfunctional response by ImmTAC (IMCgp100) redirected $CD8^+$ and $CD4^+T$ cells," Immunology 152:425-438.
ClinicalTrial.gov (Jul. 2020). "A phase 18, randomized, double-blind, placebo-controlled, single ascending dose study of SAB-185 in ambulatory subjects with COVID-19," Identifier NCT04469179, 11 total pages.
ClinicalTrial.gov (Jul. 2020). "A Phase 1, Randomized, Double-Blind, Placebo-Controlled, Single and Multiple Ascending Dose Study of SAB-185 in Healthy Subjects," Identifier NCT04468958, 11 total pages.
Dekkers, G. et al. (Aug. 2017). "Decoding the Human Immunoglobulin G-Glycan Repertoire Reveals a Spectrum of Fc-Receptor- and Complement-Mediated-Effector Activities," Frontiers in Immunology 8:877.
French, M. (1986). "Serum IgG subclasses in normal adults," Monogr. Allergy 19:100-107.
Golden, J.W. et al. (Oct. 2020). "Human angiotensin-converting enzyme 2 transgenic mice infected with SARS-CoV-2 develop severe and fatal respiratory disease," JCI Insight 5:e142032.
Graham, F.L. et al. (1987). "Manipulation of adenovirus vectors," Chapter 11 in Gene Transfer and Expression Protocols, pp. 109-128, ed. E.J. Murray, The Humana Press, Inc., Clifton, NJ.
Gupta, R.K. et al. (1995). "Adjuvant properties of aluminum and calcium compounds," Chapter 8 in Vaccine Design, Powell & Newman, eds., pp. 229-248.
Hem, S.L. et al. (1995). "Structure and properties of aluminum-containing adjuvants," Chapter 9 in Vaccine Design, Powell & Newman, eds., pp. 249-276.
Hoepel, W. et al. (Jul. 2020). "Anti-SARS-CoV-2 IgG from severely ill COVID-19 patients promotes macrophage hyper-inflammatory responses," bioRxiv, located at https://www.biorxiv.org/content/10.1101/2020.07.13.190140v1.

International Search Report and Written Opinion of the International Searching Authority dated Apr. 26, 2021, for PCT Application No. PCT/US2021/017218, filed on Feb. 9, 2021, 13 pages.
International Search Report and Written Opinion of the International Searching Authority dated Dec. 20, 2021, for PCT Application No. PCT/US2021/039818, filed on Jun. 30, 2021, 12 pages.
Kiyoshi, M. et al. (Jul. 2017). "Glycosylation of IgG-Fc: a molecular perspective," International Immunology 29:311-317.
Kohler, G. et al. (Aug. 1975). "Continuous cultures of fused cells secreting antibody of predefined specificity," Nature 256:495-497.
Korneyeva, M. et al. (Jun. 2002). "Enveloped virus inactivation by caprylate: a robust alternative to solvent-detergent treatment in plasma derived intermediates," Biologicals 30:153-162.
Kuroiwa, Y. et al. (Oct. 2000). "Manipulation of human minichromosomes to carry greater than megabase-sized chromosome inserts," Nature Biotechnology 18:1086-1090.
Kuroiwa, Y. et al. (Sep. 2002). "Cloned transchromosomic calves producing human immunoglobulin," Nature Biotechnology 20:889-894.
Leslie, M. (Jun. 2020). "This cow's antibodies could be the newest weapon against COVID-19," Science, located at https://www.science.org/content/article/cow-s-antibodies-could-be-newest-weapon-against-covid-19.
Lv, H. et al. (Jun. 2020). "Cross-reactive Antibody Response between SARS-CoV-2 and SARS-CoV Infections," Cell Reports 31:107725.
Matsushita, H. et al. (Jun. 2015). "Species-Specific Chromosome Engineering Greatly Improves Fully Human Polyclonal Antibody Production Profile in Cattle," PLoS One 10:e0130699.
Matsushita, H. et al. (Mar. 2014). "Triple immunoglobulin gene knockout transchromosomic cattle: bovine lambda cluster deletion and its effect on fully human polyclonal antibody production," PloS one 9:e90383.
Natsume, A. et al. (Sep. 2009). "Improving effector functions of antibodies for cancer treatment: Enhancing ADCC and CDC," Drug Design, Development and Therapy 3:7-16.
Ramaswamy, M. et al. (Apr. 2011). "Specific elimination of effector memory $CD4^+T$ cells due to enhanced Fas signaling complex formation and association with lipid raft microdomains," Cell Death and Differentiation 18:712-720.
Sano, A. et al. (Oct. 2013). "Physiological level production of antigen-specific human immunoglobulin in cloned transchromosomic cattle," PloS One 8:e78119.
Trejo, S.R. et al. (Apr. 2003). "Evaluation of virus and prion reduction in a new intravenous immunoglobulin manufacturing process," Vox Sang. 84:176-187.
Wrapp, D. et al. (Mar. 2020). "Cryo-EM structure of the 2019-nCoV spike in the prefusion conformation," Science 367:1260-1263.
Wu, F. et al. (2020). "A new coronavirus associated with human respiratory disease in China," Nature 579:265-269.
Yazawa, S. et al. (Apr. 1986). "α-L-Fucosidase from aspergillus niger: Demonstration of a novel α-L-(1->6)-fucosidase acting on glycopeptides," Biochem. Biophysics Res. Commun. 136:563-569.
Edwards et al, "The Remarkable Flexibility of the Human Antibody Repertoire; Isolation of Over One Thousand Different Antibodies to a Single Protein, BLyS", J. Mol. Biol., vol. 334, pp. 103-118, (2003).

* cited by examiner

| IL-2 CD64 inhibition | SAB 301 | IVIG |
|---|---|---|
| EC50 µg/ml | 658.3 | 1085.7 |

SEQUENCE LISTING

<160> NUMBER OF SEQ ID NOS: 18

<210> SEQ ID NO 1
<211> LENGTH: 6802
<212> TYPE: DNA
<213> ORGANISM: Homo sapiens

<400> SEQUENCE: 1

```
cagcagggtc acaagggcag gccgggtcct tgtggagagc acatttagtg ggagggacat      60
gatttccctt caaagtgccc attctggacg cttcccgttc catgctggac gcttcctctt     120
ccacgctgga tgcttcctgt tccacactgg atgcttcctg ttccacgctg gatgtttcct     180
gttacactct ggatgcttcc tgttccacac tggatgcttc ctgttccatc ctggatgctt     240
cctgttccat gctggacatt tcctgttcca ctctggatgc tccctgttcc atgctggatg     300
cttcctgttc catgctggat gcttcctgtt ccatgctgga catttcctgt tccactctgc     360
atgcttcctg ttccactctg gatgcttcct gttccatggt ggacgtttcc tgttccactc     420
tgcatgcttc ctgttccatg ctggatgctt ccttttccat tctggatgct tcctgttcca     480
tgttggatgt tcttgttcc actctggatg cttcctattc cattctggat gcttcctgtt     540
ccatgctgga catttcctgt tccatgctgg atgctttctg ttacatcctg gatgcttcct     600
gttccatgct ggatgttttt tgtttgactc tggatgcttc cagttccatt ctggatgctt     660
cctgttccat gctggatgct tccttttcca ttccgcacaa ttcctattcc attctggaca     720
cttcctgtgc gacacctcct tgggttttct gtctgcccag tccctctatc ctcatcccgt     780
tccctgctac ctcccacctc cacaatcgtc cttgcccagc tcctccctct ctctagagct     840
tcggcctggc aaggtccctc ctgatctcag tccaggctcc cccagcacag gtaggagcct     900
agcacctgcc cttggacctc cccaccctgc atggtgccag catccccgg tccccaggga     960 ggccccattt ctctctctgc ttgtagtcca gtggccctgg agtcccactg caactcgggt    1020
gtgcccctga cctctgagga agttaagtgt cctgtcccta gccaggctat cccgtctgct    1080
cagccccagg gccctgcccc caacccttc ccctcacctg caccacaggc tctggccaac    1140
tctgcccagg ccctgaatgg gccctctgg ctcccctctg ctgctacact gccctgcacc    1200
acctccactc agcttcagtg tgttcatcca cctgtcccaa gtcccctcgg cccccaggag    1260
cacagctggt ggccctggct cctggcagcc catcttgttc cttctggagc accagcctca    1320
gaggccttcc tgtgcagggt ccacttggcc agccctggga ccctcctggt ctcaagcaca    1380
```

```
cacgttctcc ctgcagccag acctgccoct gcctgtgagc tcagccctga gccttggaat    1440
gccttcccat ctccatccca gctcgccttt gccagctgct cagcaggatg aactcacact    1500
cccctccctg caccatgagt cagagccagc tggagacacg cccaggccaa agcagccacc    1560
agggcctagt gggggccaga agcttcagat gagaggccca ggtattgaga ggctgagatc    1620
acgggcagaa tggtcataat cgctgccagt atcagtccag ccccagggac tcagagacag    1680
agaaaagagc agcacacaag gtctgggctc cccaccttct cccgtgagta cgggggagta    1740
tgggggcagc caccaccccc atccccacac acccatgagg cagcctcggc tgtgtctgga    1800
ctcccctcg ccctctgacc cagaaaccac cagaagaaaa gggaacttca ggaagtaagt     1860
ggtgccgccg gtttcaatcc tgttcttagt ctttgcagcg tggagttcac acacctgggg    1920
acctgggggc cgagctgtga tttcctagga agacaaatag cggctgacgg caggggcggg    1980
gctgcccaca tgtacctcgc cagaacagga agggctgaga ccccacctc ggtgagtggg     2040
gtcagcacag gcaggggca caggctcggg aggaggacag agcctggggg cagccgtggg     2100
cgctcctgga cctgagatgc tgaacaggct ccaagaggct ggggagacat ggggtcgagg    2160
ccggccccac atggaggccc aagcggagcc agcacggggg aggtgggcag ccttcaggca    2220
ccgatgccca cccagtgcga gacgacgggg accgtgggca ggggcttcca agccaacagg    2280
gcaggacaca ccagaggctg actgaggcct ccaggacgac cgggctggga gcacgaggaa    2340
catgactgga tgcggcagag ccggccgtgg ggtgatgcca ggatgggcac gaccgacctg    2400
agctcaggag gcagcagagc gagggaggag gagaggcccc aggtgaacgg aggggcttgt    2460
ccaggccggc agcatcaccg gagcccaggg cagggtcagc agtgctggcc gtggggccct    2520
cctctcagcc aggaccaagg acagcaggtg agccgggagc agagcaggga gggtgagtgt    2580
ggcagcagga caggagggtg gaagccaagg agcccagagg cagaggcagg gacaggggag    2640
gcacaggggc tgggctcaga gccagctgat ggggttgggg cacctgctgg cggggagcag    2700
ggctgtggtc agcagtggag aggaggggag agctgtgctg agtgcacggg cgggagaagg    2760
gaagagtcca gggaggccca gaaaggccca gagtgcagca ggcctggggc gaggggaagg    2820
gctgaggctc cgtgcgttca gggaactgac ccagcagagc agaggccact gaggagctga    2880
ggttccagag aggcttccag agcaggagca gtgcagggac aggaggatcc gggagctcat    2940
tcaggagggg cacatgggca agggcaaggg gctctgttgg ggagacctga ctggacactg    3000
gggctgctcc acagcatagg gaacacgcca agtgctgcaa aatcaaaaat gagggcagaa    3060
aaacagccca aacctggaca gagggtgcca ggacaggcag gggggcaaca gtgacctgag    3120
tgacattgct gcccgggttg agggagggca gagtgagcag ggagcaggca ttggagctca    3180
gggaccagga ccaagcagcc acaggtgagc agggcaggtg ggggcagaag gagcagggga    3240
cacctcctgg agctcagggg accagggcag agcagcctca ggtgagcagg ggctggtggg    3300
cggcaggatg agcagggga agaccctgga gctcagggga ccagggcaga gcatcagaag    3360
gtgagcatgg ctagtgggag atgggcaagc agggggcagc ccctggagct caggggacca    3420
ggacagagca tcaggaggtg agcatggcta gtgggaggtg ggcgagcagg ggcagccccc    3480
tggaactcag ggaccaggg cagagcagcc gcaggtgagc acgggctggt gggaggcggg     3540
aggaacaggg ggcagctcct ggacttcagg ggaccaggga gggcatctga aggtgaacag    3600
gggccagtgg ggggcaggat gagcaggggg aagctcctgg agctcaggga gccaaggcag    3660
agcagccgca ggtcagcagg ggcaggtggg aagcatgggg agcaggtggg cagcccctgg    3720
agctcagaga gccagggcag atcatccaca ggagagcagg ggctggtagg aagcaggagg    3780
```

-continued

```
agcaagtggg cagcttttgg agctcagagc accagggcag aagagcctca ggtgagaagg    3840
ggcaggtggg aggcagaata agcagggac agccctgga cctcaggaga ccagggcaga      3900
gcatcacaac gtcagcatgg ctggtgggag gtgggcgagc aggggcagc ccctggacct     3960
cagagagcca gggcagatct gcaggtgagc aggggcaggt ggggaggcagg aagagcagga   4020
ggcagctcct ggagctcagg ggatcagggc agagcagcca caggtgagca ggggcaggta    4080
ggaagcagaa agatcagggg tcagcccctg gagctcaggg gacaagggga gagcatcaga    4140
aggtgagcag gactgaggct cagcctcagg gagccagggc agagcagctg caggtgagca    4200
gggccggtgg gaagcaggag gagcaggtgg gcagcccctg gagctcagag agccagggaa    4260
gatcatccgc aggtgagcag gggctggtgg gaagcaggag gagcaagggg cagctcctgg    4320
agctcagggg accagggcag agcagtcgca ggtgaacagg ggcaggtggg gggcaggagg    4380
agcaaggagc agctcctgga gctcagggga ccagggcaga gcagtcgcag gtgaacaggg    4440
gcaggaggag caaggggcag ctcctggagc tcaggggacc agggcagagc agccgcaggt    4500
gagcaggtgc aggtgggggg caggaggagc aggggcagc tcctggagct cagggggacca   4560
gggcagagca gccgcaggtg agcaggggca ggtggggtgc aggaggagca ggggcaggc    4620
actggagctc aggggaccag ggcagagcag tcgcaggtga acaggggcag gtgggggca    4680
ggagtagcaa ggggcagctc ctggagctca ggggaccagg gcagagcagt cgcaggtgaa   4740
caggggcagg tggggggcag gaggagcagg ggcagctcc tggagctcag ggaccaggg    4800
cagagcagcc gcaggtgagc aggtgcaggt ggggggcagg aggagcaggg gtcaggcact   4860
ggagctcagg ggaccagggc agagcagccg caggtgagca ggggcaggtg ggggcagga    4920
ggagcagggg gcaggcactg gagctcaggg gaccagggca gagcagccgc aggtgagcag   4980
gggcaggtgg ggggcaggag gagcaggggg caggcactgg agctcagggg accagggcag   5040
agcagccgca ggtgagcagg ggcaggtggg ggcaggagg agcaggggc aggcactgga     5100
gctcagggga ccagggcaga gcagccgcag gtcagcaggg ccggtgggag gcaggacgag   5160
caggggacag gcactagagc tcagggcaag gcagccacag gtgagcaggg ctggtgggag   5220
gcatcactca gctcctagac tttggcagga gctgggtagt tgctggcaac agacagctga   5280
gggctggtga aagtcagtg cagcctcctg gtgccgggaa gggagtgtga gtccatccca    5340
ctgagcagtt ggcaagggcg agctgggatg gagaaggga ggcgttccag ggctcagggc    5400
tgagctctca ggcaggggca ggtgtggctg caggggaaac gtgtgcttga accaggagg    5460
gtcccacggc tggtcccagc ggaccctggg caggaaggcc tctgaggctg gcgccccaga   5520
aggagcaaga tgggctgcca ggagccaggg ccaccagcac aatgaagctg agtggaggtg   5580
gtgcaggca gtgtagcagc agagggcagc cagaggggcc cattcagggc ctgggcagag   5640
tcagccagag cctgtggtgc aggtgagggg aagggtggt gagcggggcc ctggggctga    5700
gcagagggga tggcctggct gagggcaggg cgcttagcct cctcagaggt caggggcaca   5760
ccccacctgc agtgggactc cagggccact gggccagcgg cagagagaaa tggggcctcc   5820
ctgtggcctg ggggtcctgg caccatgcag ggtggggagg gccaagggca ggtgcaaggc   5880
tcctacctgt gctgggggc ctgggttgag cccagcagga accttgccgg gggaagctct    5940
ggagagaggg aggaggtggg ctggtggccg agaaggccag gccagggctg ggagggtgac   6000
ggtgtggtga ctgagcctcc agaagtaatg caggacactg ggaggcaggg ggcatccagg   6060
cactcagggc cctgacctgg gctgctgcac actgggcta aggggaaagg agggagagg    6120
```

```
ctgaggagga ggctccagga ggctattcca aggcagggg ttccggggcc ctggggctga      6180
agggcgccga cccatgcag tgtctggccc ctctgctgca cagaagaaaa gggccttgga      6240
gggcagaggg caggctatga ccagggccct gggcaagtca ggccaactca ctaggggagg     6300
gccacgctgg ggcggcaggg tcaggggctt caggggggctc gggggaccca cgagaagcca   6360
tctgagaaca gtgtccactg gtcaagccag gcacccataa aaggctggag tggggccaat    6420
gggcatgagc cgtccctgag gtggcaccga tggccagagc tgaggccaag ctagaggccc    6480
tggactgtgc tgactcccgg cagacacaga gcgctgacct ggctgccgag ccccgcctcc    6540
taggctgcag gggtgcctgc agaagggcac cacagggcca ccggtcctgc aagctttctg    6600
gggcaggccg ggcctgacct tggctttggg gcaggggggtg ggctaaggtg acgcaggtgg   6660
cgccagccag gcgcacaccc aatgcccgtg agcccagaca ctggacgctg aacctcgcgg    6720
acagttaaga acccaggggc tctgcgccc tgggcccagc tctgtcccac accgcggtca     6780
catggcacca cctctcttgc ag                                             6802

<210> SEQ ID NO 2
<211> LENGTH: 9483
<212> TYPE: DNA
<213> ORGANISM: Bos taurus

<400> SEQUENCE: 2
gatcaaacac tgtcaaacca acacaagaga gccccagtac cagatgtgag gctcccccca     60
gaccccagtc acagtgcagc ctgtagaggg aacaggccca gtcgggagac caggaccgag    120
aaagtgaccc ctgtcagtca gtccagctac tcagtcatgt ccgactcttt gcaaccccac    180
agactgcagc acgccaggcc tccctgccca tcaccaactc ccggagcttg ctcaaactca    240
agtccattga gtcggcgatg ccatccagcc atctcatcct ctgtcgtccc cttctcctcc    300
tgcccccaat ccctcccagc atcagagtct tttccaatga gtcaactctt cgcatgaggt    360
ggccaaagta ttggagtttc agcttcaacg tcagtcctc caatgaacac ccaggactga     420
tctcctttac aatggactga ttggatctca ttgtagtcca agggattctc aagagtcttt    480
tccaacagca cagttcaaaa gcattgattt tttactcagc tttctttatg gtccaactct    540
cacatccata catgactact ggaaaaacca tagctttgac tagacggacc tttgtcagca    600
aagtaatatc tctgctttct aatgtgctgt ctacgttggt catagctttt cttccaagga    660
acaagtgtct tttaatttca tggctgcagt caccatctgg agtgattttg gagcccaaga    720
aaatagtctg tcactgtttc cattgttttcc tcgtctattt tgccatgaat gccatgatct    780
tcatttttcg aatgttgagt tttaagccag ctttttcact ctcctctttc actttcatca    840
agagtctctc tagttcctct tcattttctg ccatgagagt ggtgtcatct gcatatctga    900
ggttattgct atttctcctg gtaatcttga ttccagcttg tgttcctcc atccaggtat     960 gtcacatgat gtactctgca tagaagttaa ataagcaggg tcacaaaata caatcttgat   1020
gttctccttt tccaaatttt aaccagtccg ttgttcctta tctggttctg ttacttcttg   1080
acctgcatat aggttctcta ggaggcagtt aatgtggtct ggtattcccc tctctttaag   1140
aatgttccag tctgttgtga tccacccatt caaaggcttt agtgtagtca ataaagcaga   1200
agcagtaaaa tgctgccact ttctaggtgg agctcacata tggataccac acccaaacct   1260
tgaccaagcc agaacctcat gacaatcatg tgcagtgcta taaatgatct cagctgttac   1320
acagtcacta tttacaaaat gtggggcaag agagcctgaa catgccatct ggccaatttt   1380
tctctctcct catgggttgt ttagctttt ttcttttttt ttttttttaa ttaagctgta    1440
```

```
tgagttgctt gcacattttg gaagtttatt ctttagtggt cacgtgattt gcaaatatct   1500
tctctaattc tgcaggtagt cttgttttgt tgatggtttt ccatggtgta caaaagcctt   1560
ttagcttaat taggtcccat ttgtttattt ttcttttat  ttctattact ctaggagatg   1620
gatggagaag gaaatggcag cccactccag tgttcttgcc tggagaatcc cagggacggg   1680
ggagcctggt gggctgccgt ctatggggtt gcactgagtc ggacatgact gaagtgatat   1740
agcattagca ttaggagata aatacaaaaa gacaccacct tgatttatgt caaagagtgt   1800
tctgcccatg tttccctctg ttttatagcc tcccatttca cacttttgtc tttaatccat   1860
tttgagttta ttttttgccca tggcactaga gaatttataa tttcatttat taacaggtag   1920
caatccagtt tttccagaac ttattcaaga gactgtcttt tctccatctt acactcttgc   1980
ctcctgggtc atacatgaat tgatcatagg tgggtgggat tgttcctggg ctgtctatcc   2040
tgtctcactg atcactgatc tataattgtg gttttgtgcc agcaccatag tgttttgatg   2100
gccgtagctt tgcagtatgc tctgaagtct gggagcctga tgcctccagc tccacttttg   2160
tttcttgaga ttgctttgac tatttggggt ctttatgtct cccaacaaat tttcaaaagt   2220
tttgttctgg gtctgtggaa attgccattg gtcatttgat aggtgttaca ctgaacctgt   2280
agattgcttt cggtagaagt gtcattggca caatattgat tcttctgatt taagagtatc   2340
ttttctaaat agacatttct ccaaaaaaga catacagatg gctaacaaac acatgaaaag   2400
atgctcaaca tcactcatta tcagagaaat gcaaatcaaa accactatga ggtaccattt   2460
cacaccagtc agaatggctg cgatccaaaa gtctacaagc aataaatgct ggagagggtg   2520
tggagaaaag ggaaccctct tacactgttg gtgggaatgc aaactagtac agccactatg   2580
gagaacagtg tggagattcc ttaaaaaact ggaaatagaa ctgccttatg atccagcaac   2640
cccactgctg ggcatacaca ctgaggaaac cagaagggaa agagacacgt gtaccccaat   2700
gttcatcgca gcactgtttta taatagccaa gacatggaag caacctagat gtccatcagc   2760
agatgaatgg ataagaaagc tgtggtacat atacacaatg gagtattact cagccattaa   2820
aaagaataca tttgaatcag ttctaatgag gtggatgaaa ctggagccta ttatacagag   2880
tgaagtaagc cagaaggaaa acataaaata cagtatacta acgcatatat atggaattta   2940
gaaagatggt aacaataacc cggtgtacga gacagcaaaa gagacactga tgtatagaac   3000
agtcttatgg actctgtggg agaggggagag ggtgggaaga tttgggagaa tggcaatgaa   3060
acatgtaaaa tatcatgtag gaaacgagtt gccagtccag gttcgatgca cgatgctgga   3120
tgcttggggc tggtgcactg ggacggccca gagggatggt atggggaggg aggagggagg   3180
agggttcggg atggggaaca catgtatacc tgtggtggat tcattttgat atttggcaaa   3240
actaatacaa ttatgtaaag tttaaaaata aaataaaatt ggaagaataa aaaaaaaaa    3300 agagtatctt ttcatctgtt tgtgtcacct taatttcttt catcagtgtc ttagagcttt   3360
cagagcagag gaattttgcc tcctagggaa ggtttattcc taggtatttt attctttttg   3420
atgggatggt aagtgggatt cttccttaa  attctcttta tggtatttca ttgctgccat   3480
acagaatgca acagattttt gtgtattaat tttgtatcca taaatttat  ccaattcatt   3540 cctgagctct agggttttct gtaccttctt tagcattttg catgtgttaa atcatgtcac   3600
ctgcaaacag caggtgtttc ttacttggct tctggattcc ctgtgtccct ttctctcccc   3660
tgattcttac acttaggcct tcactgtgct gcactgtggg cccttgctgg ttacctacta   3720
tatacgcagt cgtgtggatg tattagcacc aaactcctaa tttatccctg ggatgtggtg   3780
```

```
ggtcaaccag gcgcagtgca tgaggaagag gaacaccgtg acggctagga ttcccactcc    3840
tccctgggt  gcaagggcgc cgcttaaacc accccaccaa cccacaagac atacctcagt    3900
cacatctgga ctcccccagg ccctctgaga cagaaaacac tcagaagaaa agggaacttc    3960
aggaagcaag tcgcgtcacc aggtttcatt cctgttctta gtcttcacag cactggggga    4020
agggccctca cacctcctgg gactggtgac caagtcccag ggagcagggc tgcagacaca    4080
gaacacaggg aacttcagga ggcagatgga gtcaccaggt ttcattcctg ttcttagtct    4140
tcacagcact gggggaaggg ccctcacgcc tcctgggact ggtgaccaag tcttagggag    4200
cagggctgca gaaacagcac gcagatccca ggagccacat gtgtctgtgg gccagagcag    4260
ggaaggggcc cggagcccca ggctgtgggg cagcccctc  catggccccc accatgggtg    4320
agtggggacc ccgaggatga gcgcacaggg acaggaatga gagccctgga gggagaccgg    4380
cctcgggacg cccagagggg ctggagcagc cgagtgggcc caggggaggc agctgcccct    4440
ggtcacagtg caggacgagc gtgtggacag aacccagaca gggtgcacca caccaagagc    4500
actgctgccc agggctggag agctcagggg gctgtgggcc gtggaggagc aggatgggct    4560
tgggggcggg agggaaggga tgtgcatgac caggggctct ggaggccggg gctgggcagt    4620
catgaggacc agccaggacg gaaagagggt ctgacctgag gacgcaggga agggagagga    4680
ccccagagca gtgaagtctt ctggacaggg cagtggagcc agcgtcggtc ccagggcagg    4740
gccacatgca gggactgtgg gtcccgactg gctgggggcc gagggcagcg gcagacttgg    4800
gggcaaggct gcagggccag ccgggttcta tgtccacagc aggcaccacg gggctgaacc    4860
cacagccccc caggacacag ggggctgacc agagctcagg gcctgaggac cagcagtggg    4920
agccagagag aggcaggtga cccgaaaact ggaggcagca aggggccaga ggagggtgtg    4980
gatggaggga tagagaagag cagagagcaa aggcaggacc tctgccagga ggggcccggg    5040
tggacagagc tcctccaggg gagagttgcc tggaggccag tgggcacctg gcaagtccag    5100
ggatgagagc tgaacccagg aaataaagga gtgaggagtg gagatgggca ggggtgaggg    5160
cttccagagg ggccagaggg gcaagaaagg ctgaggggc  ggcccaagga caggggggcag   5220
caaggctgca ggtgagcagg ggctgggagg gcagggggc  ccctagagat ctggggagc     5280
aggcacagct tgtgggtgaa aaggggttag gagggcaggg ggcccctggt gtttggggga   5340
gcagatagag cttttgtagg tgagcaggga gctgggaggg cggggagag  ggtggcctgg    5400
tgctttgggg agcaggtaca gcctgtgagg gtgagcaggg gctgggaggg caggggtgt     5460
tcctggtgtt tggggtagaa ggcacagctt atgggtgagc aggggctggg agggcagggg    5520
gagccccgg  tgctttgggg gagcaggtac tggttatgag ggtgagcaag ggctgggagg    5580
acgggggag  cccccagtgc tttgggggaa caggtacagg ttatgagggt tgagcagggg    5640
gctgagagta aggaggtgag cctagtgctt tgggggagca tgtacagcct gtgaaggtga    5700
gcaagggcta ggaggacagt gggatccct  ggtgctttag gggagcaggt acagcttgtg    5760
agggtgagca agggactggg aggacaaggg gtgcccctgg tgtttgggg  agcaggtact    5820
agttatgagg gtgagcaggg gctgggagga ctggggagc  ccctagtgct tgggggagc     5880
aggtacaggt tatgagggtg agcaggggct ggaggacag gggtgttcc  tggtgtttgg     5940
ggtagaaggc acagcttatg ggtgagcagg ggctgggagg acagggggc  ccctggagat    6000
atggggaagc aggtacagct tgttggtgag caggggctgg gaggacaggg ggagcccctg    6060
gtgctttggg ggaacaggta caggttatga gggtgagcag ggggctgaga gtaaggaggt    6120
gagcctagtg cttttggggga gcatgtacag cctgtgaagg tgagcaaggg ctaggaggac    6180
```

```
agtgggatcc cctggtgctt tgggggagca ggtacaggtt atgagggtga gcaaggggct    6240
gggaggacaa ggggtgcccc tggtgctttg ggggaacaag tacagcctgt gacggtgagc    6300
agggagctgg gagggcaggg ggtgcctctg gtgctttggg ggagcaggta cagcttgtga    6360
gtgtgagcaa gggctgggag aactgggggt gtccctggta tttggggggag caggtactgg    6420 ttatgagggt gagcaggggc tgggaggact gggggagccc ccagtgcttt ggggggagcag    6480 gtacaagtta tgagggtgag caggggcttt agagtaaggg ggggtgcacc tggtgctttg    6540
gggagcgtta cagcctctga gggtgagcat gggctgggag gacagtggga tccctggtg    6600 ctttggggga gcaggtacag cctgtgaggg tgagcagggg ctgggaggac aggggggagcc    6660 cttggtgttt gggggagcgt gtacagcctg tgagggtgag caggggctgg gaggaaagtg    6720
ggagcccctg gtgtttgggg gagcaggtac agcctgtgag ggtgagcagg ggctgggagg    6780
aaagtgggag cccctggtgt ttgggggagc gtgtacagcc tgtgagggtg agcaggggct    6840
gggaggaaag taggagcccc tggtgtttgg ggagcgtgt acagcctgtg agggtgagca    6900
cgggctggga gggcaggggg agcccctggt gctttggggg agcaggtaca ggttatgagg    6960
gtgagcaagg ggctgggagg gcaggggggag ccctggtgt ttgggggagc atgtacagcc    7020
tgtgagggtg agcaggggct gggagggcag ggggcgcccc tggtgttttg gggagcggta    7080
cagcttgaga gggtgaacag gggctgggag gacaggggga gccctgatg ctttggggga    7140 gcaggtacag cttgtgagtg tgagcaaggg ctgggaaaac tgggggtgtc cctggtgttt    7200
gggggagcag gtactggtta tgagggtgag caggggctgg gaggactggg ggagcccgtg    7260
gtgctttggg ggagcaggta caggttatga gggtgagcag gggctgaga gaaagggggg    7320 tgtgcctggt gctttgggga gcattacaat ctgtgagggt gagcaggggc tgggagggca    7380
gggggagccc ctggtgcttt gggagaacag gtacagcctg tgagggtgag caggggctgg    7440
gaggacaggg ggagcccctg gtgtttgggg gagtgtgtac agcctgtgag ggtgagcagg    7500
agctgggagg gcaggggggag cccctggtgc tttgggggag caggtacagg ttatgagggt    7560
gagcaggggc tgggaggact gggggtgtgc ctgatgcttt ggggggagcag gtacagcttg    7620 tgagggtgag caggggccg ggaaagcagg gtgtatctca aaactttag gggatcaggt    7680 agtgcttctg gggatgagca gaggtctggg aggacagggg gtgcccttgg agttggagag    7740
caggtacagt ctgtgaggtg agtagagggc tgggcaggca cagggagccc ctggtgcttt    7800
gggggaacag gtgcaggtcg tgagggtgag caggggctgg gaggacaggg agtgtccctg    7860
gtgtttgggg tagaaggcac agcttatggg tgagcaggggc ctgggaggac aggggagcc    7920 cctgttgctt tgggggagca ggtacagctt gtgagggtga gctgggtctg gaagacagg    7980 gggagcccct ggtgctttgg gggagcaggt acagcttgtg agggtgagct gggtctggga    8040 agacagggg agcccctggt gtttgggaga gcagatacag cctgtgaggg ttagcagggg    8100
ctgggaggac agggggtgcc cttggagttg gagagcaggt acagtctgtg aggtgagtag    8160
agggctgggt gggcagggg agcccctggt gctttggggg aacaggtaaa ggttatgagg    8220
gtgagcaggg ggctgagagt aagggcgtgt gcctgttgct ttggggaagc atgtacagcc    8280
tgtgagggtg agcaggagct gggagggcag ggggagcccc tggtgctttt gggggagcag    8340
gtacagcctg tgagggtatc caggggggctg ggaggacatg gggtgcccct ggagattttt    8400
ggaagcagta atagcttgtg ggtgagcagg aagctgcgag gacaggaggt gcccctgttg    8460
ctttgggtga acaggtacaa cttgggtgag caggggctgg gaggacaggg agtgcccttg    8520
```

```
gagatttggg ggagcaggtg cagcttctgg ggataagcag ggggctggga gttcagggta      8580
ttaggggagc agacaaagat cgcgcagctg agcaggcgct ggaatgtcac gcccctgccg      8640
acgacctcag ttgaccatgt gtgtgctgag cacatcggta cgaaagggtc cgagggtgca      8700
aggggccatt tgtgctgtgg gccagatgca gggacacagg gcagtgtgag ccctgcagag      8760 aagatgggc ccaagagcgc agctgtccag agctgagtcc agagggctga gaccagtggt      8820
gtgggtgctg gacgagggtg aagggctggc gtgagggagc aagggcacag ggctgggaga      8880
gctcaggcca cagctggtga agcagagggc tgagacaagg ggtgtaggcc acccctcaag      8940
acaatggggg tgctgtttgg tggagggtct gcatgaagaa caaagcaagg aggagcgaag      9000
acccgagagg aagggctctg gggctgcagg aaggggcgc cctgagggca ccgggtgggc      9060
tgcacttctg ggccgagggt ctgcctgtcc cagcagcctg tgtggctcag gagccaaagt      9120
ggggccagac ctgggacgct gtgcttgata gggcggtgca aggggccagg agctacaggg      9180
cgcccactgg cagtcagtcg ggctgcaggc ccagggagct gaccaggctg ggggagcagg      9240
ggccatggga agggccaggc gcccacagga gggaaggggc cctgggctct gatccaggag      9300
gccacactca ccgacccaag ctgtgtccag acaccccaac tgcagtacag agagccgggt      9360
ggccaccatg ccggccggtc atcagaccct ggaagcaggt ggtggctggg ctcggaggtg      9420
ccccaggcct gggcacctga ggtcctgctg gaccccgcat tcacccagcc tcctctctca      9480
cag                                                                   9483

<210> SEQ ID NO 3
<211> LENGTH: 10298
<212> TYPE: DNA
<213> ORGANISM: Equus ferus
<220> FEATURE:
<221> NAME/KEY: modified_base
<222> LOCATION: (6918)..(8037)
<223> OTHER INFORMATION: a, c, t, g, unknown or other

<400> SEQUENCE: 3
agatatcccc caagtcatgt cacaatacta ccatgttcaa agtacatgaa tgctttgaaa       60
cagactggtc tcagtggctg ggtgttcctt gggtggctcc taatggaact cagtggttgt      120
gtggaacaaa cctctagtct tggctcctgc ctggatggct gggacactgc accctggact      180
tcctttggag gcagggaagg agtcgccctg agctaacagc tggtctcaat gttcctccca      240
gtaaggccag atggactcca tcagtgttca ctggtatgac caccagcggc tatatttgct      300
gcttccttgg gctacaagat gtcatatcac atagaggctc taactaaatt tactcaaact      360
gccctcaatg aaagtcaggt aggaataccc ttattaaata ctcaaatgtc tttagtgggg      420
agggctgtct ccccatcaga atggccttag atagtctaac agcatcccaa ggtgggacat      480
gtgcactcat tcaaactgaa cgctgcgttt ttagacctga tgagtcttcc aatgtgtcct      540
ctctgctaaa gcacttggaa aagcaggtaa atgccttaag cgatcctgca tccaggcttg      600
atttgcgtgg ttggctccct tcaggtgtgg ctgccctctt gaaatctgaa ttgcaattcc      660
tgtgtctgtt actccttgga attcttctat taatcataat atgcaaacta attactcttt      720
cctttactca gtgttgtaag actggcatgc aggctagaat aatggttgct cagccacttg      780
aggtgattga ttgatcttac aaccctggat gaatttcctt ctcataagac tatgcctaag      840
aactcatttt tcaaataatc ctttcaagtt ttgaattatc agcactgtta gtgtagctgt      900
tctataatta ggcacatgca gcatcatgag tcagatcaaa gcataggtac aacgtttgtg      960
tgacaatcta agttactgaa aaacttacat aacctatgga atgcttcccc tgtaattgta     1020
```

```
tacctctatg ctcatccact atatccaact atttcctgcc attgggcata actgagcacg   1080
tcaatgagat aaaagcccag cactgatggc catcatggac cagggcaggc aacaatcacc   1140
atagcaccaa gggacaatat ttagatcatc agtgctttct ataaaaacat tatcgatcaa   1200
aggtgggaaa ataatgaatc aatgaaagca ataagaaaag ttaaaatgtt gaggtatatg   1260
aggaagccat ttggtttaga ctaattaggc ctcatctagt ttttctggaa agtcctgatg   1320
tgcctgtcga atatgcattg tacatctgct gcatttacaa tgtcccaaag caagaatgat   1380
gcccttgaaa ttatcctgcc ccctttttggc atttctttat agatgagcac ttcttcccag   1440
aatgcaagga ttcgttactg acctactgtg tcatcttgtg atcactcacc cgcaatacta   1500
gcaaagcatc ttgtgactgt agtaaaagag atactcctgt catatgtgat gtacgtccct   1560
tgttccaaga cggtatataa ccacgctgca cacccggctt cttcacaaca cttccttcct   1620
tggtgaaggt tattgtcccg ggctatgtag tcctcaaatt ggctcaaata ataaactcac   1680
cccaattttg attaacagat tgattatagt ttattgcctc aacatttcct gaccagaaat   1740
tacatagatg aacgtgcttc ttatgtaacg gcagcgatgc tcacagcctg cggagcacat   1800
gactgaggga ggctgccttc cgtgggagag atggcaaaac tgcgtgggcg ccatggagag   1860
gaggccgggc cagagccgcc gggagtgtgc agtggattat catgaattca tcccggaggg   1920
accagagggc actcccttca ccaaggctgc tgctgacggc gttttctggg tgtccacagc   1980
aacattccca ggaccacagg ctcctccatc acctggtcct gccccatgca gaggttcact   2040
tccctcacca gaccccaggg tacccatgcg actgactcca tggggacagg gccactgagg   2100
gaccactgct gggtctctga gagcaggacc taaggagaca gggctcctcc tgggagtcag   2160
gcccgggcac cactcagcgt gggcaatccc catggaaaga tcacagagac agagggaaca   2220
cgggcgcccg cccagcccag cgccagact ccaggtggag ccttccagcc cctcgctgat   2280
gcgagtggag cagagaggag cgcccccgcc cacagaagcc ggcactgcct gcaggccacc   2340
aacgcagaag caaatcagca gaagagctgc agaggccact ctctgtgggg cggtccacag   2400
cacacccatg aaccgccgga cacgatatgg gaccgcacg tgggcgctgc tctgagaaac   2460
ctcaactcta gaaagtaagc acgaggacca gagagcaggg gaggcagagg gacccagagt   2520
agaccgttgg gggatgtgga gtggctctgg ggacacccga ggccaaaggg tgctgcaaat   2580
agcaacaggt gggagggccg actcccctcg tacatctcag gtcacctcct agaaggttcg   2640
ctttggactt tgctcttggc ccacctaagc ggccacagcg tacgcccctg cccaccaacc   2700
attggaagga gccaggcctg ccttcacgtc cagtcaccta cctggccccc ggcaattcca   2760
gggtggggac catggtgccg cccagggatc cccgatccaa ggcctaacgt gcaagagacg   2820
ggatggccca ggtttgtaca cggggccttg ggtgtgccga ggcactgcaa gtcatgagac   2880
actgagggtc cgtgtccccc cacagacaaa aagctgggtc ctggcccaca cacgggagga   2940
caggaacagc atgctgtctc tcagacagag gagacctttg gccccagtg accaccgtgg   3000 actctgtcct tgtacataga cttctttctg tccccagagg acagctgtgg atgggagaat   3060
atcttccctg ggaccctggg tgctaccacc cttcagtcag agatccagcc atggatggag   3120
ccagagaggg atggagggaa gaggcaggga cccagaggaa gacggctttg tacttagggg   3180
gctggcctgg caggaggaca ggatgaggcc ctgggctgag ctgcgggctg tgagcaggac   3240
agcctgtgtc cacaatggac gctgactagg gcaggggga gtgtcctctg ggctgtgggt   3300
accagagggc tcaggtgaga ggcctgggtg ccctggcctt tggtgggggcc atcgggcata   3360
```

```
atccttgtgg gagggagaga gcaaagagag gcatgtgagc ccggacttcc tgcactctcc    3420
ccagagtcct gggcgccaga ccccctccac tcccacacac ccacgtgtgg cagcctctgc    3480
ctcacgtctg tactccccc ggctctctaa gacagaaacc acccagaaga aagggaact     3540 tcagggagca agcggtgccc ctgctttcag tcccgttctt agtctttgca gggtcgtgga    3600
gagtgggttc ccacctccgg gaaccagcta ccacctccgg gaaccagcta ccaactccta   3660
ggaagcaggg cagagggcaa caagcccggg gccgcgagga gccacatgtg cccgggcca    3720 gagcagggc gtggggggag ctcctcggaa gccctggctt ccaccacctc cacagccccc   3780 accctt ggtg agtgggtcc ccacggagca ggggaaggg agtggagtca gggcagtgga   3840
aacggttgca gagctacggg gagcccaggc acccagggac gactccgagg ggctcaagca   3900
gctgagccag cacggggag ggcaggctgc ccacgagcca cggtgccaac cggacgcagg    3960
caccaggcag ccatgggcag ggcacgccca cgccaacaga gctggacaca ccagaggccc   4020
atgaaagtta accttgagga aattgatgac cttgaggcca gaagcctgag ggctgcattt    4080
ggccagctgt gctgagggca ggaccagcca ggagctgagc tgctgcagca cggacgccag   4140
gatgcacaga tgggtttgag cacagagagg gggctggctc agagcagggg aggaagagga   4200
cctccaggtg gcctaagggt cctgtccacg ccaatgagcc agctcaagcc ccagggcagg   4260
gtcagaggtg gccgccatgg tgtcctaggc tgtagccagg accgagggca gcaggtgagc   4320
caggtgcaga gcccaagggg ccggcggatg cacccatgtg ctcagaactc agactgcaca   4380
gggctgggca ggagctcagt ggctacaggc agacgttggg agccaggcag tgagggtcca   4440
gagcaggtgc tggggttgca gtgttgggag ctggtggca aggggagctg acccagcaat    4500
ggagggagca cagtcccgag gggccttcca gatgggcttc tgagcgccgt gaggggcaca   4560 gagacgtga agcccagctg gccaggagc tcctccagga ggagaccacg gcaggcaggg    4620
gctctgccag gggagagtta gccagagaga gggtgggcat ctggtggctc caggaggcaa   4680
aggccagtga tgggaaagga atgagcccag gatggagggt gaacctgggc tgaggtgct    4740 gggagaggca ggaggggcaa aggcagcccc gggcagaccc agcagcctgg ggctgagctt   4800
agggacctga gctgtgtgga ggggatcgta ggacaggagg gacagagggc tgctgtggac   4860
ctggagttcc agggacaacg ggaagaacag ctacggatga gcaggggaag gtgggagggc   4920
acaaaaggac aggagcctac accaagagat gcatggggc aggcagagca gctacaggtg    4980
agcagaggcc agtgggaggg ctggagggaa aggggctgc ccaggggctc tggaaggggg    5040
caggtagagc agctacaggt gagcagagga atgggagacc aggagggaca ggtcacagcc   5100
caggagcccc atgggtgtgg agagcagagc ttggcatgta agtaggaagc aggaagggct   5160
gaaggggcag gggctaccca gcagctccac aggagcaggc agagaagcta caggtgagca   5220
ggggccggtg ggagggctgc aggggcaggg ggctgcccag gagctccggg gagcaggcag   5280
agcagctaca ggtgagcagg ggccgatggg agggctgcag gggcagggg ctgcccagga    5340 gctccgggga gcaggcagag cagctacagg tgagcagggg ccgatgggag ggctgcaggg   5400
acctgcccag gagctctggc ggagtagtca gagcagctac aggtgagcag ggccagtgg    5460 gagggctgga ggcagggt cctgcccagg agttccaggg gagcaggcag agcagctata    5520
ggtgagcaga cgctggtgag aggtctggag gggcagggg ctgcccagga gctctagcgg    5580
gagcaggcag agaagctata ggtgagcagg gccggtggg agggctgcag gggccggggc    5640
ctgccgagga gctccggcgg ggtagtcagg gcagctatag gtgagcaggg gccggtggga    5700
gggctggagg ggcagtggga tacccaggag ctccgccagg gtagtcagag cagctacagg   5760
```

-continued

```
tgagcagggg caagcaggag ggctggaggg gcaggaggct gcccaggagc tccggcgggg    5820
tagtcagagc agctacaggt gagcaggtgc cagcgggagg gctggagggg cagggggctg    5880
cccaggagct ctgggaggag caggctgaga agctgtagtt gagcaggggc cagtgggagg    5940
gctggagggg caggcggctg cccaggagct ccggggagc aagcagagca gctataggtg    6000
agcaggggca ggtgggggg ctggaggggc agggcaatgc ccaggagctc cggcggggta    6060
gtcagagcag ctacagtgga gcaggtgcca gcgggaggc tggagggca gggggctgcc    6120 caggagctcc gggggagcag gcagagcagc tacaggtgag caggagcaag tgggagggct    6180
ggaggggcag aggactgctc aggagctccg ggggagcagg cagagcagct acaggtgagc    6240
aggagcaagt gggagggctg gaggggcaga ggactgctca ggagctccag gggagcaggc    6300
agaacagcta ctggtgagca ggggtcagcg ggagcgctgg aggggcaggg ggctgcccag    6360
gagctccggg ggagcaggca gagcagctat aggtgagcag gggcaggtgg gagggctgga    6420
ggggcagggc aatgcccagg agctccggcg gggtagtcag agcagctaca gtggagcagg    6480
tgccagcggg agggctggag gggcaggggg ctgcccagga gctcggggg agcaggcaga    6540 gcagctacag gtgagcaggg gccggtggga gggctgcagg ggcagggtcc tgcccaggag    6600
ctccacagga gcagacagag aagctatagg taagcagggc cggtgggaga gctggagggg    6660
cagggtccgg cccaggagtt ccggggagc aggcagagca ggtacaggtg agcaggcgct    6720
ggtgagaggt ctggagcggc aggtggctgc ccatgagctc tgggggagc aggcagagca    6780 gctataggtt agcagtggcc agcaggaggg ctggaggggc agggagcagt tcaaggagct    6840
ccagcggaat aatcagagca gctataggtg agcatgggcc agcgggaggg actgggacgg    6900
ggcagggagc tgccaggnnn nnnnnnnnn nnnnnnnnnn nnnnnnnnnn nnnnnnnnnn    6960
nnnnnnnnnn nnnnnnnnnn nnnnnnnnnn nnnnnnnnnn nnnnnnnnnn nnnnnnnnnn    7020
nnnnnnnnnn nnnnnnnnnn nnnnnnnnnn nnnnnnnnnn nnnnnnnnnn nnnnnnnnnn    7080
nnnnnnnnnn nnnnnnnnnn nnnnnnnnnn nnnnnnnnnn nnnnnnnnnn nnnnnnnnnn    7140
nnnnnnnnnn nnnnnnnnnn nnnnnnnnnn nnnnnnnnnn nnnnnnnnnn nnnnnnnnnn    7200
nnnnnnnnnn nnnnnnnnnn nnnnnnnnnn nnnnnnnnnn nnnnnnnnnn nnnnnnnnnn    7260
nnnnnnnnnn nnnnnnnnnn nnnnnnnnnn nnnnnnnnnn nnnnnnnnnn nnnnnnnnnn    7320
nnnnnnnnnn nnnnnnnnnn nnnnnnnnnn nnnnnnnnnn nnnnnnnnnn nnnnnnnnnn    7380
nnnnnnnnnn nnnnnnnnnn nnnnnnnnnn nnnnnnnnnn nnnnnnnnnn nnnnnnnnnn    7440
nnnnnnnnnn nnnnnnnnnn nnnnnnnnnn nnnnnnnnnn nnnnnnnnnn nnnnnnnnnn    7500
nnnnnnnnnn nnnnnnnnnn nnnnnnnnnn nnnnnnnnnn nnnnnnnnnn nnnnnnnnnn    7560
nnnnnnnnnn nnnnnnnnnn nnnnnnnnnn nnnnnnnnnn nnnnnnnnnn nnnnnnnnnn    7620
nnnnnnnnnn nnnnnnnnnn nnnnnnnnnn nnnnnnnnnn nnnnnnnnnn nnnnnnnnnn    7680
nnnnnnnnnn nnnnnnnnnn nnnnnnnnnn nnnnnnnnnn nnnnnnnnnn nnnnnnnnnn    7740
nnnnnnnnnn nnnnnnnnnn nnnnnnnnnn nnnnnnnnnn nnnnnnnnnn nnnnnnnnnn    7800
nnnnnnnnnn nnnnnnnnnn nnnnnnnnnn nnnnnnnnnn nnnnnnnnnn nnnnnnnnnn    7860
nnnnnnnnnn nnnnnnnnnn nnnnnnnnnn nnnnnnnnnn nnnnnnnnnn nnnnnnnnnn    7920
nnnnnnnnnn nnnnnnnnnn nnnnnnnnnn nnnnnnnnnn nnnnnnnnnn nnnnnnnnnn    7980
nnnnnnnnnn nnnnnnnnnn nnnnnnnnnn nnnnnnnnnn nnnnnnnnnn nnnnnngtt    8040 ccagggaatc ttctacaggg agctagatag agaaagttta taggtaaagc aggtgccggt    8100
```

| | |
|---|---|
| cgggagaagt tgaaggggca gggtcctgcc ccaggaagtt cccgggggga gccaggcaga | 8160 |
| gcaggttaca ggtgagcagg cgattgtgag aagtctggaa gcggcaggtg tcttcccatg | 8220 |
| agctcttggg gggagcaggc agagcagcta taggttagca gtggccagca ggaggggctg | 8280 |
| gaggggcagg gggcagccaa ggagctccag cggggtagtc agagcagcta taggtgagca | 8340 |
| ggggccagcg ggagggctgg aggggcaggg gacttccaag gagctccatg ggtgcagaca | 8400 |
| gagcagaaac tggtgagcag gggccggtga gagatctgga gttgcagggg gctgcccagg | 8460 |
| agctccgggg gagcaggcag agcagctact ggttgcaggg gcaggtggga gggctggagg | 8520 |
| ggcaggggcc tgcccaggat ctccagggag caggcagagc agctataggt gagcaggggc | 8580 |
| aggtgagagg gctggagggg cagcgggctg cccaggagct caggggagc aggcagagca | 8640 |
| gctactggtt gcagggcagg tgggagagct ggaggggcag cgtcctgccc aggagctcca | 8700 |
| caggagcaga cagagaagct ataggtaagc aggggccggt gggagagctg ggggggcagg | 8760 |
| gtcctgccca ggagttccgg gggagcaggc agagcaggta caggtgagca ggtgctggtg | 8820 |
| agaggtctgg agaggcaggg ggctgcccac gactttaggg gatgaagggc actgggcctg | 8880 |
| agttaaacag agccctcaac tggtgggacc tgaggggta cagggagcag ggacagctgg | 8940 |
| aggctcccag ggctcaggtc aggctggctg ggcaggggag agagttgagc tggttgagtt | 9000 |
| gccaggtgcc tgttgagttg gatggagggg ggcccctggg atggaaggag tctagggctg | 9060 |
| aaggggtcgg gggcatccct gagaggacca gatcggatgc agttcttggg tccaggcaca | 9120 |
| ccggccctgt tctggggttt gtggggacat gggacaggag ggatagacat tcggactcag | 9180 |
| tgtgggggtgg cacagcgcag tgggctcagt gcatggaaga gtaagagtcc ccttggggcc | 9240 |
| tgagcccagg ctaccagcat ggggagaggc caggcaaggc cctgcggctg agcagacagg | 9300 |
| actcagggga ggaggggaca gggtgggcct ggctgttggg ggtggaggct gcaccctggc | 9360 |
| ccacacgggg gcctggggag gctggcaccg agaggagagg agtgccgagc gcagcgcatg | 9420 |
| gctcccgccc cgcgcccaggg gccggctgtg ctggggaagg accacagctg gaggagggct | 9480 |
| ctgcagtgag caaggagctg gacaggccca agagcaggga gggcagaggg caggcggcgc | 9540 |
| tggcagggag gggccggagg tgagctcagg aagccgggcc aggaggacct gagcgggtag | 9600 |
| ggggcccaga ggcacatgca ggaggctggg ctggggacac acagggatgg gaggggaggg | 9660 |
| ggacaagaag actcccaggg atggggtcca gtacacggat ggagtccagg gaagggacgg | 9720 |
| ggtccaggac agggaaggga tgggttcagg acagggatgg ggtcgagggc aaggacaaag | 9780 |
| cccaaggcat gaacagggtt caagacagga tcaggatcag ggggagcgttg gggacaagta | 9840 |
| ctcctggtgc tgtggctgtg gagctgactc agatgacacg tggcctggcg agcagagaca | 9900 |
| ggccatggca aagtcactga gctgagggggc cgggagacaa cagggacagt gcggcgcaga | 9960 |
| ggcccaccac acctgaagag atgcccaatc gcccagggct gggccaggct ggggccacag | 10020 |
| gacagcagat tagggtccat cagaagccga ccagaagcac aggtctctgg tccgggctca | 10080 |
| gactggggac tcagtcaggc gggccacctg caggaggcct gagcagggac aaggggcagg | 10140 |
| ggccccaggg ggctctaatc taggttctct gagcctgtgg ctgcagaggc accagccctg | 10200 |
| atgacaggca gccacaaggg gcatctaggc ctcagactct ctggaaacac acgggcgcag | 10260 |
| gggcaggccc tggtggtcac acgcctcctc tcttgcag | 10298 |

<210> SEQ ID NO 4
<211> LENGTH: 9313
<212> TYPE: DNA
<213> ORGANISM: Sus scrofa

<400> SEQUENCE: 4

```
ggtatatata cacactagaa taccactcgg ccgtaaaaac gaaccaaata atgccattgg      60
cagcaacacg gatggaacca gagactctca tactaagtga agtaagtcag aaagaccaat     120
accatacgct atcacgtaca tctggaatct aatatatggc acaaataaac ctttccacag     180
aaaagaaacc catggacttg gagaaaatac ttgtggtcgc caagggtgag gtagtggggt     240
agactgggag tttggggtta gtagatgcaa catattgcat ttggcataga taaactatga     300
gatcctgctg gagagcacag ggagctgtat ctagtccctt gtgatggaac atgttggagg     360
ataaagtgag aaaagaaaca tataaatata tacaccacac gcacacacac acacatatat     420
gaatgactgg gtcactttgc cgtagagtag aaattgacag aacacagtaa atcaactata     480
acggaaaaaa ataaaaaaca ttaaaaaaaa aaaacagat gctcatctcc atggattctg      540
aacacatttt tgacagaatt caacacccaa ctttttcttg atgattttta ttttttccac     600
tgcaggtggt ttaccctgct ctgttgattc cactgtacag aaaagtgaca aagtcacaca     660
catatatata tgtagacatt cttttttctca cattatcctc catcatgccc catcataggt     720
gactagatag agggaaacta caccaacata ctaaaagcca tatgacaaa cccacaact     780
atcatcattc tcaatggtga aaacctgaaa gcatttccgc taagatcagg aacaagacaa     840
ggatgtctgc tctcaccact ctccttccac ggagttttgg aagtcctagc cagggcaatt     900
agagaagaaa aggaatccaa atcggaaacg gagaagtaac actaccgctc tttacaggtg     960
acgtgctgcg ataccctagag aatcctcaag gcactaccag aaacctctta gagctcgcca    1020
atgaatttgg tcaagctgca ggatacaaaa ttaacacaca gaaattggct gccttgctct    1080
acgttaacaa tgaaagagca gcgagagaaa ctagggaaac catcccactg agcagtgcct    1140
cgaaatgaat gaaatgccca ggaataaacc tacccaaaga cacaaagacc tggactctga    1200
aaaccataag gcactgctgg aagcaaccaa agacgacaca aaccggtgga aagctagacc    1260
atgctcctgc cctggaagaa ttaatactgg caaaagggcc ataccaccta aggccaccct    1320
cactctcagt gcaatccctc tcaaatctcc aatggcattt tccacagaac tagaacaaaa    1380
aacctcaaaa atttgcatgg aaacacaaat acctcactga cctgggctat actacaaagc    1440
tgcagtcatc aaaacggtat ggcactgaca ctcccccccca aaaagacat acatatcagt    1500
ggaacagaac agaaagccca gcaataaacc caagcaccta tgctcaatcc atccatgaca    1560
taggaggcaa gactattcaa cagagaaggg agagtcactt cactaagtgg tgctggggag    1620
ctggacagct ccatgtaaag aatgaaacca gaacactccc aaacgccaaa cacaccaaaa    1680
aaaacaaaa aacaaaaaaa aaaaaataaa aaaccctca aaacaaatga aactcctaaa     1740
cgtaagactg gatacctata actcacagag gaaacaggc agaacgttct ttgacataaa    1800
tcacagcaac atcttatttg atccacctcc tggaataact acaataaaga caaaagtgga    1860
gttcccgtca cggctcagtg gtaaccaaat ctgactagga accatgaggt tgcgggttca    1920
atccctggcc ttgatcagtg ggttaaggat ccggcgttgc cgtcagctgt ggtgtaggtt    1980
gcagacgcgg ctcggatccc acgttgctgt ggctctggtg taggccgaca gctcagctc    2040
caattcgacc cctagcctgg gaacctccac atgccatggg tgcggccctg gaaagacaa    2100
aagacgggg aaaaatgaa agaaagaaag aaggaaagaa ggaaaggagg aaagaagaaa    2160
gaaagaaaga aagaaagaaa gaaagaaaga agaaagaca gacagacaaa agtaaaccaa    2220
tgagatctaa ttaaactcaa aagcttttga aaagcaaaag aaaccatttt aaaagagaaa    2280
```

```
aacaggagtt cccgtcctgg ctcaggggtt aacgaatctg actagcatcc atgaggaggc   2340
agatttgatc cctggcctca ctcagcaggt taaggatccg gcattgccat gagctgtgag   2400
ctgtggtgta ggccagcagc cgtagctcca attcaacccc tagcccggga acctccatat   2460
gccacaggtg gggccctaaa aaccaaaaaa gacaaaggaa acaacccac agaatgggac    2520 aaaatctttg caaacaatgc agcccaccaa ggctcaatcc ccaaaatata caaacactct   2580
acaactcaac aacaacaaaa aacaaaccaa caaacaaccc aatcgataaa tgggcagaag   2640
acctaaatag acatttctcc aaagaagaca tacagatggc cagaagacac atgaaaaaat   2700
cctcaacagc actaattttt agggaaatgc aaatcaaaac tgcaatgagg caccacctca   2760
cactggtcag aatggccatc attaagagtc aactaacagc aaatgctgga gagggtgagg   2820
agaagaggga acccgccttc actgttggtg ggaatgcaac ttggtacaag cactgtggaa   2880
aacagtatgg aggaacctca gaaaactgaa cgtaaaacca cgattgaacc cagaaatctc   2940 accectaggc ctgtatctcg atacgacttt cagtcaaaaa cttacatgca caactatgga   3000 cttttgcagaa gggttcaaaa tgggcaggac atgaaaacac tcaaacgccc atcaacagac   3060
gaacggatta agatgtggtt ctcacacaaa gtaagaacta cgtctcagcc gtaaaaaagg   3120
accaagtcac gccatttgca gcaacgtgga tggaactaga gactctcaca ctgagtgaag   3180
taagtcagaa agagaaagac agagaccaca tgataccact tatatgtgga atctaaaata   3240
cggcgcgatt gatcctgtgg acaaaacaga gacagagcat ggtcatggag agcagacttt   3300
gctttccagg gggagggaga gaagagattg acaggggggtt tggagctggt agatgcaact   3360
gatcacattg aaaacgagta agtgatgggt cctactgggc agcacacgga acagtgcccg   3420
gcctcttgcg ttagaacgtg agagaggaag gagagtgtga aaagaaaaag aaggtaaatg   3480
tatgtacagc tgtacaaggg taattgaagg aacgttgtaa atcaactctg gttttaaaaa   3540
aaaaaaaaaa aatttaaaga aagaaaacgt tctccagagg cagaacgaga aggtggaacg   3600
gccgacaggt ctctgtcctg cagcggccgc tgacacgacc ccaggacagc ggaaatgaga   3660
cccaggctgc ctgtcgggca cacggcggcc gccccggcac cctggtgatc ctgtgcagca   3720
cgaggtgccc agtagagggg tgggcagggc agggcagggc agggcaggac ctggggacgc   3780
ggccgcagca ggtgggctcc agccaggaag gagccacgag tgggtggggg tctgctcgct   3840
gggctggagg cagggagggc acctcggctc aacatcccca gccggggacc cggccagagg   3900 aagggggctgc gaggatgtct tccaagcatc tctttgctct tggaaccacg tggcgaagct   3960
ttctgaaagc agaccagact gcagcaccac ggtttctatt gtgaagggat ttttccagaa   4020
ggagtgggac cttgcgaacg gggatgtgga cacagggtgg cttctgatca gcccagggc    4080 cctgtgcagc caagtctcat ggtcacgccg tccggccgg accagcctgc cccccacgcg    4140
gacccgggga aggcagggg cccatgacca gcacgagaac gactgactcg ccttgacctc    4200
aagccacctc caggaccagg ggcagacggc ccggcaccac gaggaggagg cagagccccg    4260
ggcagggccc acttgccact tcacctcgcc agagagccgg gcagatggcg gcacgcgact    4320
cttggggcct gacggccccg agcccagacg ctctcgggggc tttggccaga ctcgcagggc   4380
tgctgagcca agcagaggct acaaagctcc acgggcttcc aggcaaccgc tagagacacg   4440
tgggcacagc tcgcagagcc ggtgacccac gggccagatg ggaacctccc tcctgtgccc   4500
cctcaaggcg tctcccggaa cgtggcctc ccacggcgct ggacgggggct cgggcaggc    4560 ccgaggcagc acgcgcccca caccgtccac tggccgcttg gaaggattca gccaacacca   4620
ccccaggccc gctgcacagc cggggtgggg gctgagacgt ccctcagggg tcccccagtcc   4680
```

```
cagcctgatg ctgaagttac aggacggccc aggggcgccc aggggacagg gggagctgcg    4740
gccctccacg aatgaggaca gagggtccct gaccccacg cacggccggc aggtctcggt     4800
ccacgcagag cagtgagcgg ctgcccgcca gcccgctctc ggccgggcac caccttcaca    4860 accctggga actctgtccc cacgtgggca gcacgggcct gggtctgggc agcaggctgg     4920
gcccagccac acacgcgggg gtcacaagag gtgcccggtg gggtcgggca accaagggct    4980
cacactaggg gcctggcacc cgggctgcag taggccaggc ggcataatcc ccgtgggaca    5040
tagagaacca cgacgtcctg agttcccgca ccctccccac cgctcaccca cccacacac    5100 ccacatgagc cgccagggca ctgtctggac tcccccaggc cctctgggac agaaagcaac    5160
cagaagaaaa gggaacttca ggaagcagcc gggccacccg gtttcaatcc cattcttagt    5220
gtgcagggct gtgggcagga aggtcgtgcc tccaggacc agacacccac ccgaggaagc     5280
agggctgcag gcacagagca cagacacaaa gagccacatg cacctggggc cagagcagga    5340
ggggcccgga gcccggggca gcaggggagc cacctcctcg gcccccacac tcggtgcgtg    5400
gggttcacga agaccagggg caggggcagc ggagggggga cgaggagggg agaccccaca    5460
gcagggctgc agccgaccca gcccagggaa cacagcctgc acgcgggtca tgtcgcccgc    5520
ccagcacagg gaccagggag ccctggcagg ggcacgccca cgccaacaga ggtggtgccc    5580
cagaggccag aggaggtcgg tggggccgcc aggcctctgc ggaacatgat gggctgcggt    5640
cagaggcctg agggatctgc tcggccaggt tgctggaggc acagggctgg gcaggggctg    5700
aggacgaggc caggatggac aggtgggtct gggcggagga ctcagggaag agacggacac    5760
agcgcagggg acaaagaggt cacctggggt tgcagggtcc tgtcccggct gccggagccc    5820
gcttgagccc cagggcaggt atgaaagcag taactgtcgg gtcccgggga aggagccagg    5880
gccacgggca gcaggtgagc cgggagcaga gcaggcaggg cgggccgggc tcctgtgtgc    5940
ccagagctgg cagcacaggg actgagccta aagctccaca ggccgcagga gggctgacgg    6000
gagccagggg cctgagggca ggagcgggag ccaggggctg ggagctgggc gccagtgcag    6060
ctgagccagc aactagaggg agccaggga cagacaggct ccaagggtgg tcgcggcgag     6120
aagagggtga gctcagaagg gtcaggagcc cctccgggag gggaccaggt gggacagagg    6180
ctctgccagg gggacgctac ccagagaggg tgggcaccca gggctccggg aacaaaggcc    6240
agccctggga aagaaaggaa gccaggagtg gagctagaca aggctgaggg ttcggggca     6300 ggaagagggg tggtgacact gaggcccagg agcccaggg aaaggggcag gtaggctgca    6360
ggtgagcagg gaaccgggag ggcggaaaag ctgtccttag agctgctggg aacacataga    6420
gctggtgcag gtgaggaggg gttgggaggg caaggggct gaacctgaag ctcctcggaa    6480
ctggtagagc ttgtgcagat gagcagggc tgggagggca ggggcagcc ctgggaccac    6540 ctgagagctg tagatcttgg gcaggtgagc acaaactggt agggcagggg aagaacctgc    6600
agttcctggg agcaggagga gcttgtgcag gtgagcaggg gctggagggc aggggctaa    6660 acctggagct attgggaaga ggttaggctt gtgcaggcga gcagggggtg ggagggcgag    6720
ggtcagtcct gggagccctt tcgagccaat agagcccagg caggtgagca ggggcttggc    6780 gggcaggag catccctggg atgagtttgt gcaggtgagc agggggtggg agtgtaggga    6840
gcagtcctag caactcctgg gagctggtag agcttgggca ggtgaacagg ggctggaagt    6900 gcaggggca catctgggag gccctggag caattagcgc tctggcaggt gagtaggggc    6960
tcggagggca gggagcagcc ctgggagctc cttggagcag gtagagcttg gcaggtgag    7020
```

```
caggggggtgg gagggcaggg ggcagtccta gcaactcctg ggagcttgta gagcttgggc      7080
aggtgagaac gagctggtag ggcagggaa tgaacctgga gttactgggt caggaggagc       7140
atgtgcaggt gagcaggggc tggagggcag ggggctaaac ctggagctat tgggaagagg      7200
ttaggcttgt gcaggcaagc aggggtgggg agagcaaggg tcagtcctgg gagcccttgc      7260
gagccggtag agcccaggca ggtgagcagg ggctgggcgg gcagggagca gtcctagcaa      7320
ctcctgggag caggtagagc ttgtgcaggt gagcagggggg tggagggta gggagcagtc     7380
ctgggaactc ctgcgagcag gtagagcttg tgcaggtggg caggggtggg agggcagggg     7440
gctgaacctg gagctcctca gaactggtag agcttgtgca gatgagcagt ggctgggagg     7500
gcagggggca gccctgggag caatagacct tgggcaggtg agaacgagct ggtagggcag     7560
tggaatgaac ctggagttac tgggtcaaga gagcttgtg caggcaagca ggggctgaag      7620
ggcagggggc taaacctgga gctattggga agaggttagg cttgtgcagg cgagcagggg     7680
gtgggagggc aagggtcagt cctgggagcc cttgcgagcc ggtagagccc aggcaggtga     7740
gcaggggctg ggagggcagg gagcatccct gggacctctt gggagcaggt agagcttgtg     7800
caggtgagca gggggtggga gggtaggag ccgtcctagc aactcctgaa tctggtagag      7860
cttgcgagg tgaacagggg ctgggagtgc agggggcagt cctgggagcc cctgggagta      7920
attagagctt gggcaggtga gcaggagctt ggagtctagg gggctaaact ggagctattg     7980
ggaagagttt aggcttgttc aggtgagcaa ggggtgggag tagaggggc attcctagga      8040
gctcccgcga gttggtcaat ctcgggcagg taagcagggg ctcagaggcc tggagcagcc     8100
ctgggaccat ctgggagcag ggcgagcttg ggcaggtgag ccgggccagg ggggatgcag     8160
gacagggcag gggcaacaga gtgggggtga gctcagggga gccccaggct cgagggaggg     8220
gccgatatag ggctagccag gctggaaagt gggctcctgg ggggaaggtc cccaggactg     8280
cgggggcagg ggcagggctg aacagacgcc atgggtcaca gggatcgggc caacgggcca     8340
taccctgttc cagcaaagtg agtggacatg ggacagagca gctggagtcc taagtgagaa     8400
cagcggcaca gggcagtgca catggtcggg gggtcgaggg gctcatctgg gcctgagctg     8460
gggaagcagg caatggctga acagaacagg ggggagagga ccggcccaac cgggcagggg     8520
cgcatgggt gctggcgccc cgtgggagag gaaggccagg ggcagggctc ggctgcagca     8580
gtgctgccag gcaggctggc agcgggaagg gcaggagcag agggaggggct ctggcctcag    8640
caggcagctg ggaggcccag agctgggctg caggggccgg ggctctgggg aaagctgcct     8700
cgggtgagct cagggccaag ccaggagccc cggtggagga gggaccggtg ggcccagagg     8760
cccagatttg gagcctgggc cagggccgga gggatggcag gggaggggcc tcggaggaga     8820
ctacctgccc tcgcccaggg aaaggggcat gttggtgcca gggaccaacg cgcacgggcc     8880
ttgactgcag agctgaccca gggaacggg gcctggagag caaacagcag gccaggacca     8940
ggggccagga gcagagcatg ggcagtgggt ggcagtgggt ggcagtgtcc ctgccaggct     9000
ggggaagcag gacggtggcc tcaggggacc agcagaagct ggccaggaac acaggccacc     9060
cgctggtcgg gccaggcacc cacaggggct ctgggccctg gcgggctctc atccaggcgg     9120
tcacccagct ctgaccaggc agctgcgccc agaacctgca gctgcaatgg cagcgagctg     9180
ggcggctggt ctgccgactt tctggaagca agtgggtgct gggcgcagcg gccccgctgt     9240
tctgagggcc cgattcgctg cccgccccac aaggaacaag gccctggcgg tcacgcagcc     9300
tcctctcttc cag                                                        9313
```

<210> SEQ ID NO 5
<211> LENGTH: 337
<212> TYPE: DNA
<213> ORGANISM: Bos taurus

<400> SEQUENCE: 5

```
tccactaggg tggccaggca cagtcaccag aggggaggg ctcgggtgca ggggtgcggg      60
agggtggggg aggcagcggt gtttgtgtcc tcttgttttt ctctttcttc tcaagccccc     120
tgcacctcat cacctgctga aacatccaaa atagctctag gtggctactg agtcattgcg     180
agcacagccc aacccaggtg tcccagccag gctgctcttc tgagaatcgg ccccaaaac     240
cgagacctgg ccaggtgggc ctgggcctg ggcccgggc caaagcccag ggagtccta       300
cgggggcagt gagttcccca aggcctggag agggccc                             337
```

<210> SEQ ID NO 6
<211> LENGTH: 246
<212> TYPE: DNA
<213> ORGANISM: Bos taurus

<400> SEQUENCE: 6

```
ccccaccccc taggcaggtg cgaggccctc tcagtttccc ccaggttact catttggggc     60
acactcagcc ttgcagggca tgcaaatggc tgtttgttcc acactgaaaa acatgtctaa    120
gcctctgtgg ttatttccag aaatagccta cgcccacgcc ccacctgcag ccccagctct    180
gaccctccag agtgccaggc tggcctggag ctcaggattc gggggaccct gcaccccctg    240
ccccag                                                               246
```

<210> SEQ ID NO 7
<211> LENGTH: 145
<212> TYPE: PRT
<213> ORGANISM: Homo sapiens

<400> SEQUENCE: 7

```
Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Glu Met Glu Pro Thr Ala Ala Arg Thr Arg Val
    130                 135                 140

Pro
145
```

<210> SEQ ID NO 8
<211> LENGTH: 123
<212> TYPE: PRT

<213> ORGANISM: Homo sapiens

<400> SEQUENCE: 8

Met Ala Cys Arg Cys Leu Ser Phe Leu Leu Met Gly Thr Phe Leu Ser
1               5                   10                  15

Val Ser Gln Thr Val Leu Ala Gln Leu Asp Ala Leu Leu Val Phe Pro
            20                  25                  30

Gly Gln Val Ala Gln Leu Ser Cys Thr Leu Ser Pro Gln His Val Thr
        35                  40                  45

Ile Arg Asp Tyr Gly Val Ser Trp Tyr Gln Gln Arg Ala Gly Ser Ala
    50                  55                  60

Pro Arg Tyr Leu Leu Tyr Tyr Arg Ser Glu Glu Asp His His Arg Pro
65                  70                  75                  80

Ala Asp Ile Pro Asp Arg Phe Ser Ala Ala Lys Asp Glu Ala His Asn
                85                  90                  95

Ala Cys Val Leu Thr Ile Ser Pro Val Gln Pro Glu Asp Asp Ala Asp
            100                 105                 110

Tyr Tyr Cys Ser Val Gly Tyr Gly Phe Ser Pro
        115                 120

<210> SEQ ID NO 9
<211> LENGTH: 177
<212> TYPE: DNA
<213> ORGANISM: Homo sapiens

<400> SEQUENCE: 9
gtcacatctg gactccccca ggccctctga gacagaaaac actcagaaga aagggaact      60 tcaggaagca agtcgcgtca ccaggtttca ttcctgttct tagtcttcac agcactgggg    120 gaagggcccct cacgcctcct gggactggtg accaagtccc agggagcagg gctgcag      177

<210> SEQ ID NO 10
<211> LENGTH: 476
<212> TYPE: PRT
<213> ORGANISM: Bos taurus

<400> SEQUENCE: 10

Glu Gly Glu Ser His Pro Arg Val Phe Pro Leu Val Ser Cys Val Ser
1               5                   10                  15

Ser Pro Ser Asp Glu Ser Thr Val Ala Leu Gly Cys Leu Ala Arg Asp
            20                  25                  30

Phe Val Pro Asn Ser Val Ser Phe Ser Trp Lys Phe Asn Asn Ser Thr
        35                  40                  45

Val Ser Ser Glu Arg Phe Trp Thr Phe Pro Glu Val Leu Arg Asp Gly
    50                  55                  60

Leu Trp Ser Ala Ser Gln Val Val Leu Pro Ser Ser Ala Phe
65                  70                  75                  80

Gln Gly Pro Asp Asp Tyr Leu Val Cys Glu Val Gln His Pro Lys Gly
                85                  90                  95

Gly Lys Thr Val Gly Thr Val Arg Val Ile Ala Thr Lys Ala Glu Val
            100                 105                 110

Leu Ser Pro Val Val Ser Val Phe Val Pro Pro Arg Asn Ser Leu Ser
        115                 120                 125

Gly Asp Gly Asn Ser Lys Ser Ser Leu Ile Cys Gln Ala Thr Asp Phe
    130                 135                 140

Ser Pro Lys Gln Ile Ser Leu Ser Trp Phe Arg Asp Gly Lys Arg Ile
145                 150                 155                 160

Val Ser Gly Ile Ser Glu Gly Gln Val Glu Thr Val Gln Ser Ser Pro
            165                 170                 175

Ile Thr Phe Arg Ala Tyr Ser Met Leu Thr Ile Thr Glu Arg Asp Trp
            180                 185                 190

Leu Ser Gln Asn Val Tyr Thr Cys Gln Val Glu His Asn Lys Glu Thr
            195                 200                 205

Phe Gln Lys Asn Val Ser Ser Cys Asp Val Ala Pro Pro Ser Pro
            210                 215                 220

Ile Gly Val Phe Thr Ile Pro Pro Ser Phe Ala Asp Ile Phe Leu Thr
225                 230                 235                 240

Lys Ser Ala Lys Leu Ser Cys Leu Val Thr Asn Leu Ala Ser Tyr Asp
            245                 250                 255

Gly Leu Asn Ile Ser Trp Ser Arg Gln Asn Gly Lys Ala Leu Glu Thr
            260                 265                 270

His Thr Tyr Phe Glu Arg His Leu Asn Asp Thr Phe Ser Ala Arg Gly
            275                 280                 285

Glu Ala Ser Val Cys Ser Glu Asp Trp Glu Ser Gly Glu Glu Phe Thr
            290                 295                 300

Cys Thr Val Ala His Ser Asp Leu Pro Phe Pro Glu Lys Asn Ala Val
305                 310                 315                 320

Ser Lys Pro Lys Asp Val Ala Met Lys Pro Pro Ser Val Tyr Leu Leu
            325                 330                 335

Pro Pro Thr Arg Glu Gln Leu Ser Leu Arg Glu Ser Ala Ser Val Thr
            340                 345                 350

Cys Leu Val Lys Gly Phe Ala Pro Ala Asp Val Phe Val Gln Trp Leu
            355                 360                 365

Gln Arg Gly Glu Pro Val Thr Lys Ser Lys Tyr Val Thr Ser Ser Pro
            370                 375                 380

Ala Pro Glu Pro Gln Asp Pro Ser Val Tyr Phe Val His Ser Ile Leu
385                 390                 395                 400

Thr Val Ala Glu Glu Asp Trp Ser Lys Gly Glu Thr Tyr Thr Cys Val
            405                 410                 415

Val Gly His Glu Ala Leu Pro His Met Val Thr Glu Arg Thr Val Asp
            420                 425                 430

Lys Ser Thr Glu Gly Glu Val Ser Ala Glu Glu Gly Phe Glu Asn
            435                 440                 445

Leu Asn Thr Met Ala Ser Thr Phe Ile Val Leu Phe Leu Ser Leu
450                 455                 460

Phe Tyr Ser Thr Thr Val Thr Leu Phe Lys Val Lys
465                 470                 475

<210> SEQ ID NO 11
<211> LENGTH: 471
<212> TYPE: PRT
<213> ORGANISM: Equus ferus

<400> SEQUENCE: 11

Glu Ser Thr Lys Thr Pro Asp Leu Phe Pro Leu Val Ser Cys Gly Pro
1               5                   10                  15

Ser Leu Asp Glu Ser Leu Val Ala Val Gly Cys Leu Ala Arg Asp Phe
            20                  25                  30

Leu Pro Asn Val Ile Thr Phe Ser Trp Asn Tyr Gln Asn Asn Thr Val
            35                  40                  45

Val Arg Ser Gln Asp Ile Lys Asn Phe Pro Ser Val Leu Arg Glu Gly

```
                50                  55                  60
Lys Tyr Thr Ala Ser Ser Gln Val Leu Leu Pro Ser Gly Asp Val Pro
 65                  70                  75                  80

Leu Val Cys Thr Val Asn His Ser Asn Gly Asn Lys Lys Val Glu Val
                 85                  90                  95

Arg Pro Gln Val Leu Ile Gln Asp Glu Ser Pro Asn Val Thr Val Phe
            100                 105                 110

Ile Pro Pro Arg Asp Ala Phe Thr Gly Pro Gly Gln Arg Thr Ser Arg
        115                 120                 125

Leu Val Cys Gln Ala Thr Gly Phe Ser Pro Lys Glu Ile Ser Val Ser
    130                 135                 140

Trp Leu Arg Asp Gly Lys Pro Val Glu Ser Gly Phe Thr Thr Glu Glu
145                 150                 155                 160

Val Gln Pro Gln Asn Lys Glu Ser Trp Pro Val Thr Tyr Lys Val Thr
                165                 170                 175

Ser Met Leu Thr Ile Thr Glu Ser Asp Trp Leu Asn Gln Lys Val Phe
            180                 185                 190

Thr Cys His Val Glu His Gln Gln Gly Val Phe Gln Lys Asn Val Ser
        195                 200                 205

Ser Met Cys Ser Pro Asn Ser Pro Val Pro Ile Lys Ile Phe Ala Ile
    210                 215                 220

Pro Pro Ser Phe Ala Gly Ile Phe Leu Thr Lys Ser Ala Lys Leu Ser
225                 230                 235                 240

Cys Gln Val Thr Asn Leu Gly Thr Tyr Asp Ser Leu Ser Ile Ser Trp
                245                 250                 255

Thr Arg Gln Asn Gly Glu Ile Leu Lys Thr His Thr Asn Ile Ser Glu
            260                 265                 270

Ser His Pro Asn Gly Thr Phe Ser Ala Leu Gly Glu Ala Thr Ile Cys
        275                 280                 285

Val Glu Asp Trp Glu Ser Gly Asp Asp Tyr Ile Cys Thr Val Thr His
    290                 295                 300

Thr Asp Leu Pro Phe Pro Leu Lys Gln Ala Ile Ser Arg Pro Asp Ala
305                 310                 315                 320

Val Ala Lys His Pro Pro Ser Val Tyr Val Leu Pro Pro Thr Arg Glu
                325                 330                 335

Gln Leu Ser Leu Arg Glu Ser Ala Ser Val Thr Cys Leu Val Lys Gly
            340                 345                 350

Phe Ser Pro Pro Asp Val Phe Val Gln Trp Leu Gln Lys Gly Gln Pro
        355                 360                 365

Leu Ser Ser Asp Lys Tyr Val Thr Ser Ala Pro Met Pro Glu Pro Gln
    370                 375                 380

Ala Pro Gly Leu Tyr Phe Val His Ser Ile Leu Thr Val Ser Glu Glu
385                 390                 395                 400

Asp Trp Ser Ser Gly Glu Thr Tyr Thr Cys Val Val Gly His Glu Ala
                405                 410                 415

Leu Pro His Val Val Thr Glu Arg Thr Val Asp Lys Ser Thr Glu Gly
            420                 425                 430

Glu Val Ser Ala Glu Glu Glu Gly Phe Glu Asn Leu Ser Ala Met Ala
        435                 440                 445

Ser Thr Phe Ile Val Leu Phe Leu Leu Ser Leu Phe Tyr Ser Thr Thr
    450                 455                 460

Val Thr Leu Phe Lys Val Lys
465                 470
```

<210> SEQ ID NO 12
<211> LENGTH: 476
<212> TYPE: PRT
<213> ORGANISM: Ovis aries

<400> SEQUENCE: 12

```
Glu Ser Glu Ser His Pro Lys Val Phe Pro Leu Val Ser Cys Val Ser
1               5                   10                  15

Ser Pro Ser Asp Glu Asn Thr Val Ala Leu Gly Cys Leu Ala Arg Asp
                20                  25                  30

Phe Val Pro Asn Ser Val Ser Phe Ser Trp Lys Phe Asn Asn Ser Thr
            35                  40                  45

Val Ser Ser Glu Arg Phe Trp Thr Phe Pro Glu Val Leu Arg Asp Gly
        50                  55                  60

Leu Trp Ser Ala Ser Ser Gln Val Ala Leu His Ser Ser Thr Phe
65                  70                  75                  80

Gln Gly Thr Asp Gly Tyr Leu Val Cys Glu Val Gln His Pro Lys Gly
                85                  90                  95

Gly Lys Thr Val Gly Thr Val Met Val Val Ala Pro Lys Val Glu Val
            100                 105                 110

Leu Ser Pro Val Val Ser Val Phe Val Pro Pro Cys Asn Ser Leu Ser
        115                 120                 125

Gly Asn Gly Asn Ser Lys Ser Ser Leu Ile Cys Gln Ala Thr Asp Phe
130                 135                 140

Ser Pro Lys Gln Ile Ser Leu Ser Trp Phe Arg Asp Gly Lys Arg Ile
145                 150                 155                 160

Val Ser Asp Ile Ser Glu Gly Gln Val Glu Thr Val Gln Ser Ser Pro
                165                 170                 175

Thr Thr Tyr Arg Ala Tyr Ser Val Leu Thr Ile Thr Glu Arg Glu Trp
            180                 185                 190

Leu Ser Gln Ser Ala Tyr Thr Cys Gln Val Glu His Asn Lys Glu Thr
        195                 200                 205

Phe Gln Lys Asn Ala Ser Ser Cys Asp Ala Thr Pro Pro Ser Pro
210                 215                 220

Ile Gly Val Phe Thr Ile Pro Pro Ser Phe Ala Asp Ile Phe Leu Thr
225                 230                 235                 240

Lys Ser Ala Lys Leu Ser Cys Leu Val Thr Asn Leu Ala Ser Tyr Asp
                245                 250                 255

Gly Leu Asn Ile Ser Trp Ser His Gln Asn Gly Lys Ala Leu Glu Thr
            260                 265                 270

His Thr Tyr Phe Glu Arg His Leu Asn Asp Thr Phe Ser Ala Arg Gly
        275                 280                 285

Glu Ala Ser Val Cys Ser Glu Asp Trp Glu Ser Gly Glu Glu Tyr Thr
290                 295                 300

Cys Thr Val Ala His Leu Asp Leu Pro Phe Pro Glu Lys Ser Ala Ile
305                 310                 315                 320

Ser Lys Pro Lys Asp Val Ala Met Lys Pro Pro Ser Val Tyr Val Leu
                325                 330                 335

Pro Pro Thr Arg Glu Gln Leu Ser Leu Arg Glu Ser Ala Ser Val Thr
            340                 345                 350

Cys Leu Val Lys Gly Phe Ala Pro Ala Asp Val Phe Val Gln Trp Leu
        355                 360                 365

Gln Lys Gly Glu Pro Val Ala Lys Ser Lys Tyr Val Thr Ser Ser Pro
```

```
                370                 375                 380
Ala Pro Glu Pro Gln Asp Pro Ser Ala Tyr Phe Val His Ser Ile Leu
385                 390                 395                 400

Thr Val Thr Glu Glu Asp Trp Ser Lys Gly Glu Thr Tyr Thr Cys Val
                405                 410                 415

Val Gly His Glu Ala Leu Pro His Met Val Thr Glu Arg Thr Val Asp
                420                 425                 430

Lys Ser Thr Glu Gly Glu Val Ser Ala Glu Glu Gly Phe Glu Asn
                435                 440                 445

Leu Asn Thr Met Ala Ser Thr Phe Ile Val Leu Phe Leu Leu Ser Leu
                450                 455                 460

Phe Tyr Ser Thr Thr Val Thr Leu Phe Lys Val Lys
465                 470                 475

<210> SEQ ID NO 13
<211> LENGTH: 477
<212> TYPE: PRT
<213> ORGANISM: Sus scrofa

<400> SEQUENCE: 13

Glu Ser Gln Ser Ala Pro Asn Leu Phe Pro Leu Val Ser Cys Val Ser
1               5                   10                  15

Pro Pro Ser Asp Glu Ser Leu Val Ala Leu Gly Cys Leu Ala Arg Asp
                20                  25                  30

Phe Leu Pro Ser Ser Val Thr Phe Ser Trp Asn Tyr Lys Asn Ser Ser
            35                  40                  45

Lys Val Ser Ser Gln Asn Ile Gln Asp Phe Pro Ser Val Leu Arg Gly
50                  55                  60

Gly Lys Tyr Leu Ala Ser Ser Arg Val Leu Leu Pro Ser Val Ser Ile
65                  70                  75                  80

Pro Gln Asp Pro Glu Ala Phe Leu Val Cys Glu Val Gln His Pro Ser
                85                  90                  95

Gly Thr Lys Ser Val Ser Ile Ser Gly Pro Val Val Glu Glu Gln Pro
                100                 105                 110

Pro Val Leu Asn Ile Phe Val Pro Thr Arg Glu Ser Phe Ser Ser Thr
            115                 120                 125

Pro Gln Arg Thr Ser Lys Leu Ile Cys Gln Ala Ser Asp Phe Ser Pro
    130                 135                 140

Lys Gln Ile Ser Met Ala Trp Phe Arg Asp Gly Lys Arg Val Val Ser
145                 150                 155                 160

Gly Val Ser Thr Gly Pro Val Glu Thr Leu Gln Ser Ser Pro Val Thr
                165                 170                 175

Tyr Arg Leu His Ser Met Leu Thr Val Thr Glu Ser Glu Trp Leu Ser
                180                 185                 190

Gln Ser Val Phe Thr Cys Gln Val Glu His Lys Gly Leu Asn Tyr Glu
            195                 200                 205

Lys Asn Ala Ser Ser Leu Cys Thr Ser Asn Pro Ser Pro Ile Thr
    210                 215                 220

Val Phe Ala Ile Ala Pro Ser Phe Ala Gly Ile Phe Leu Thr Lys Ser
225                 230                 235                 240

Ala Lys Leu Ser Cys Leu Val Thr Gly Leu Val Thr Arg Glu Ser Leu
                245                 250                 255

Asn Ile Ser Trp Thr Arg Gln Asp Gly Glu Val Leu Lys Thr Ser Ile
                260                 265                 270
```

```
Val Phe Ser Glu Ile Tyr Ala Asn Gly Thr Phe Gly Ala Arg Gly Glu
            275                 280                 285

Ala Ser Val Cys Val Glu Asp Trp Glu Ser Gly Asp Arg Phe Thr Cys
        290                 295                 300

Thr Val Thr His Thr Asp Leu Pro Ser Pro Leu Lys Gln Ser Val Ser
305                 310                 315                 320

Lys Pro Arg Gly Ile Ala Arg His Met Pro Ser Val Tyr Val Leu Pro
                325                 330                 335

Pro Ala Pro Glu Glu Leu Ser Leu Gln Glu Trp Ala Ser Val Thr Cys
                340                 345                 350

Leu Val Lys Gly Phe Ser Pro Ala Asp Val Phe Val Gln Trp Leu Gln
            355                 360                 365

Lys Gly Glu Pro Val Ser Ala Asp Lys Tyr Val Thr Ser Ala Pro Val
        370                 375                 380

Pro Glu Pro Glu Pro Lys Ala Pro Ala Ser Tyr Phe Val Gln Ser Val
385                 390                 395                 400

Leu Thr Val Ser Ala Lys Asp Trp Ser Asp Gly Glu Thr Tyr Thr Cys
                405                 410                 415

Val Val Gly His Glu Ala Leu Pro His Thr Val Thr Glu Arg Thr Val
                420                 425                 430

Asp Lys Ser Thr Glu Gly Glu Val Ser Ala Glu Glu Gly Phe Glu
            435                 440                 445

Asn Leu Asn Thr Met Ala Ser Thr Phe Ile Val Leu Phe Leu Leu Ser
        450                 455                 460

Leu Phe Tyr Ser Thr Thr Val Thr Leu Phe Lys Val Lys
465                 470                 475

<210> SEQ ID NO 14
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: chimeric IgM

<400> SEQUENCE: 14

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140
```

Gln Val Ser Trp Leu Arg Glu Gly Lys Gln Val Gly Ser Gly Val Thr
145                 150                 155                 160

Thr Asp Gln Val Glu Thr Val Gln Ser Ser Pro Ile Thr Phe Arg Ala
            165                 170                 175

Tyr Ser Met Leu Thr Ile Thr Glu Arg Asp Trp Leu Ser Gln Asn Val
            180                 185                 190

Tyr Thr Cys Gln Val Glu His Asn Lys Glu Thr Phe Gln Lys Asn Val
        195                 200                 205

Ser Ser Ser Cys Asp Val Ala Pro Pro Ser Pro Ile Gly Val Phe Thr
    210                 215                 220

Ile Pro Pro Ser Phe Ala Asp Ile Phe Leu Thr Lys Ser Ala Lys Leu
225                 230                 235                 240

Ser Cys Leu Val Thr Asn Leu Ala Ser Tyr Asp Gly Leu Asn Ile Ser
                245                 250                 255

Trp Ser Arg Gln Asn Gly Lys Ala Leu Glu Thr His Thr Tyr Phe Glu
            260                 265                 270

Arg His Leu Asn Asp Thr Phe Ser Ala Arg Gly Glu Ala Ser Val Cys
        275                 280                 285

Ser Glu Asp Trp Glu Ser Gly Glu Glu Phe Thr Cys Thr Val Ala His
    290                 295                 300

Ser Asp Leu Pro Phe Pro Glu Lys Asn Ala Val Ser Lys Pro Lys Asp
305                 310                 315                 320

Val Ala Met Lys Pro Pro Ser Val Tyr Leu Leu Pro Pro Thr Arg Glu
                325                 330                 335

Gln Leu Ser Leu Arg Glu Ser Ala Ser Val Thr Cys Leu Val Lys Gly
            340                 345                 350

Phe Ala Pro Ala Asp Val Phe Val Gln Trp Leu Gln Arg Gly Glu Pro
        355                 360                 365

Val Thr Lys Ser Lys Tyr Val Thr Ser Ser Pro Ala Pro Glu Pro Gln
    370                 375                 380

Asp Pro Ser Val Tyr Phe Val His Ser Ile Leu Thr Val Ala Glu Glu
385                 390                 395                 400

Asp Trp Ser Lys Gly Glu Thr Tyr Thr Cys Val Val Gly His Glu Ala
                405                 410                 415

Leu Pro His Met Val Thr Glu Arg Thr Val Asp Lys Ser Thr Glu Gly
            420                 425                 430

Glu Val Ser Ala Glu Glu Gly Phe Glu Asn Leu Asn Thr Met Ala
        435                 440                 445

Ser Thr Phe Ile Val Leu Phe Leu Leu Ser Leu Phe Tyr Ser Thr Thr
    450                 455                 460

Val Thr Leu Phe Lys Val Lys
465                 470

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 15
gaccccaaaa tcagcgaaat                                                   20

```
<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 16
tctggttact gccagttgaa tctg                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Modified ZEN probe sequence

<400> SEQUENCE: 17
accccgcatt acgtttggtg gacc                                              24

<210> SEQ ID NO 18
<211> LENGTH: 4
<212> TYPE: PRT
<213> ORGANISM: Severe acute respiratory syndrome coronavirus 2

<400> SEQUENCE: 18

Arg Arg Ala Arg
1
```

UNGULATE-DERIVED POLYCLONAL IMMUNOGLOBULIN SPECIFIC FOR CORONAVIRUS PROTEIN AND USES THEREOF

CROSS-REFERENCE TO RELATED APPLICATIONS

This application claims priority to U.S. Application No. 63/180,935, filed Apr. 28, 2021, U.S. Application No. 63/144,784, filed Feb. 2, 2021, U.S. Application No. 63/076,121, filed Sep. 9, 2020, and U.S. Application No. 63/072,683, filed Aug. 31, 2020, each of which is incorporated by reference herein in its entirety.

STATEMENT REGARDING GOVERNMENT FUNDING

This invention was made with government support under Medical CBRN Defense Consortium (MCDC) Other Transaction Agreement (OTA) No. W15QKN-16-9-1002 awarded by the United States Government. The government has certain rights in the invention.

INCORPORATION BY REFERENCE OF SEQUENCE LISTING

This application contains a Sequence Listing submitted in electronic format. The sequence listing is provided as a file entitled 436584-001701_SL.txt created on Oct. 25, 2023 and is 83,943 bytes in size. The information in electronic format of the Sequence Listing is incorporated by reference in its entirety.

TECHNICAL FIELD

The invention relates to polyclonal immunoglobulin products for treatment of coronavirus.

BACKGROUND

Immunoglobulin products, such as convalescent plasma, and human-derived and animal-derived immunoglobulins purified from plasma can be used to treat various infectious diseases. Treatment of COVID-19 with convalescent plasma is currently being evaluated and shows promise. Widespread use of this medical intervention would require a sufficient supply of plasma from infected patients; use of human-derived products creates a risk of donor-to-subject transmission of disease. Animal-derived immunoglobulins are known to cause severe hypersensitivity reactions and serum sickness and may be less effective because of structural differences of the antibodies that comprise human and animal immunoglobulins.

There exists, therefore, a need for immunoglobulin products for therapeutic use in patients suffering from or at risk for coronavirus disease.

SUMMARY

The present inventors have developed a polyclonal human immunoglobulin product for treatment of coronavirus disease (e.g., COVID-19) made in ungulates (e.g., bovines) genetically engineered to produce polyclonal human immunoglobulin having a human polypeptide sequence. In addition to demonstrating that the transchromosomic bovine (TcB) system produces immunoglobulins having human polypeptide sequence, the inventors have determined that polyclonal human immunoglobulin produced according to embodiments of the methods described herein may have desirable glycosylation profiles and/or effector functions, in some cases better than analogous human-derived products.

In one aspect, provided herein is an ungulate-derived polyclonal human immunoglobulin composition, comprising a population of human immunoglobulins, wherein the population of human immunoglobulin specifically binds a coronavirus protein selected from coronavirus S protein, coronavirus M protein, coronavirus E protein, or coronavirus Nucleocapsid protein, or a combination thereof.

In some embodiments, the population of human immunoglobulin specifically binds a coronavirus S protein. In some embodiments, the population of human immunoglobulins comprise glycans covalently linked to the human immunoglobulins.

In some embodiments, the glycans comprise at least about 70%, at least about 80%, or at least about 90% N-Glycolylneuraminic acid (NGNA)-bearing glycans.

In some embodiments, 0.5 to 20% of the total immunoglobulin in the composition binds the coronavirus protein.

In another aspect, provided herein is a polyclonal human immunoglobulin composition, produced by immunizing a transgenic ungulate with a coronavirus protein or an antigenic fragment thereof, wherein the composition comprises a population of human immunoglobulins.

In some embodiments, the population of human immunoglobulins specifically binds a coronavirus protein selected from coronavirus S protein, coronavirus M protein, coronavirus E protein, or coronavirus Nucleocapsid protein or an antigenic fragment thereof. In some embodiments, the population of human immunoglobulin specifically binds a coronavirus S protein.

In some embodiments, the glycans comprise at least about 70%, at least about 80%, or at least about 90% N-Glycolylneuraminic acid (NGNA)-bearing glycans.

In some embodiments, the ungulate is a bovine.

In another aspect, provided herein is polyclonal human immunoglobulin composition, comprising a population of human immunoglobulins, wherein the population of human immunoglobulins specifically binds a coronavirus protein optionally selected from coronavirus S protein, coronavirus M protein, coronavirus E protein, or coronavirus Nucleocapsid protein. wherein the population of human immunoglobulins comprise glycans covalently linked to the human immunoglobulins, and wherein the glycans comprise at least about 70%, at least about 80%, or at least about 90% N-Glycolylneuraminic acid (NGNA)-bearing glycans.

In some embodiments, the glycans comprise at least about 70% fucosylated glycans.

In some embodiments, the glycans comprise at least about 80% fucosylated glycans.

In some embodiments, the glycans comprise at least about 90% fucosylated glycans.

In some embodiments, the glycans comprise at least about 94% fucosylated glycans.

In some embodiments, the population of human immunoglobulins binds FcγRI with a $K_D$ of 15 nM or greater.

In some embodiments, the population of human immunoglobulins binds FcγRIIa with a $K_D$ of 500 nM or greater.

In some embodiments, the population of human immunoglobulins binds FcγRIIb/c with a $K_D$ of 1 μM or greater.

In some embodiments, the population of human immunoglobulins binds FcγRIIIa with a $K_D$ of 1 μM or greater.

In some embodiments, the population of human immunoglobulins binds FcγRIIIa with a $K_D$ of 1 nM or greater.

In some embodiments, the population of human immunoglobulins binds one or more human Fc gamma receptors with at most about the same affinity as a reference product.

In some embodiments, the composition is at most about as potent in a CDC assay as a reference product.

In some embodiments, the composition is at most about as potent in a ADCC assay as a reference product.

In some embodiments, the reference product is a human-derived polyclonal immunoglobulin product.

In another aspect, provided herein is method of making polyclonal human immunoglobulin for treatment of coronavirus disease, comprising administering an antigen comprising a coronavirus protein selected from coronavirus S protein, coronavirus M protein, coronavirus E protein, or coronavirus Nucleocapsid protein or an antigenic fragment thereof, or a polynucleotide encoding the antigen, to a transgenic ungulate, wherein the transgenic ungulate comprises a genome comprising a human immunoglobulin locus or an artificial chromosome comprising a human immunoglobulin locus, wherein the transgenic ungulate produces a population of human immunoglobulins that specifically binds the coronavirus S protein.

In some embodiments, administering the antigen or polynucleotide encoding the antigen 3, 4, 5, or more times.

In some embodiments, the method comprises collecting serum or plasma from the transgenic ungulate.

In some embodiments, the serum or plasma comprises a population of fully human immunoglobulins.

In some embodiments, the coronavirus is a SARS-CoV2.

In some embodiments, the antigen comprises a recombinant ectodomain of the coronavirus S protein.

In some embodiments, the recombinant ectodomain comprises one or more amino acid substitutions of a basic amino acid in the S1/S2 cleavage site (residues 682 to 685) to a non-basic residue.

In some embodiments, the recombinant ectodomain comprises one or more amino acid substitutions that stabilize the recombinant ectodomain.

In some embodiments, the one or more amino acid substitutions that stabilize the recombinant ectodomain comprise K986P and/or V986P.

In some embodiments, the method comprises administering a vaccine prime comprising a polynucleotide encoding the coronavirus S protein.

In some embodiments, the polynucleotide encoding the coronavirus S protein is a plasmid DNA molecule (pDNA).

In some embodiments, the method comprises co-administering an adjuvant comprising Montanide ISA-206 and/or Quil A at the site of vaccine prime administration.

In some embodiments, the antigen is administering in a pharmaceutical composition comprising Montanide ISA-206 and/or Quil A.

In some embodiments, the method comprises a) administering a first vaccine prime comprising the polynucleotide encoding the coronavirus S protein; b) administering a second vaccine prime comprising a polynucleotide encoding the coronavirus S protein, three to four weeks later; c) administering a first antigen comprising the recombinant ectodomain of the coronavirus S protein, four weeks later d) administering a second antigen comprising the recombinant ectodomain of the coronavirus S protein, four weeks later; and e) administering a third antigen comprising the recombinant ectodomain of the coronavirus S protein, four weeks later.

In some embodiments, the method comprises purifying the human immunoglobulin to produce an ungulate-derived polyclonal immunoglobulin composition according to the disclosure.

In another aspect, provided herein is pharmaceutical composition, comprising the composition as disclosed herein and optionally one or more pharmaceutically acceptable excipients.

In another aspect, provided herein is method of treating or preventing coronavirus disease (COVID) in a subject suffering from or at risk for COVID, comprising administering an effective amount of a composition as disclosed herein or the pharmaceutical composition as disclosed herein to the subject.

Additional embodiments, features, and advantages of the invention will be apparent from the following detailed description and through practice of the invention.

BRIEF DESCRIPTION OF THE DRAWINGS

FIG. 1A shows a flow of the isHAC and isKcHACΔ vector construction. The bovinizing vector pCC1BAC-isHAC is a BAC-based one (backbone is pCC1BAC vector), consisting of 10.5 kb and 2 kb of genomic DNA as a long and short arm, respectively, 9.7 kb of the bovine genomic DNA covering the bovine $I_{\gamma1}$-$S_{\gamma1}$ and its surrounding region to replace the human corresponding 6.8 kb of $I_{\gamma1}$-$S_{\gamma1}$ region, the chicken β-actin promoter-driven neo gene flanked by FRT sequence and DT-A gene. After the targeted bovinization, the neo cassette is removed by FLP introduction.

FIG. 1B shows detailed information on the targeting vector pCC1BAC-isHAC. The 2 kb of Afe I-Bam HI fragment and 10.5 kb of Apa I-Hpa I fragment for a short arm and long arm were obtained from clone h10 and clone h18/h20, respectively, derived from λ phage genomic library constructed from CHO cells containing the κHAC by screening using a probe around the human $I_{\gamma1}$-$S_{\gamma1}$ region. The 9.7 kb fragment (5' end through Bsu36 I) was obtained from clone b42 derived from the λ phage bovine genomic library.

FIG. 1C shows senotyping of the bovinized $I_{\gamma1}$-$S_{\gamma1}$ region. Five sets of genomic PCR were implemented, as indicated. iscont1-F1/R1 is a positive PCR specific to the homologous recombination. iscont1-F1×hIgG1-R10 is a negative PCR that is prohibited by the presence of the neo cassette. isHAC-Sw-dig-F5/R3 and isHAC-TM-dig-F3/R2 are for structural integrity check of their corresponding region, digested by Bam HI+Pvu II and Age I, Sma I or Pvu II, respectively. bNeo 5'-R×bIgG1-5'-seq-R6 is to confirm the presence of FRT sequence.

FIG. 1D shows genotyping after the FLP-FRT deletion of the neo cassette.

FIG. 1E shows extensive genomic PCR for genotyping of the isHAC vector. Location of each genomic PCR primer pair is depicted in relation to the isHAC vector structure.

FIG. 1F shows CGH analysis among three different CHO clones containing the isHAC vector. DNA from is C1-133 was used as a reference. There was no apparent structural difference of the isHAC among the three cell lines.

FIG. 1G shows extensive genomic PCR for genotyping of the isKcHACΔ vector. Location of each genomic PCR primer pair is depicted in relation to the isKcHACΔ vector structure.

FIG. 1H shows CGH analysis among three different CHO clones containing the isKcHACΔ vector. DNA from isKCDC15-8 was used as a reference. There was no apparent structural difference of the isKcHACΔ among the three cell lines.

(FIG. 8A) three lots of SAB-185 pAbs and a negative control were tested for neutralization of wild-type and (FIG. 8B) mutant VSV-SARS-CoV-2 (n=4). Error bars represent the SEM. Data are representative of four independent experiments. FIG. 8C is a heat map of the same data.

FIG. 9A, SAB-185 pAbs were tested for neutralizing activity against VSV-SARS-CoV-2 using an MOI of 1. SAB-185 pAbs were purified from transchromosomic (Tc) bovines that were immunized with spike protein antigens, and validated by plaque reduction neutralization test (PRNT) titers against SARS-CoV-2. Data are plotted in FIG. 9A: Error bars represent the SEM. Data are representative of four independent experiments. FIG. 9B, plaque assays were performed to isolate the VSV-SARS-CoV-2-S escape mutant on Vero E6 TMPRSS2 cells in the present of the indicated pAb in the overlay. The concentration of SAB-185 pAbs added in the overlay completely inhibited viral infection (See FIGS. 9A-9B). Escape mutants are found in the control mAb experiment (shown by arrows) while no escape mutants occur in with SAB-185 pAbs (FIG. 9B). This indicates that SAB-185 as pAb is superior to mAb against escape mutants. Representative images of eight independent experiments are shown.

DETAILED DESCRIPTION

Figure 1A:
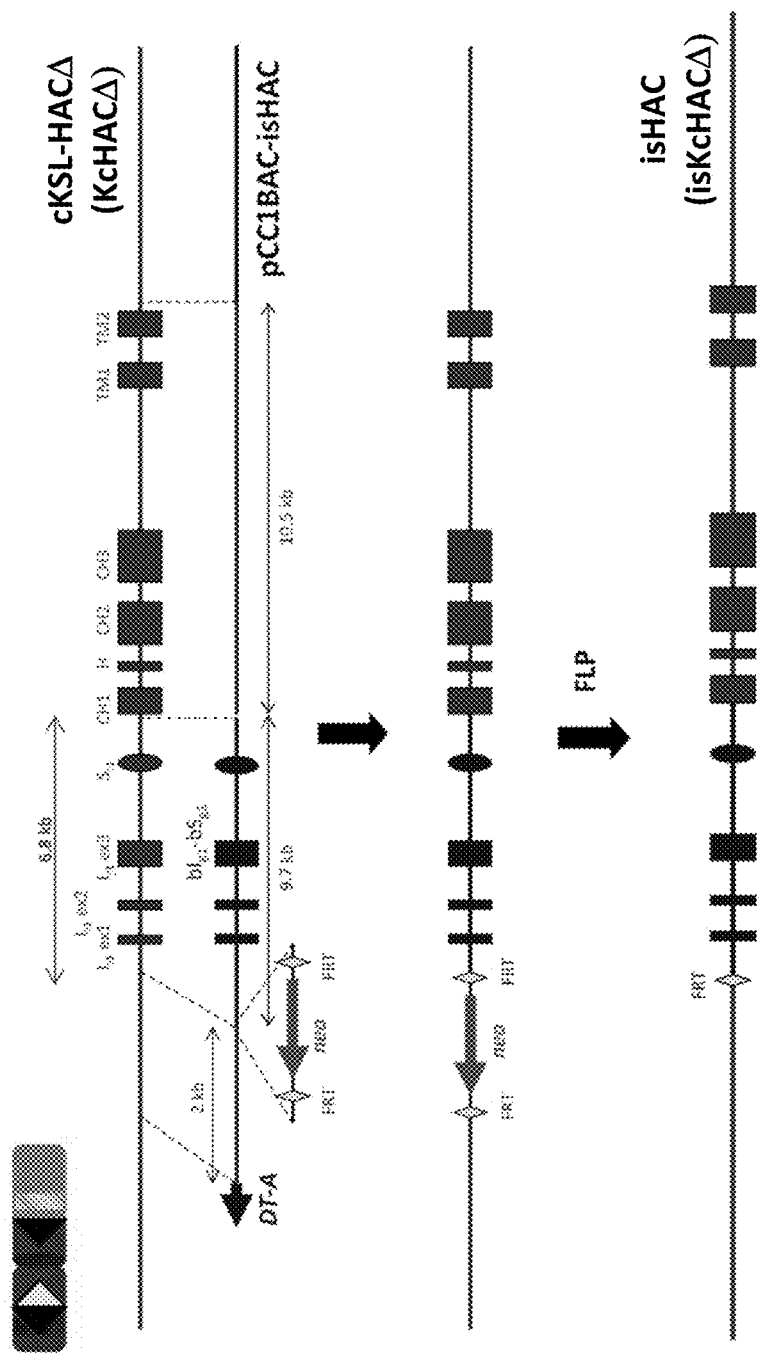
FIGS. 1A-1H show construction of the isHAC and isKcHACΔ vectors.
Figure 1B:
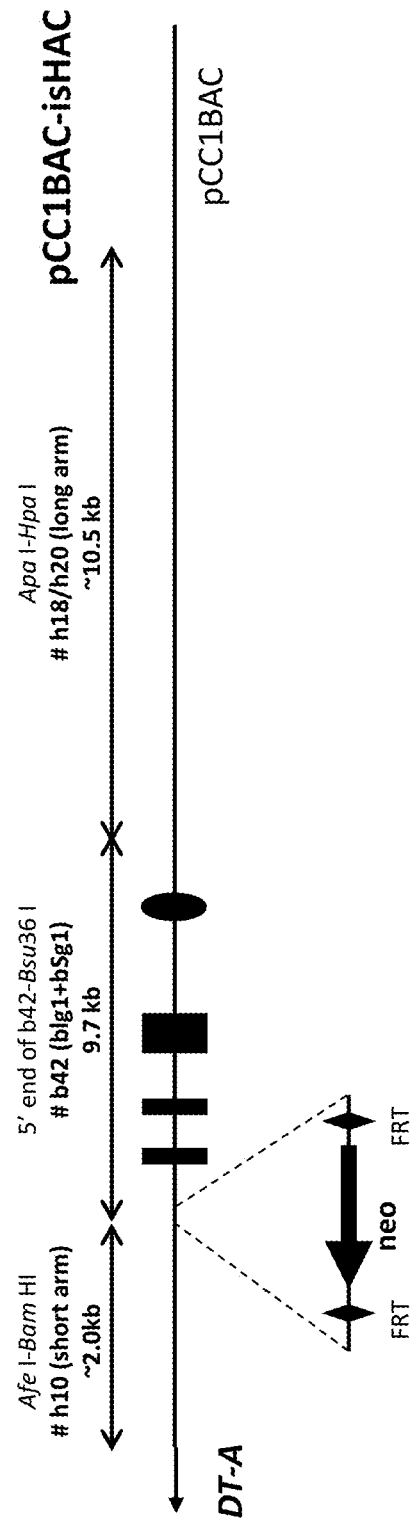
Figure 1C:
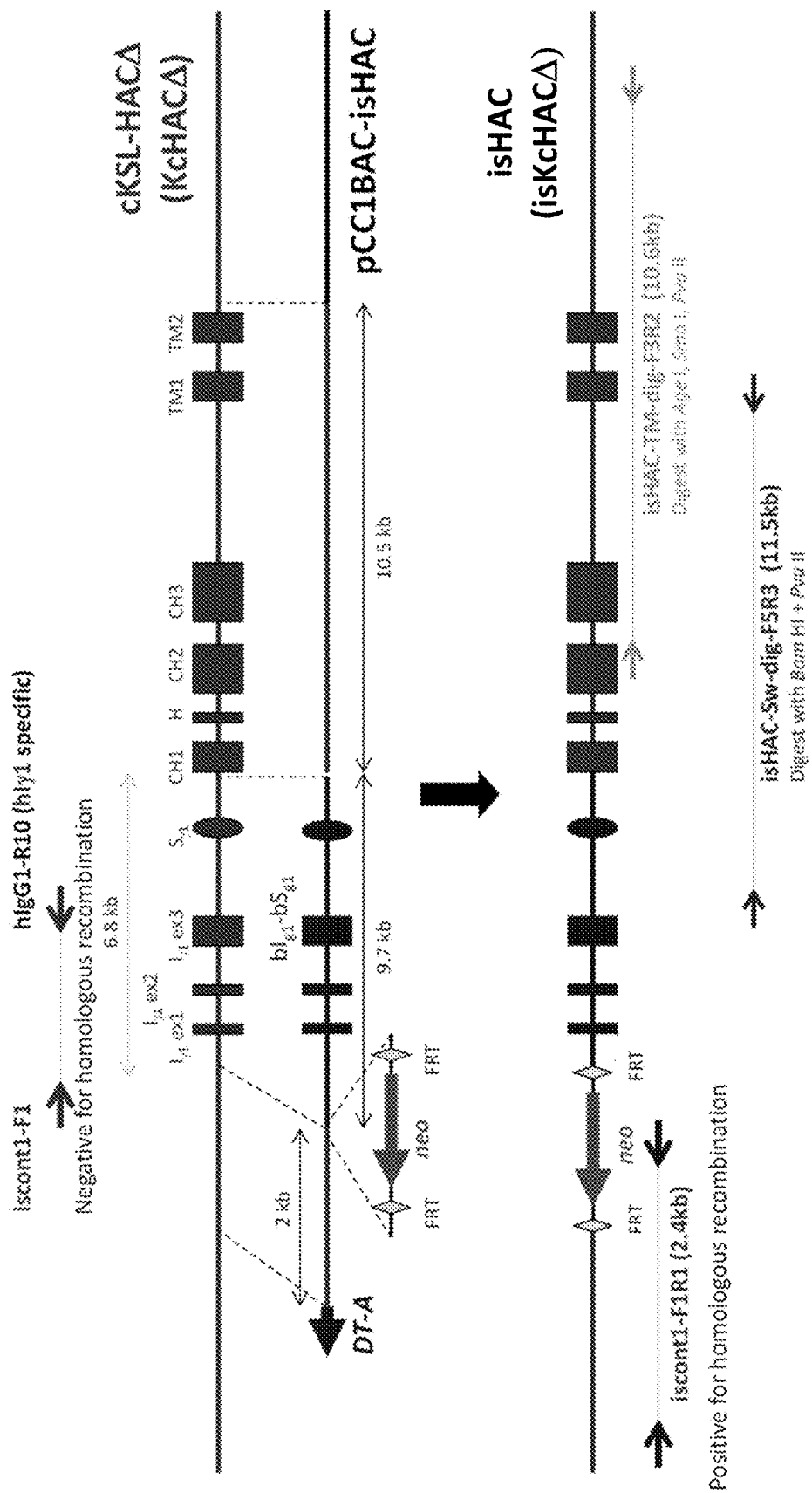
Figure 1D:
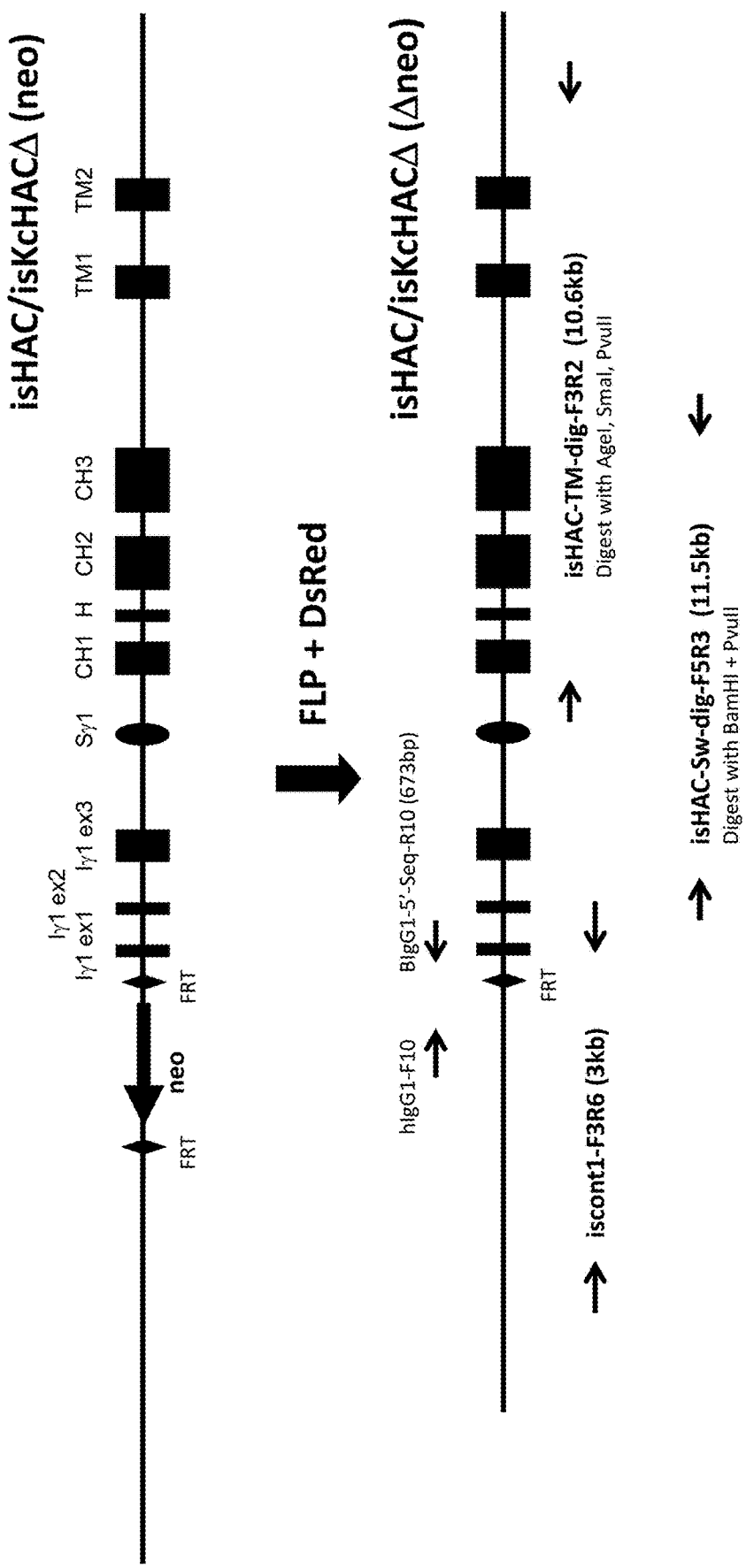
Figure 1E:
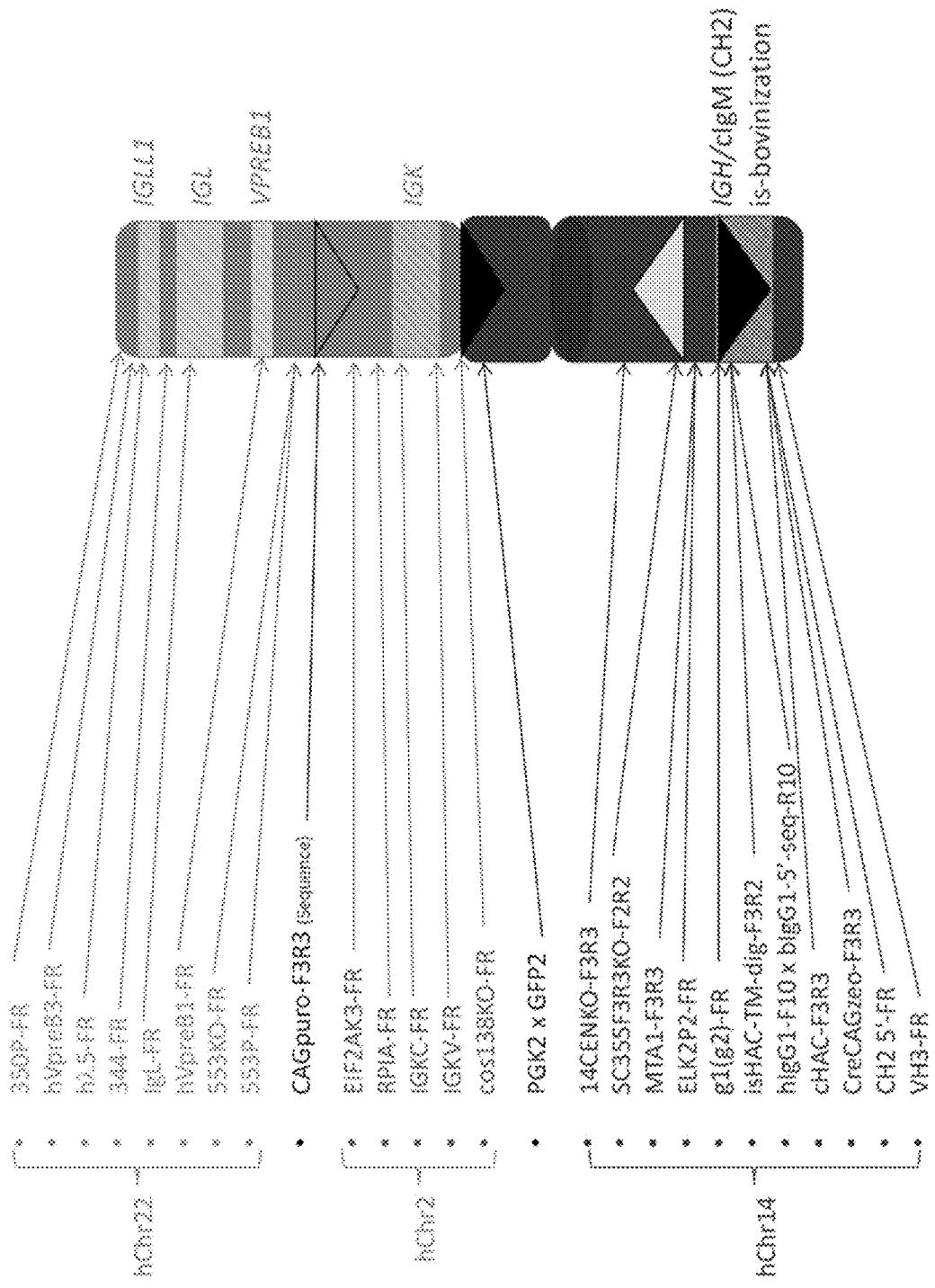
Figure 1F:
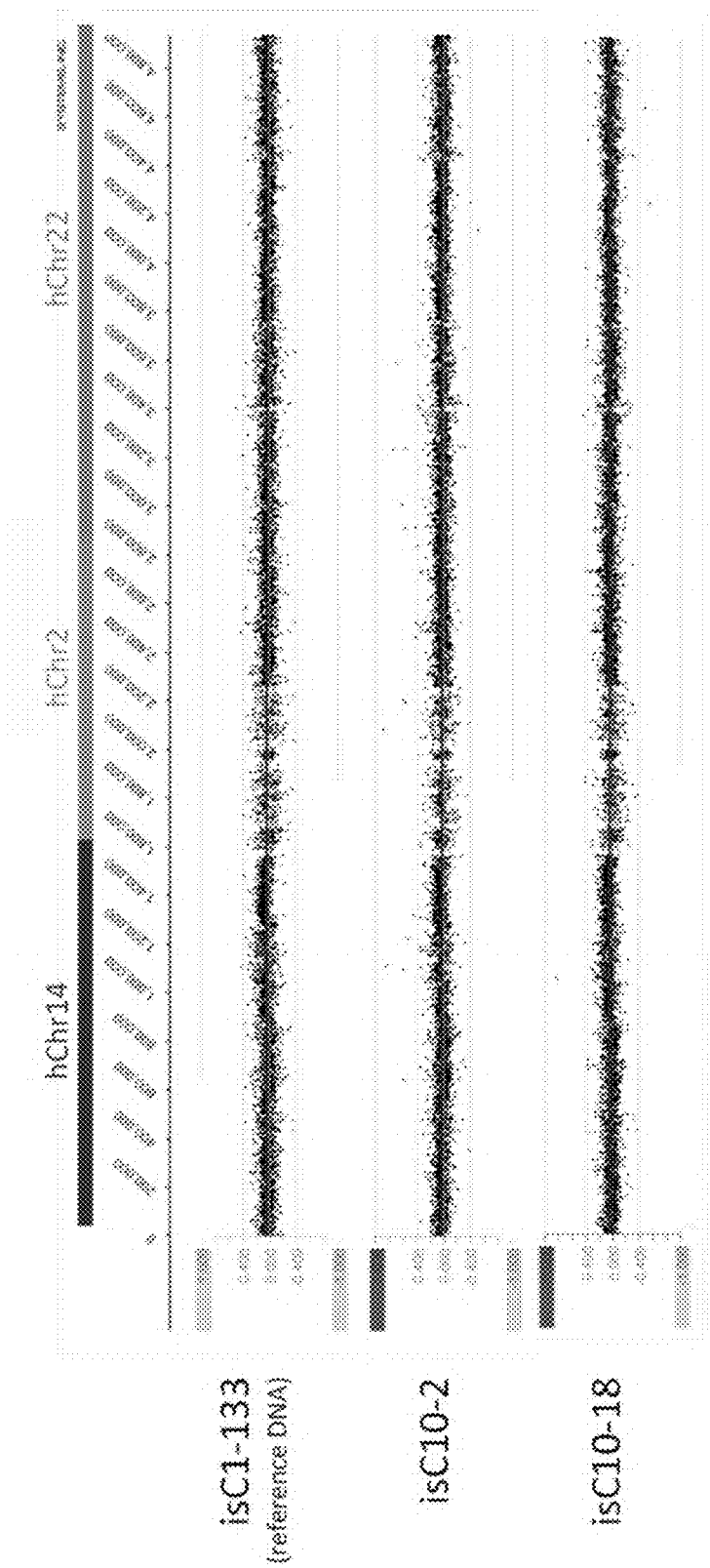
Figure 1G:
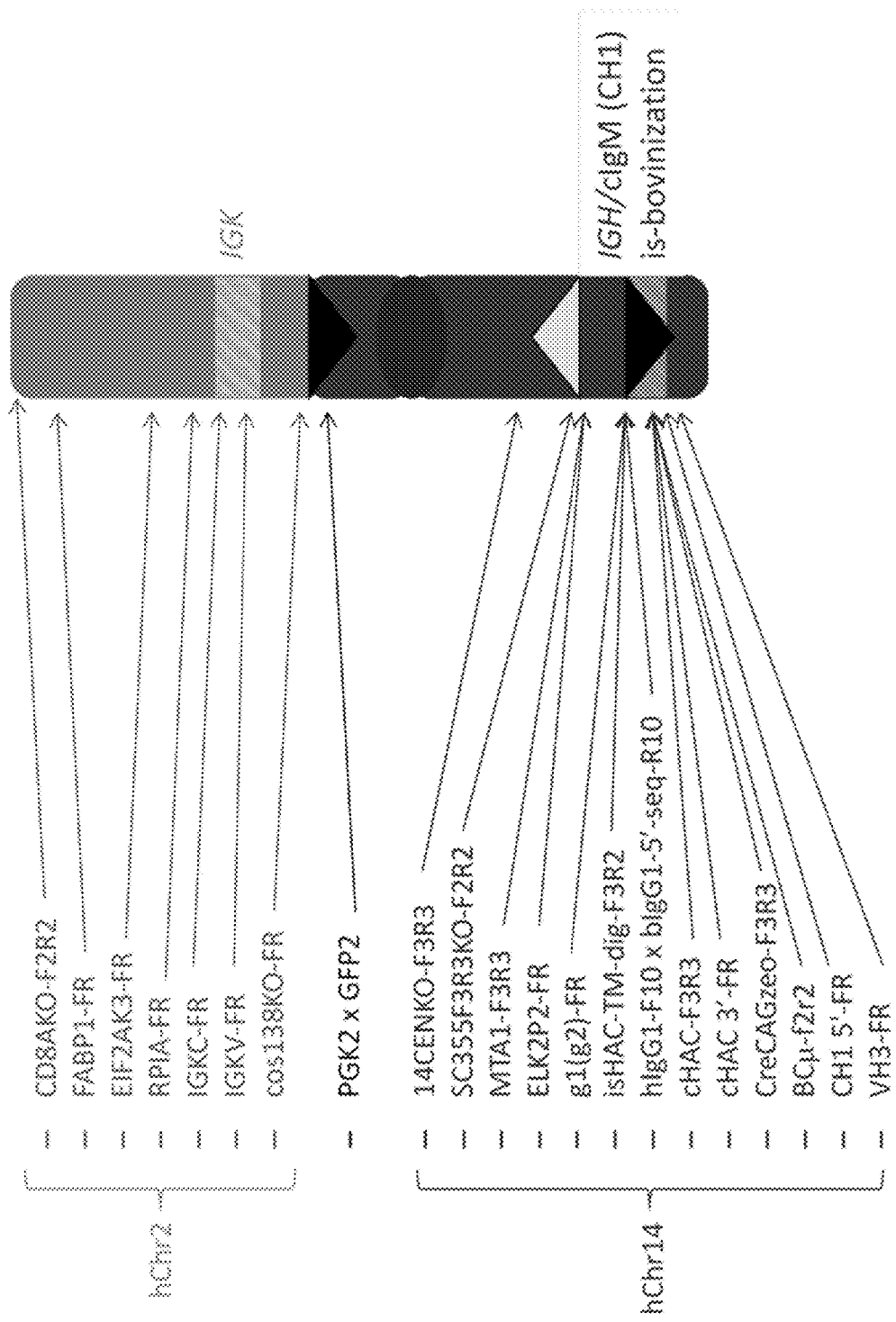
Figure 1H:
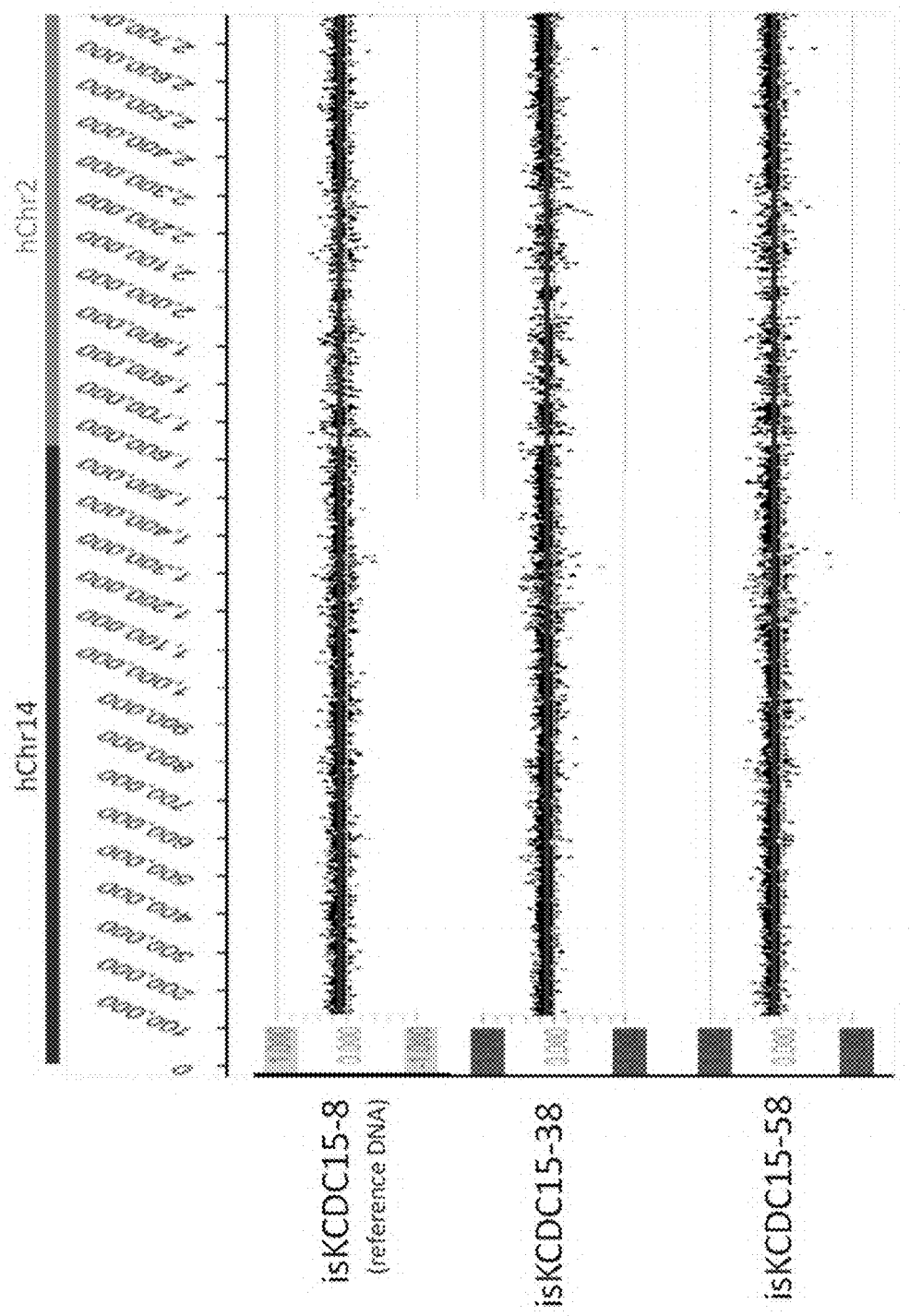
Figure 2A:
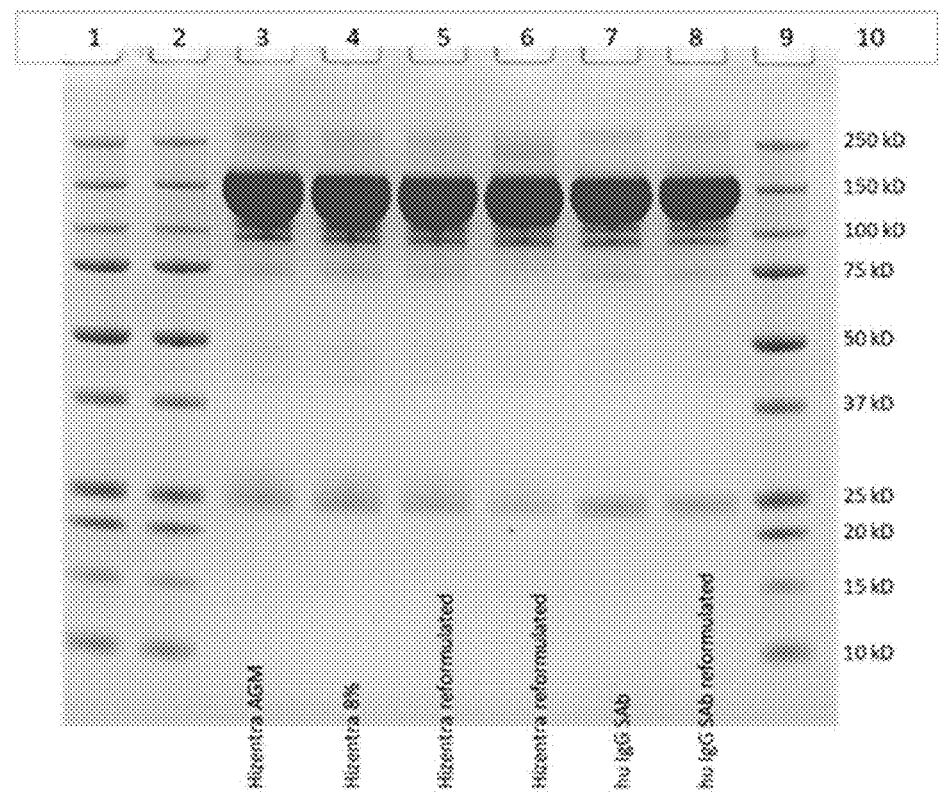
FIG. 2A shows non-reducing gel electrophoresis characterization of a TcB-derived product compared to a sterilized solution made from human plasma (Hizentra®).
Figure 2B:
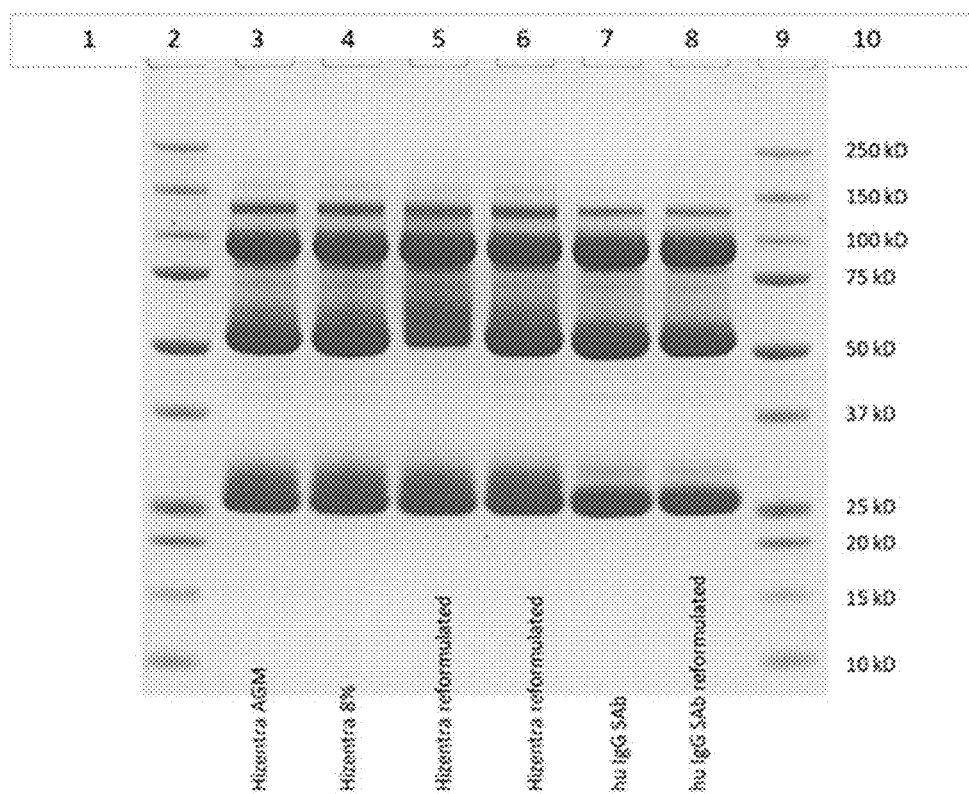
FIG. 2B shows non-reducing gel electrophoresis characterization of a TcB-derived product compared to a sterilized solution made from human plasma (Hizentra®).
Figure 3:
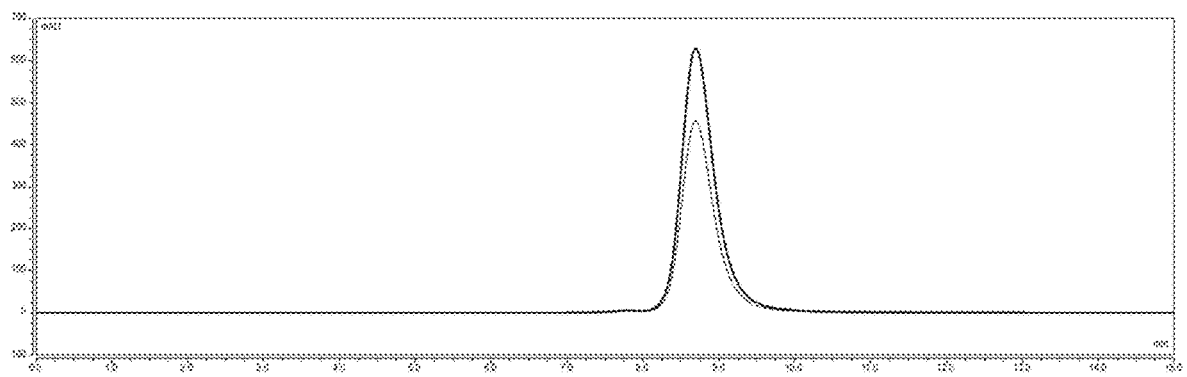
FIG. 3 shows a size exclusion chromatogram of TcB-derived product.

The present inventors have developed a human immunoglobulin product for coronavirus disease that overcomes limitations of human- and animal-derived immunoglobulin product. Transgenic animals with the endogenous Ig locus replaced by a human artificial chromosome encoding a human Ig locus express fully human polyclonal antibodies. Immunization of such a transgenic animal with a recombinant coronavirus spike (S) protein, or an antigenic fragment thereof, and/or with a polynucleotide encoding the antigen, generates polyclonal immunoglobulin with yield, purity, and antigen specificity that enable use of this product in medical applications. Various embodiments of the invention are provided in the description that follows.

Definitions

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," "below," and words of similar import, when used in this application, shall refer to this application as a whole and not to any particular portions of the application.

The term "ungulate" refers to any suitable ungulate, including but not limited to bovine, pig, horse, donkey, zebra, deer, oxen, goats, sheep, and antelope.

The term "transgenic" means the cells of the ungulate comprise one or more polynucleotides encoding exogenous gene(s) (e.g. an immunoglobulin locus). Such as polynucleotide may be a portion of an artificial chromosome. Alternatively, or in addition to an artificial chromosome, one or more polypolynucleotides encoding exogenous gene(s) may be integrated into the genome of the cells of the ungulate.

The terms "polyclonal" or "polyclonal serum" or "polyclonal plasma" or "polyclonal immunoglobulin" refer to a population of immunoglobulins having shared constant regions but diverse variable regions. The term polyclonal does not, however, exclude immunoglobulins derived from a single B cell precursor or single recombination event, as may be the case when a dominant immune response is generated. A polyclonal serum or plasma contains soluble forms (e.g., IgG) of the population of immunoglobulins. The term "purified polyclonal immunoglobulin" refers to polyclonal immunoglobulin purified by serum or plasma. Methods of purifying polyclonal immunoglobulin include, without limitation, caprylic acid fractionation and adsorption with red blood cells (RBCS).

A "population" of immunoglobulins refers to immunoglobulins having diverse sequences, as opposed to a sample having multiple copies of a single immunoglobulin. Similarly stated, the term population excludes immunoglobulins secreted from a single B cell, plasma cell, or hybridoma in culture, or from a host cells transduced or transformed with recombinant polynucleotide(s) encoding a single pair of heavy and light chain immunoglobulin sequences.

The term "immunoglobulin" refers to a protein complex at least two heavy and at least two light chains in 1:1 ratio, including any of the five classes of immunoglobulin—IgM, IgG, IgA, IgD, IgE. In variations, the immunoglobulin is engineered in any of various ways known in the art or prospectively discovered, including, without limitation, mutations to change glycosylation patterns and/or to increase or decrease complement dependent cytotoxicity.

An immunoglobulin is "fully human or substantially human" when the protein sequence of the immunoglobulin is sufficiently similar to the sequence of a native human immunoglobulin that, when administered to a subject, the immunoglobulin generates an anti-immunoglobulin immune response similar to, or not significantly worse, that the immune reaction to native human immunoglobulin. A fully human immunoglobulin will comprise one or more substitutions, insertions, to deletions in variable regions, consistent with recombination, selection, and affinity maturation of the immunoglobulin sequence. In variations, the fully human or substantially human immunoglobulin is engineered in any of various ways known in the art or prospectively discovered, including, without limitation, mutations to change glycosylation patterns and/or to increase or decrease complement dependent cytotoxicity.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. Any of the compositions of the present disclosure may be isolated compositions.

The percentage of an immunoglobulin (e.g., immunoglobulin that specifically binds human coronavirus) "by mass of total immunoglobulin" refers to the concentration of a target immunoglobulin population divided by the concentration of total immunoglobulin in a sample, multiplied by 100. The concentration of target immunoglobulin can be determined by, for example, affinity purification of target immunoglobulin (e.g. on affinity column comprising coronavirus or thymocyte cell membranes) followed by concentration determination.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation. Alternatively, "about" can mean plus or minus a range of up to 20%, up to 10%, or up to 5%.

The terms "immunization" and "immunizing" refer to administering a composition to a subject (e.g., a transgenic ungulate) in an amount sufficient to elicit, after one or more administering steps, a desired immune response (e.g., a polyclonal immunoglobulin response specific to coronavirus). Administration may be by intramuscular injection, intravenous injection, intraperitoneal injection, or any other suitable route. Immunization may comprise between one and ten, or more administrations (e.g. injections) of the composition, such as 1, 2, 3, 4, 5, 6, 7, 8, 9, 10, or more administrations. The first administration may elicit no detectable immune response as generally each subsequence administration will boost the immune response generated by prior administrations.

The term "target antigen" refers to any antigen use to elicit a desired immune response. The target antigen used to generate an immunoglobulin product for coronavirus disease may be recombinant spike (S) protein or an antigen fragment thereof, or nucleic acid that encodes such proteins (e.g. RNA, linear DNA, or plasmid DNA).

The term "purify" refers to separating a target cell or molecule (e.g. a population of immunoglobulins) from other substances present in a composition. Immunoglobulins may be purified by fractionation of plasma, by affinity (e.g. protein A or protein G binding, or other capture molecule), by charge (e.g. ion-exchange chromatography), by size (e.g. size exclusion chromatograph), or otherwise. Purifying a population of immunoglobulins may comprise treating a composition comprising the population of immunoglobulins with one or more of acids, bases, salts, enzymes, heat, cold, coagulation factors, or other suitable agents. Purifying may further include adsorption of a composition comprising a target cell or molecule and an impurity onto non-target cells or molecules (e.g., red blood cells) to partially or completely remove the impurity. Purifying may further include pretreatment of serum or plasma, e.g., caprylic acid fractionation.

The terms "treating" and "treatment" refer to one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "pharmaceutically acceptable" means biologically or pharmacologically compatible for in vivo use in animals or humans, and can mean approved by a regulatory agency of the Federal or a state government or listed in the U.S. Pharmacopeia or other generally recognized pharmacopeia for use in animals, and more particularly in humans.

The term "hyperimmunized" refers to immunization regimen that generates an immune response to the subject greater than required to produce a desired titer (e.g. a binding titer) after dilution of the immunoglobulin produced by the subject. For example, if a desired titer is 1:100, one may hyperimmunize an animal by a prime immunization followed by one, two, three or more boost immunizations to produce a 1:1,000 titer, or greater titer, in the subject—so that immunoglobulin produced by the subject may be diluted in the production of a biotherapeutic in order to give a desired titer in the biotherapeutic.

An immunoglobulin is "specific to" or "specifically binds" (used interchangeably herein) to a target (e.g., coronavirus or a thymocyte antigen) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An immunoglobulin "specifically binds" to a particular protein or substance if it binds with greater affinity, avidity, more readily, and/or with greater duration than it binds to alternative particular protein or substance. For example, an immunoglobulin that specifically or preferentially binds to coronavirus S protein is an immunoglobulin that binds coronavirus S protein with greater affinity, avidity, more readily, and/or with greater duration than it binds to other proteins. An immunoglobulin that specifically binds to a first protein or substance may or may not specifically or preferentially bind to a protein cell or substance. As such, "specific binding" does not necessarily require (although it can include) exclusive binding. Generally, but not necessarily, reference to binding means specific binding.

The term "HAC vector" means a vector which comprises at least a human chromosome-derived centromere sequence, a telomere sequence, and a replication origin, and may contain any other sequences as desired for a given application. When present in a host cell, the HAC vector exists independently from a host cell chromosome in the nucleus. Any suitable methods can be used to prepare HAC vectors and to insert nucleic acids of interest into the HAC, including but not limited to those described in the examples that follow. The HAC vector is a double stranded DNA vector, as is known to those of skill in the art.

Embodiments

Provided are methods of making a human polyclonal immunoglobulin for treatment of coronavirus disease, comprising administering an antigen comprising a coronavirus S protein or antigenic fragment thereof, or a polynucleotide encoding the antigen, to a transgenic ungulate, wherein the transgenic ungulate comprises a genome comprising a human immunoglobulin locus or an artificial chromosome comprising a human immunoglobulin locus, wherein the transgenic ungulate produces a population of human immunoglobulins that specifically binds the coronavirus S protein.

In a variation, non-human coronavirus S protein, or a polynucleotide encoding it, is used (e.g., coronavirus of a domesticated animal such as a dog, cat, sheep, etc.). The transgenic ungulate may in such cases comprise an artificial chromosome encoding an Ig locus of the non-human species such that antibodies of that species are generated.

In some embodiments, the coronavirus S protein, or a polynucleotide encoding it (that is, "the antigen") is administered before, during, or after administration of one or more adjuvants. In some embodiments, the antigen and one or more adjuvants are administered together in a single composition, comprising optionally one or more pharmaceutically acceptable excipients.

Illustrative adjuvants include an aluminum salt adjuvant, an oil in water emulsion (e.g. an oil-in-water emulsion comprising squalene, such as MF59 or AS03), a TLR7 agonist (such as imidazoquinoline or imiquimod), or a combination thereof. Suitable aluminum salts include hydroxides (e.g. oxyhydroxides), phosphates (e.g. hydroxyphosphates, orthophosphates), (e.g. see chapters 8 & 9 of Vaccine Design. (1995) eds. Powell & Newman. ISBN: 030644867X. Plenum), or mixtures thereof. Further illustrative adjuvants include, but are not limited to, Adju-Phos, Adjumerlm, albumin-heparin microparticles, Algal Glucan, Algammulin, Alum, Antigen Formulation, AS-2 adjuvant, autologous dendritic cells, autologous PBMC, Avridine™, B7-2, BAK, BAY R1005, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod, ImmTher™, Immunoliposomes Containing Antibodies to Costimulatory Molecules, Interferon-gamma, Interleukin-1 beta, Interleukin-12, Interleukin-2, Interleukin-7, ISCOM(s)™, Iscoprep 7.0.3™, MONTANIDE™ ISA-25, Keyhole Limpet Hemocyanin, Lipid-based Adjuvant, Liposomes, Loxoribine, LT(R192G), LT-OA or LT Oral Adjuvant, LTK63, LTK72, MF59, MONTANIDE ISA 51, MONTANIDE ISA 720, MPL.™, MPL-SE, MTP-PE, MTP-PE Liposomes, Murametide, Murapalmitine, NAGO, nCT native Cholera Toxin, Non-Ionic Surfactant Vesicles, non-toxic mutant E1 12K of Cholera Toxin mCT-E112K, p-Hydroxybenzoique acid methyl ester, pCIL-10, pCIL12, pCMVmCAT1, pCMVN, Peptomer-NP, Pleuran, PLG, PLGA, PGA, and PLA, Pluronic L121, PMMA, PODDS™, Poly rA: Poly rU, Polysorbate 80, Protein Cochleates, QS-21, Quadri A saponin, Quil-A, ISA-25/Quil-A, Rehydragel HPA, Rehydragel LV, RIBI, Ribilike adjuvant system (MPL, TMD, CWS), S-28463, SAB-adj-1, SAB-adj-2, SAF-1, Sclavo peptide, Sendai Proteoliposomes, Sendai-containing Lipid Matrices, Span 85, Specol, Squalane 1, Squalene 2, Stearyl Tyrosine, Tetanus toxoid (TT), Theramide™, Threonyl muramyl dipeptide (TMDP), Ty Particles, and Walter Reed Liposomes.

The immunization may be carried out by administering the antigen with, for example, a complete Freund's adjuvant or an appropriate adjuvant such as an aluminum hydroxide gel, and pertussis bacteria vaccine, subcutaneously, intravenously, or intraperitoneally into a transgenic ungulate. In one embodiment, the immunization comprises hyperimmunization. In various embodiments, the antigen is administered once to 10 times every 1 to 4 weeks after the first administration. After 1 to 14 days from each administration, blood is collected from the animal to measure the antibody value of the serum.

In some embodiments, the antigen is administered 3, 4, 5, 6 or more times. Administration of the human coronavirus may be performed, e.g., every 1-2 weeks, 2-3 weeks, 3-4 weeks, 4-5 weeks, 5-6 weeks, or 6-7 weeks, or longer intervals, e.g., every 1 week, 2 weeks, 3 weeks, 4 weeks, 5 weeks or 6 weeks. After each immunization, serum and/or plasma may be harvested from the transgenic ungulate one or more times. For example, the method may be including performing controls bleeds two or three times at intervals about 7-14 days.

In some embodiments, the antigen used to generate an immunoglobulin product for coronavirus disease may be—rather than coronavirus S protein—any other antigenic portion of the coronavirus, produced by isolation from the living virus or by recombinant methods, or nucleic acids that encoding such antigenic portions of the coronavirus (e.g. RNA, linear DNA, or plasmid DNA).

In embodiments of the methods of the disclosure, the genome of the transgenic ungulate comprises a human immunoglobulin locus. Illustrative methods are provided in U.S. Pat. Nos. 9,902,970; 9,315,824; 7,652,192; and 7,429,690; and 7,253,334, the disclosure of which are incorporated by reference herein for all purposes. Further illustrative methods are provided by Kuroiwa, Y., et al. (2009) *Nat Biotechnol.* 27(2):173-81, and Matsushita et al. (2015) *PLoS ONE* 10(6):e0130699.

The disclosure provides a human artificial chromosome (HAC) vector comprising genes encoding:
  (a) one or more human antibody heavy chains, wherein each gene encoding an antibody heavy chain is operatively linked to a class switch regulatory element;
  (b) one or more human antibody light chains; and
  (c) one or more human antibody surrogate light chains, and/or an ungulate-derived IgM heavy chain constant region;
  wherein at least one class switch regulatory element of the genes encoding the one or more human antibody heavy chains is replaced with an ungulate-derived class switch regulatory element.

The HAC vectors of the disclosure can be used, for example, for large-scale production of fully human antibodies by transgenic animals, as described for the methods of the invention. The HAC vector of the present disclosure comprises one or more genes encoding a human antibody heavy chain. Any human antibody heavy chain or combinations of human antibody heavy chains in combination may be encoded by one or more nucleic acids on the HAC. In various embodiments, 1, 2, 3, 4, 5, 6, 7, 8, or all 9 of human antibody heavy chains IgM, IgG1, IgG2, IgG3, IgG4, IgA1, IgA2, IgE and IgD may be encoded on the HAC in one or more copies. In one embodiment, the HAC comprises a human IgM antibody heavy chain encoding gene, alone or in combinations with 1, 2, 3, 4, 5, 6, 7, or the other 8 human antibody chain encoding genes. In one preferred embodiment, the HAC comprises a gene encoding at least a human IgG1 antibody heavy chain; in this embodiment, it is further preferred that the HAC comprises a gene encoding a human IgM antibody heavy chain or a gene encoding a human IgM antibody heavy chain that has been chimerized to encode an ungulate-derived IgM heavy chain constant region (such as a bovine heavy chain constant region). In another embodiment, the HAC comprises a gene encoding at least a human IgA antibody heavy chain; in this embodiment, it is further preferred that the HAC comprises a gene encoding a human IgM antibody heavy chain or a gene encoding a human IgM antibody heavy chain that has been chimerized to encode an ungulate-derived IgM heavy chain constant region (such as a bovine heavy chain constant region). In another preferred embodiment, the HAC comprises genes encoding all 9 antibody heavy chains, and more preferably where the gene encoding a human IgM antibody heavy chain has been chimerized to encode an ungulate-derived IgM heavy chain constant region. In another embodiment, the HAC may comprise a portion of human chromosome 14 that encodes the human antibody heavy chains. The variable region genes and the constant region genes of the human antibody heavy chain form a cluster and the human heavy chain locus is positioned at 14q32 on human chromosome 14. In one embodiment, the region of human chromosome 14 inserted in the HAC comprises the variable region and the constant region of the human antibody heavy chains from the 14q32 region of human chromosome 14.

In some embodiments of the HAC vectors of the present disclosure, at least one class switch regulatory element of the human antibody heavy chain encoding nucleic acid is replaced with an ungulate-derived class switch regulatory element. The class switch regulatory element refers to nucleic acid which is 5' to an antibody heavy chain constant region. Each heavy chain constant region gene is operatively linked with (i.e. under control of) its own switch region, which is also associated with its own I-exons. Class switch regulatory elements regulate class switch recombination and determine Ig heavy chain isotype. Germline transcription of each heavy chain isotype is driven by the promoter/enhancer elements located just 5' of the I-exons and those elements are cytokine or other activator-responsive. In a simple model of class switch, the specific activators and/or cytokines induce each heavy chain isotype germline transcription from its class switch regulatory element (i.e., activator/cytokine-responsive promoter and/or enhancer). Class switch is preceded by transcription of I-exons from each Ig heavy (IGH)

locus-associated switch region. As each heavy chain constant region gene is linked with its own switch region.

Any suitable ungulate-derived class switch regulatory element can be used. For example, the human heavy chain gene isotypes listed below has the following class switch regulatory elements:

IgM: Iμ-Sμ,
IgG1: Iγ1-Sγ1,
IgG2: Iγ2-Sγ2,
IgG3: Iγ3-Sγ3,
IgG4: Iγ4-Sγ4,
IgA1: Iα1-Sα1,
IgA2: Iα2-Sα2, and
IgE: Iε-Sε.

In various embodiments, 1, more than 1, or all of the human antibody heavy chain genes on the HAC have their class switch regulatory element replaced with an ungulate-derived class switch regulatory element, including but not limited to ungulate IμSμ, Iγ-Sγ, Iα-Sα, or Iε-Sε, class switch regulatory elements. In one embodiment, an Iγ1-Sγ1 human class switch regulatory element for human IgG1 heavy chain encoding nucleic acid on the HAC (such as that in SEQ ID NO: 1) is replaced with an ungulate Iγ1-Sγ1 class switch regulatory element. Exemplary ungulate Iγ1-Sγ1 class regulatory switch elements include a bovine IgG1 Iγ1-Sγ1 class switch regulatory element (SEQ ID NO: 2), a horse Iγ1-Sγ1 class switch regulatory element (SEQ ID NO: 3), and a pig Iγ1-Sγ1 class switch regulatory element (SEQ ID: 4). However, it is not necessary to replace the human class switch regulatory element with an ungulate class switch regulatory element from the corresponding heavy chain isotype. Thus, for example, an Iγ3-Sγ3 human class switch regulatory element for human IgG3 heavy chain encoding nucleic acid on the HAC can be replaced with an ungulate Iγ1-Sγ1 class switch regulatory element. As will be apparent to those of skill in the art based on the teachings herein, any such combination can be used in the HACs of the disclosure.

In another embodiment, the HAC comprises at least one ungulate enhancer element to replace an enhancer element associated with one or more human antibody heavy chain constant region encoding nucleic acids on the HAC. There are two 3' enhancer regions (Alpha 1 and Alpha 2) associated with human antibody heavy chain genes. Enhancer elements are 3' to the heavy chain constant region and also help regulate class switch. Any suitable ungulate enhancer can be used, including but not limited to 3'Eα enhancers. Non-limiting examples of 3' Eα enhancers that can be used include 3'Eα, 3'Eα1, and 3'Eα2. Exemplary 3'Eα enhancer elements from bovine that can be used in the HACs and replace the human enhancer include, but are not limited to bovine HS3 enhancer (SEQ ID NO: 5), bovine HS12 enhancer (SEQ ID NO: 6), and bovine enhancer HS4. This embodiment is particularly preferred in embodiments wherein the HAC comprises the variable region and the constant region of the human antibody heavy chains from the 14q32 region of human chromosome 14.

The HAC vectors of the present disclosure may comprise one or more genes encoding a human antibody light chain. Any suitable human antibody light chain-encoding genes can be used in the HAC vectors of the invention. The human antibody light chain includes two types of genes, i.e., the kappa/K chain gene and the lambda/L chain gene. In one embodiment, the HAC comprises genes encoding both kappa and lambda, in one or more copies. The variable region and constant region of the kappa chain are positioned at 2p11.2-2p12 of the human chromosome 2, and the lambda chain forms a cluster positioned at 22q11.2 of the human chromosome 22. Therefore, in one embodiment, the HAC vectors of the invention comprise a human chromosome 2 fragment containing the kappa chain gene cluster of the 2p11.2-2p12 region. In another embodiment, the HAC vectors of the present invention comprise a human chromosome 22 fragment containing the lambda chain gene cluster of the 22q11.2 region.

In another embodiment, the HAC vector comprises at least one gene encoding a human antibody surrogate light chain. The gene encoding a human antibody surrogate light chain refers to a gene encoding a transient antibody light chain which is associated with an antibody heavy chain produced by a gene reconstitution in the human pro-B cell to constitute the pre-B cell receptor (preBCR). Any suitable human antibody surrogate light chain encoding gene can be used, including but not limited to the VpreB1 (SEQ ID NO: 7), VpreB3 (SEQ ID NO: 8) and λ5 (also known as IgLL1, SEQ ID NO: 9) human antibody surrogate light chains, and combinations thereof. The VpreB gene and the λ5 gene are positioned within the human antibody lambda chain gene locus at 22q11.2 of the human chromosome 22. Therefore, in one embodiment the HAC may comprise the 22q11.2 region of human chromosome 22 containing the VpreB gene and the λ5 gene. The human VpreB gene of the present invention provides either or both of the VpreB1 gene (SEQ ID NO: 7) and the VpreB3 (SEQ ID NO: 8) gene and in one embodiment provides both of the VpreB1 gene and the VpreB3 gene.

In yet another embodiment, the HAC vector comprises a gene encoding an ungulate-derived IgM heavy chain constant region. In this embodiment, the IgM heavy chain constant region is expressed as a chimera with the human IgM antibody heavy chain variable region. Any suitable ungulate IgM heavy chain antibody constant region encoding nucleic acid can be used, including but not limited to bovine IgM, (SEQ ID NO: 10), horse IgM, (SEQ ID NO: 11), sheep IgM, (SEQ ID NO: 12), and pig IgM, (SEQ ID NO: 13). In one embodiment, the chimeric IgM comprises the sequence in SEQ ID NO: 14. Pre-BCR/BCR signaling through the IgM heavy chain molecule promotes proliferation and development of the B cell by interacting with the B cell membrane molecule Ig-alpha/Ig-beta to cause a signal transduction in cells. Transmembrane region and/or other constant region of IgM are considered to have important roles in the interaction with Ig-alpha/Ig-beta for signal transduction. Examples of the IgM heavy chain constant regions include nucleic acids encoding constant region domains such as CH1, CH2, CH3, and CH4, and the B-cell transmembrane and cytoplasmic domains such as TM1 and TM2. The nucleic acid encoding an ungulate-derived IgM heavy chain constant region which is comprised in the human artificial chromosome vector of the invention is not particularly limited so long as the region is in a range which may sufficiently induce the signal of the B-cell receptor or B-cell proliferation/development in the above-described IgM heavy chain constant region. In one embodiment, the nucleic acid encoding an ungulate-derived IgM heavy chain constant region provides a transmembrane and cytoplasmic TM1 domain and TM2 domain derived from an ungulate, and in other embodiments encodes the ungulate-derived CH2 domain, CH3 domain, CH4 domain, TM1 domain, and TM2 domain or the ungulate-derived CH1 domain, CH2 domain, CH3 domain, CH4 domain, TM1 domain, and TM2 domain.

In one embodiment, the gene encoding the IgM heavy chain constant region of the bovine is a gene encoding a bovine IgM heavy chain constant region which is included in an IGHM region at which a bovine endogenous IgM heavy chain gene is positioned (derived from IGHM) or a gene encoding a bovine IgM heavy chain constant region in an IGHML1 region (derived from IGHML1). In another embodiment, the gene encoding a bovine IgM heavy chain constant region is included in the IGHM region.

In a further embodiment, the HAC comprises a gene encoding a human antibody heavy chain comprises a gene encoding a human heavy chain (for example, a human IgG heavy chain, such as an IgG1 heavy chain), and wherein a transmembrane domain and an intracellular domain of a constant region of the human heavy chain gene are replaced with a transmembrane domain and an intracellular domain of an ungulate-derived heavy chain (for example, an ungulate IgG heavy chain, such as an IgG1 heavy chain), constant region gene. In one embodiment, gene encoding the transmembrane domain and the intracellular domain of an ungulate-derived (such as bovine) IgG (such as IgG1) heavy chain constant region are used to replace the corresponding regions of the human IgG heavy chain gene. In another embodiment, the gene encoding the TM1 and TM2 domains of an ungulate-derived (such as bovine) IgG (such as IgG1) heavy chain constant region are used to replace the corresponding regions of the human IgG heavy chain gene. In another embodiment, the gene encoding the one or more of the CH1-CH4 domains and/or the TM1 and TM2 domains of an ungulate-derived (such as bovine) IgG (such as IgG1) heavy chain constant region are used to replace the corresponding regions of the human IgG heavy chain gene.

The disclosure further provides transgenic ungulates comprising a HAC vector according to any embodiment or combination of embodiments of the disclosure. The transgenic ungulate comprising the HAC vector of the present invention refers to an animal into which the human artificial chromosome vector of the present invention is introduced. The transgenic ungulate having the HAC of the present invention is not particularly limited so long as the animal is a transgenic ungulate in which the human artificial chromosome fragment may be introduced into a cell thereof, and any non-human animals, for example, ungulates such as cows, horses, goats, sheep, and pigs; and the like may be used. In one aspect, the transgenic ungulate is a bovine. A transgenic ungulate having the HAC vector of the present invention may be constructed, for example, by introducing the HAC vector of the present disclosure into an oocyte of a host animal using any suitable technique, such as those described herein. The HAC vector of the present invention may, for example, be introduced into a somatic cell derived from a host ungulate by a microcell fusion method. Thereafter, the animal having the HAC vector may be constructed by transplanting a nucleus or chromatin agglomerate of the cell into an oocyte and transplanting the oocyte or an embryo to be formed from the oocyte into the uterus of a host animal to give birth. It may be confirmed by a method of Kuroiwa et al. (Kuroiwa et al., *Nature Biotechnology*, 18, 1086-1090, 2000 and Kuroiwa et al., *Nature Biotechnology*, 20, 889-894) whether an animal constructed by the above method has the human artificial chromosome vector.

The disclosure further provides transgenic ungulates comprising genes integrated into its genome encoding:
  (a) one or more human antibody heavy chains, wherein each gene encoding an antibody heavy chain is operatively linked to a class switch regulatory element;
  (b) one or more human antibody light chains; and
  (c) one or more human antibody surrogate light chains, and/or an ungulate-derived IgM heavy chain constant region;

wherein at least one class switch regulatory element of the genes encoding the one or more human antibody heavy chains is replaced with an ungulate-derived class switch regulatory element.

In such embodiments, the transgenic ungulate may comprise any embodiment or combination of embodiments of the nucleic acids as described herein for the HAC, but rather than being present in a HAC, they are integrated into a chromosome of the ungulate.

The disclosure further provides a method of producing a human antibody, comprising: (a) administering human coronavirus, or other target antigen of the disclosure, to the transgenic ungulate of any embodiment or combination of embodiments of the disclosure to produce and accumulate a population of human immunoglobulins specific to human coronavirus (or to T cells, B cells, and/or monocytes) in the serum or plasma of the ungulate; and optionally (b) isolating, recovering, and/or purifying the population of human immunoglobulins specific to the human coronavirus (or to T cells, B cells, and/or monocytes) from the serum or plasma of the ungulate.

The polyclonal serum or plasma, or human immunoglobulin purified from the polyclonal serum or plasma, may be used as an Immunoglobulin product for coronavirus disease.

In a variation, the disclosure provides a method of recovering the protein sequence of a human antibody comprises: (i) isolating lymphocytes from the transgenic ungulate; (ii) generating a human monoclonal antibody producing hybridoma from the lymphocytes; and (iii) recovering human monoclonal antibody specific to the antigen from the hybridoma. In another embodiment, the lymphocytes from the transgenic ungulate are isolated from lymph nodes of the transgenic ungulate. In a further embodiment the transgenic ungulate is hyperimmunized with the target antigen.

A coronavirus protein-specific human immunoglobulin (such as coronavirus S protein-specific human immunoglobulin) may be produced by immunizing the transgenic ungulate having the HAC vector with human coronavirus protein, or another antigen of the disclosure, to produce the coronavirus protein-specific human immunoglobulin in the serum or plasma of the transgenic ungulate and recovering the coronavirus protein-specific human immunoglobulin from the serum or plasma of the transgenic ungulate.

Examples of methods for detecting and measuring the coronavirus S protein-specific human immunoglobulin in a composition include a binding assay by an enzyme-linked immunosorbent assay, and the like. The binding amount of a human immunoglobulin may be measured by incubating the composition comprising the human immunoglobulin with cells (e.g., coronavirus, T cells, B cells and/or monocytes, or recombinant protein antigen(s)), and then using an antibody specifically recognizing human immunoglobulin.

In a variation, the methods of the disclosure are used to generate a monoclonal antibody. Methods of preparing and utilizing various types of antibodies are well-known to those of skill in the art and would be suitable in practicing the present invention (see, for example, Harlow, et al. Antibodies: A Laboratory Manual, Cold Spring Harbor Laboratory, 1988; Kohler and Milstein, *Nature* 256:495 (1975)). An example of a preparation method for hybridomas comprises the following steps of: (1) immunizing a transgenic ungulate with coronavirus; (2) collecting antibody-producing cells from the transgenic ungulate (i.e. from lymph nodes); (3) fusing the antibody-producing cells with myeloma cells; (4) selecting hybridomas that produce a monoclonal antibody specific to coronavirus from the fused cells obtained in the above step; and optionally (5) selecting a hybridoma that produces a monoclonal antibody specific to coronavirus from the selected hybridomas.

In embodiments of the methods of producing polyclonal immunoglobulin specific for coronavirus protein (such as coronavirus S protein-specific human immunoglobulin), the transgenic ungulate produces human polyclonal immunoglobulin specific for coronavirus protein. The method may comprise collecting the polyclonal serum and/or polyclonal plasma from the transgenic ungulate. In some embodiments, the ungulate is a bovine. In some embodiments, the polyclonal immunoglobulin composition comprises a population of fully human immunoglobulins. In some embodiments, the polyclonal immunoglobulin composition comprises a population of fully human immunoglobulins, substantially human immunoglobulins.

Some embodiments of the methods of the disclosure, and related compositions, have the surprising advantage that the coronavirus protein-specific immunoglobulins (such as coronavirus S protein-specific human immunoglobulin) are produced in high yield, in high purity, and/or as a high percentage of total immunoglobulin present in the serum or plasma of the transgenic ungulate. Furthermore, some embodiments produce coronavirus protein-specific immunoglobulins having glycans that comprise at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95% or higher percentage of fucosylated glycans. Furthermore, some embodiments produce coronavirus protein-specific immunoglobulins having at most about the same ADCC or CDC activity as a reference immunoglobulin preparation, e.g. human-derived immunoglobulin.

In some embodiments, the population of human immunoglobulins binds FcγRI with a $K_D$ of 15 nM or greater. In some embodiments, the population of human immunoglobulins binds FcγRIIa with a $K_D$ of 500 nM or greater. In some embodiments, the population of human immunoglobulins binds FcγRIIb/c with a $K_D$ of 1 μM or greater. In some embodiments, the population of human immunoglobulins binds FcγRIIIa with a $K_D$ of 1 μM or greater. In some embodiments, the population of human immunoglobulins binds FcγRIIIa with a $K_D$ of 1 nM or greater.

In some embodiments of the methods and compositions of the disclosure, the polyclonal serum or polyclonal plasma comprises at least 0.1%, at least 0.2%, at least 0.3%, at least 0.4%, at least 0.5%, at least 0.6%, at least 0.7%, at least 0.8%, at least 0.9%, at least 1%, at least 1.1%, at least 1.2%, at least 1.3%, at least 1.4%, at least 1.5%, at least 1.6%, at least 1.7%, at least 1.8%, at least 1.9%, at least 2%, at least 2.1%, at least 2.2%, at least 2.3%, at least 2.4%, at least 2.5%, at least 2.6%, at least 2.7%, at least 2.8%, at least 2.9%, at least 3%, at least 3.1%, at least 3.2%, at least 3.3%, at least 3.4%, at least 3.5%, at least 3.6%, at least 3.7%, at least 3.8%, at least 3.9%, at least 4%, at least 4.1%, at least 4.2%, at least 4.3%, at least 4.4%, at least 4.5%, at least 4.6%, at least 4.7%, at least 4.8%, at least 4.9%, at least 5%, at least 5.1%, at least 5.2%, at least 5.3%, at least 5.4%, at least 5.5%, at least 5.6%, at least 5.7%, at least 5.8%, at least 5.9%, at least 5.9%, at least 6.0%, at least 6.1%, at least 6.2%, at least 6.3%, at least 6.4%, at least 6.5%, at least 6.6%, at least 6.7%, at least 6.8%, at least 6.9%, at least 7.0%, at least 7.1%, at least 7.2%, at least 7.3%, at least 7.4%, at least 7.5%, at least 7.6%, at least 7.7%, at least 7.8%, at least 7.9%, at least 8.0%, at least 8.1%, at least 8.2%, at least 8.3%, at least 8.4%, at least 8.5%, at least 8.6%, at least 8.7%, at least 8.8%, at least 8.8%, at least 9.0%, at least 9.1%, at least 9.2%, at least 9.3%, at least 9.4%, at least 9.5%, at least 9.6%, at least 9.7%, at least 9.8%, at least 9.8%, at least 9.9%, or at least 10% fully human (or substantially human) immunoglobulin by mass of total immunoglobulin in the polyclonal serum or polyclonal plasma.

In some embodiments of the methods and compositions of the disclosure, the polyclonal serum or polyclonal plasma comprises 0.1-0.6%, 0.2-0.7%, 0.3-0.8%, 0.4-0.9%, 0.5-1%, 0.6-1.1%, 0.7-1.2%, 0.8-1.3%, 0.9-1.4%, 1-1.5%, 1.1-1.6%, 1.2-1.7%, 1.3-1.8%, 1.4-1.9%, 1.5-2%, 1.6-2.1%, 1.7-2.2%, 1.8-2.3%, 1.9-2.4%, 2-2.5%, 2.1-2.6%, 2.2-2.7%, 2.3-2.8%, 2.4-2.9%, 2.5-3%, 2.6-3.1%, 2.7-3.2%, 2.8-3.3%, 2.9-3.4%, 3-3.5%, 3.1-3.6%, 3.2-3.7%, 3.3-3.8%, 3.4-3.9%, 3.5-4%, 3.6-4.1%, 3.7-4.2%, 3.8-4.3%, 3.9-4.4%, 4-4.5%, 4.1-4.6%, 4.2-4.7%, 4.3-4.8%, 4.4-4.9%, 4.5-5%, 4.6-5.1%, 4.7-5.2%, 4.8-5.3%, 4.9-5.4%, 5-5.5%, 5.1-5.6%, 5.2-5.7%, 5.3-5.8%, 5.4-5.9%, 5.5-6%, 5.6-6.1%, 5.7-6.2%, 5.8-6.3%, or 5.9-6.4% fully human (or substantially human) immunoglobulin by mass of total immunoglobulin in the polyclonal serum or polyclonal plasma.

In some embodiments of the methods and compositions of the disclosure, the polyclonal serum or polyclonal plasma comprises 0-0.5%, 0.5-1%, 1-1.5%, 1.5-2%, 2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9- 9.5%, 9.5-10% or greater fully human (or substantially human) immunoglobulin by mass of total immunoglobulin in the polyclonal serum or polyclonal plasma.

In some embodiments of the methods and compositions of the disclosure, the polyclonal serum or polyclonal plasma comprises 0-1%, 1-2%, 2-3%, 3-4%, 4-5%, 5-6%, 6-7%, 7-8%, 8-9%, 9-10%, or greater fully human (or substantially human) immunoglobulin by mass of total immunoglobulin in the polyclonal serum or polyclonal plasma.

In some embodiments of the methods and compositions of the disclosure, the polyclonal serum or polyclonal plasma comprises 0-5%, 5-10%, 10-15%, 15-20%, 20-25%, 25-30%, 30-35%, 35-40%, or greater fully human (or substantially human) immunoglobulin by mass of total immunoglobulin in the polyclonal serum or polyclonal plasma.

In some embodiments of the methods and compositions of the disclosure, the polyclonal serum or polyclonal plasma comprises 0-5%, 5-10%, 10-15%, 15-20%, 20-25%, 25-30%, 30-35%, 35-40%, or greater fully human (or substantially human) immunoglobulin by mass of total immunoglobulin in the polyclonal serum or polyclonal plasma.

In some embodiments of the methods and compositions of the disclosure, the polyclonal serum or polyclonal plasma comprises at least 1%, at least 2%, at least 3%, at least 4%, at least 5%, at least 6%, at least 7%, at least 8%, at least 9%, or at least 10% fully human (or substantially human) immunoglobulin by mass of total immunoglobulin in the polyclonal serum or polyclonal plasma.

In some embodiments of the methods and compositions of the disclosure, the polyclonal serum or polyclonal plasma comprises 1-4%, 2-5%, 3-6%, 4-7%, 5-8%, 6-9%, or 7-10% fully human (or substantially human) immunoglobulin by mass of total immunoglobulin in the polyclonal serum or polyclonal plasma.

In some embodiments of the methods and compositions of the disclosure, the polyclonal immunoglobulin comprises at least 0.1%, at least 0.2%, at least 0.3%, at least 0.4%, at least 0.5%, at least 0.6%, at least 0.7%, at least 0.8%, at least 0.9%, at least 1%, at least 1.1%, at least 1.2%, at least 1.3%, at least 1.4%, at least 1.5%, at least 1.6%, at least 1.7%, at least 1.8%, at least 1.9%, at least 2%, at least 2.1%, at least 2.2%, at least 2.3%, at least 2.4%, at least 2.5%, at least 2.6%, at least 2.7%, at least 2.8%, at least 2.9%, at least 3%, at least 3.1%, at least 3.2%, at least 3.3%, at least 3.4%, at least 3.5%, at least 3.6%, at least 3.7%, at least 3.8%, at least 3.9%, at least 4%, at least 4.1%, at least 4.2%, at least 4.3%, at least 4.4%, at least 4.5%, at least 4.6%, at least 4.7%, at least 4.8%, at least 4.9%, at least 5%, at least 5.1%, at least 5.2%, at least 5.3%, at least 5.4%, at least 5.5%, at least 5.6%, at least 5.7%, at least 5.8%, at least 5.9%, at least 5.9%, at least 6.0%, at least 6.1%, at least 6.2%, at least 6.3%, at least 6.4%, at least 6.5%, at least 6.6%, at least 6.7%, at least 6.8%, at least 6.9%, at least 7.0%, at least 7.1%, at least 7.2%, at least 7.3%, at least 7.4%, at least 7.5%, at least 7.6%, at least 7.7%, at least 7.8%, at least 7.9%, at least 8.0%, at least 8.1%, at least 8.2%, at least 8.3%, at least 8.4%, at least 8.5%, at least 8.6%, at least 8.7%, at least 8.8%, at least 8.8%, at least 9.0%, at least 9.1%, at least 9.2%, at least 9.3%, at least 9.4%, at least 9.5%, at least 9.6%, at least 9.7%, at least 9.8%, at least 9.8%, at least 9.9%, or at least 10% fully human (or substantially human) immunoglobulin by mass of total immunoglobulin in the polyclonal immunoglobulin.

In some embodiments of the methods and compositions of the disclosure, the polyclonal immunoglobulin comprises 0.1-0.6%, 0.2-0.7%, 0.3-0.8%, 0.4-0.9%, 0.5-1%, 0.6-1.1%, 0.7-1.2%, 0.8-1.3%, 0.9-1.4%, 1-1.5%, 1.1-1.6%, 1.2-1.7%, 1.3-1.8%, 1.4-1.9%, 1.5-2%, 1.6-2.1%, 1.7-2.2%, 1.8-2.3%, 1.9-2.4%, 2-2.5%, 2.1-2.6%, 2.2-2.7%, 2.3-2.8%, 2.4-2.9%, 2.5-3%, 2.6-3.1%, 2.7-3.2%, 2.8-3.3%, 2.9-3.4%, 3-3.5%, 3.1-3.6%, 3.2-3.7%, 3.3-3.8%, 3.4-3.9%, 3.5-4%, 3.6-4.1%, 3.7-4.2%, 3.8-4.3%, 3.9-4.4%, 4-4.5%, 4.1-4.6%, 4.2-4.7%, 4.3-4.8%, 4.4-4.9%, 4.5-5%, 4.6-5.1%, 4.7-5.2%, 4.8-5.3%, 4.9-5.4%, 5-5.5%, 5.1-5.6%, 5.2-5.7%, 5.3-5.8%, 5.4-5.9%, 5.5-6%, 5.6-6.1%, 5.7-6.2%, 5.8-6.3%, or 5.9-6.4% fully human (or substantially human) immunoglobulin by mass of total immunoglobulin in the polyclonal immunoglobulin.

In some embodiments of the methods and compositions of the disclosure, the polyclonal immunoglobulin comprises 0-0.5%, 0.5-1%, 1-1.5%, 1.5-2%, 2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, 9.5-10% or greater fully human (or substantially human) immunoglobulin by mass of total immunoglobulin in the polyclonal immunoglobulin.

In some embodiments of the methods and compositions of the disclosure, the polyclonal immunoglobulin comprises 0-1%, 1-2%, 2-3%, 3-4%, 4-5%, 5-6%, 6-7%, 7-8%, 8-9%, 9-10%, or greater fully human (or substantially human) immunoglobulin by mass of total immunoglobulin in the polyclonal immunoglobulin.

In some embodiments of the methods and compositions of the disclosure, the polyclonal immunoglobulin comprises 0-5%, 5-10%, 10-15%, 15-20%, 20-25%, 25-30%, 30-35%, 35-40%, or greater fully human (or substantially human) immunoglobulin by mass of total immunoglobulin in the polyclonal immunoglobulin.

In some embodiments of the methods and compositions of the disclosure, the polyclonal immunoglobulin comprises 0-5%, 5-10%, 10-15%, 15-20%, 20-25%, 25-30%, 30-35%, 35-40%, or greater fully human (or substantially human) immunoglobulin by mass of total immunoglobulin in the polyclonal immunoglobulin.

In some embodiments of the methods and compositions of the disclosure, the polyclonal immunoglobulin comprises at least 1%, at least 2%, at least 3%, at least 4%, at least 5%, at least 6%, at least 7%, at least 8%, at least 9%, or at least 10% fully human (or substantially human) immunoglobulin by mass of total immunoglobulin in the polyclonal immunoglobulin.

In some embodiments of the methods and compositions of the disclosure, the polyclonal immunoglobulin comprises 1-4%, 2-5%, 3-6%, 4-7%, 5-8%, 6-9%, or 7-10% fully human (or substantially human) immunoglobulin by mass of total immunoglobulin in the polyclonal immunoglobulin.

In some embodiments of the methods and compositions of the disclosure, the polyclonal immunoglobulin comprises at least 5% fully human immunoglobulin by mass of total immunoglobulin in the polyclonal immunoglobulin.

In some embodiments of the methods and compositions of the disclosure, the polyclonal immunoglobulin comprises 2% to 5% fully human immunoglobulin by mass of total immunoglobulin in the polyclonal immunoglobulin.

In some embodiments, the ungulate-derived polyclonal immunoglobulin comprises "chimeric" human immunoglobulin having a human heavy chain and an ungulate kappa light chain (termed "cIgG"). In some embodiments, the polyclonal immunoglobulin comprises less than about 0.5%, less than about 0.75%, less than about 1.0%, less than about 1.25%, less than about 1.5%, less than about 1.75%, less than about 2.0%, less than about 2.25%, less than about 2.5%, less than about 2.75%, less than about 3.0%, less than about 3.25%, less than about 3.5%, less than about 3.75%, or less than about 4.0% cIgG as a percent of total protein concentration. In some embodiments, the polyclonal immunoglobulin comprises about 0.5% to about 1.0%, about 1.0% to about 1.5%, about 1.5% to about 2.0%, about 1.5% to about 2.0%, about 2.0% to about 2.5%, or about 2.5% to about 3.0% cIgG as a percent of total protein concentration. In some embodiments, the polyclonal immunoglobulin comprises about 0.5% to about 1.0%, about 1.0% to about 2.0%, or about 1.0 to about 3.0% cIgG as a percent of total protein concentration.

In some embodiments, the polyclonal immunoglobulins of the disclosure are less potent in a complement-dependent cytotoxicity (CDC) assay than a reference product (e.g. human-derived polyclonal immunoglobulin). In some embodiments, the polyclonal immunoglobulins of the disclosure are at most about 5%, at most about 10%, at most about 25%, at most about 50%, at most about 100%, at most about 150%, or more at most about 200% potent in a complement-dependent cytotoxicity (CDC) assay than a reference product (e.g. human-derived polyclonal immunoglobulin).

In some embodiments, the polyclonal immunoglobulins of the disclosure generates lower toxicity towards CD8+ cells than a reference product (e.g. human-derived polyclonal immunoglobulin. In some embodiments, the polyclonal immunoglobulins of the disclosure are at most about 5%, at most about 10%, at most about 25%, at most about 50%, at most about 100%, at most about 150%, or at most about 200% more potent in CD8+ cell killing assay than a reference product (e.g. human-derived polyclonal immunoglobulin).

In some embodiments, the polyclonal immunoglobulins of the disclosure generated lower rates of CD4+ T cell apoptosis than a reference product (e.g. human-derived polyclonal immunoglobulin. In some embodiments, the polyclonal immunoglobulins of the disclosure are at least about 5%, at least about 10%, at least about 25%, at least about 50%, at least about 100%, at least about 150%, or at least about 200% less toxic in a CD4+ cell apoptosis assay than a reference product (e.g. human-derived polyclonal immunoglobulin).

In some embodiments, the polyclonal immunoglobulins of the disclosure better preserves $T_{reg}$ to conventional T cell rations than a reference product (e.g. human-derived polyclonal immunoglobulin. In some embodiments, the polyclonal immunoglobulins of the disclosure are at least about 5%, at least about 10%, at least about 25%, at least about 50%, at least about 100%, at least about 150%, or at least about 200% less toxic to $T_{reg}$ cells than a reference product (e.g. human-derived polyclonal immunoglobulin).

In some embodiments of the methods and compositions of the disclosure, the population of fully human immunoglobulins (or substantially human) specifically binds human coronavirus, coronavirus S protein, or another coronavirus antigen. In some embodiments, the population of fully human (or substantially human) immunoglobulins specifically binds a human coronavirus (e.g., SARS-CoV-2), human coronavirus S protein, or another human coronavirus antigen.

In some embodiments, a genome of the transgenic ungulate comprises a human immunoglobulin locus.

In some embodiments, the transgenic ungulate is immunized 3, 4, 5, or more times.

In some embodiments, the population of fully human or substantially human immunoglobulins are purified from the serum of the transgenic ungulate after immunization.

The disclosure provides methods of providing human polyclonal immunoglobulin specific for coronavirus protein (such as coronavirus S protein) treatment to a subject in need thereof, comprising administering to the subject a polyclonal immunoglobulin according to the disclosure. In some embodiments, the method provides an effective amount of human polyclonal immunoglobulin specific for coronavirus protein to the subject.

The disclosure provides methods of providing human polyclonal immunoglobulin specific for coronavirus protein (such as coronavirus S protein) treatment to a subject in need thereof, comprising administering to the subject a composition produced by immunizing a transgenic ungulate with human coronavirus. In some embodiments, the method provides an effective amount of human polyclonal immunoglobulin specific for coronavirus protein to the subject.

The disclosure provides methods of providing human polyclonal immunoglobulin specific for coronavirus protein (such as coronavirus S protein) treatment to a subject in need thereof, comprising administering to the subject a polyclonal immunoglobulin produced according to the disclosure. In some embodiments, the method provides an effective amount of human polyclonal immunoglobulin specific for coronavirus S protein to the subject.

The disclosure further provides pharmaceutical compositions, comprising a population of fully human or substantially human immunoglobulins, and one or more pharmaceutically acceptable excipients. In some embodiments, the population of fully human or substantially human immunoglobulins specifically binds human coronavirus, human coronavirus S protein, or another human coronavirus antigen.

In some embodiments, the pharmaceutical composition comprises at least about 1 mg/mL, at least about 50 mg/mL, at least about 100 mg/mL, or at least about 1,000 mg/mL of fully human or substantially human immunoglobulin. In some embodiments, the pharmaceutical composition comprises at least about 100 µg/mL, at least about 250 µg/mL, at least about 500 µg/mL, at least about 750 µg/mL, or at least about 1,000 µg/mL of fully human or substantially human immunoglobulin.

In some embodiments, the fully human or substantially human immunoglobulin is produced in an ungulate. In some embodiments, the ungulate is a bovine.

In some embodiments, the pharmaceutical composition comprises at least 5% fully human immunoglobulin by mass of total immunoglobulin in the pharmaceutical composition.

In some embodiments, the pharmaceutical composition comprises 2% to 5% fully human immunoglobulin by mass of total immunoglobulin in the pharmaceutical composition.

EXAMPLES

The following specific examples are to be construed as merely illustrative, and not limitative of the remainder of the disclosure in any way whatsoever.

Example 1

Production of Human Polyclonal Immunoglobulin in Transchromosomic Bovine (TcB) System Applicant has developed a transchromosomic (Tc) bovine production system in which bovine Ig genes are knocked-out and a human artificial chromosome (HAC) vector is introduced into the bovine genome to express human polyclonal antibodies. These Tc cattle are immunized with specific targets, such as an ectodomain of the spike (S) protein of SARS-CoV-2, to produce substantial amounts of antigen specific-human polyclonal antibodies for therapeutic treatments.

Transchromosomic (Tc) bovines (qualified as producing >2 mg/mL of total human IgG, >30% IgG1) were immunized initially (vaccinations 1 and 2) with a plasmid DNA (pDNA) vaccine that expresses wild-type SARS-CoV-2 spike protein, followed by additional immunizations (vaccinations 3 and beyond) with a recombinant spike protein from SARS-CoV-2 produced in insect cells, according the schedule in Table 1.

TABLE 1

| Vaccination Interval and Formulation | | |
|---|---|---|
| Antigen Type | Vaccination | Vaccine Formulation |
| pDNA | V1 to V2 with 3-4 week interval | 12 mg SARS-CoV-2 pDNA + ISA-206 50%/Quil A 2 mg |
| Spike protein | V3 to V5 with 4 week interval | 2 to 5 mg SARS-CoV-2 recombinant spike protein + ISA-206 50%/Quil A 2 mg |

For the first and second vaccinations (V1 and V2), pDNA encoding full-length spike (S) protein from Severe Acute Respiratory Syndrome-related Coronavirus 2 (SARS-CoV-2), Wuhan-Hu-1 of

SEQ ID NO: 19
(MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKSN

IIRGWIFGTTLDSKTQSLLIVNNATNVVIKVCEFQFCNDPFLGVYYHKNN

KSWMESEFRVYSSANNCTFEYVSQPFLMDLEGKQGNFKNLREFVFKNIDG

-continued
YFKIYSKHTPINLVRDLPQGFSALEPLVDLPIGINITRFQTLLALHRSYL

TPGDSSSGWTAGAAAYYVGYLQPRTFLLKYNENGTITDAVDCALDPLSET

KCTLKSFTVEKGIYQTSNFRVQPTESIVRFPNITNLCPFGEVFNATRFAS

VYAWNRKRISNCVADYSVLYNSASFSTFKCYGVSPTKLNDLCFTNVYADS

FVIRGDEVRQIAPGQTGKIADYNYKLPDDFTGCVIAWNSNNLDSKVGGNY

NYLYRLFRKSNLKPFERDISTEIYQAGSTPCNGVEGENCYFPLQSYGFQP

TNGVGYQPYRVVVLSFELLHAPATVCGPKKSTNLVKNKCVNFNFNGLTGT

GVLTESNKKFLPFQQFGRDIADTTDAVRDPQTLEILDITPCSFGGVSVIT

PGTNTSNQVAVLYQDVNCTEVPVAIHADQLTPTWRVYSTGSNVFQTRAGC

LIGAEHVNNSYECDIPIGAGICASYQTQTNSPRRARSVASQSIIAYTMSL

GAENSVAYSNNSIAIPTNFTISVTTEILPVSMTKTSVDCTMYICGDSTEC

SNLLLQYGSFCTQLNRALTGIAVEQDKNTQEVFAQVKQIYKTPPIKDFGG

FNFSQILPDPSKPSKRSFIEDLLENKVTLADAGFIKQYGDCLGDIAARDL

ICAQKFNGLTVLPPLLTDEMIAQYTSALLAGTITSGWTFGAGAALQIPFA

MQMAYRFNGIGVTQNVLYENQKLIANQFNSAIGKIQDSLSSTASALGKLQ

DVVNQNAQALNTLVKQLSSNFGAISSVLNDILSRLDKVEAEVQIDRLITG

RLQSLQTYVTQQLIRAAEIRASANLAATKMSECVLGQSKRVDFCGKGYHL

MSFPQSAPHGVVFLHVTYVPAQEKNFTTAPAICHDGKAHFPREGVFVSNG

THWFVTQRNFYEPQIITTDNTFVSGNCDVVIGIVNNTVYDPLQPELDSFK

EELDKYFKNHTSPDVDLGDISGINASVVNIQKEIDRLNEVAKNLNESLID

LQELGKYEQYIKWPWYIWLGFIAGLIAIVMVTIMLCCMTSCCSCLKGCCS

CGSCCKFDEDDSEPVLKGVKLHYT; GenPept: QHD43416), was administered by intramuscular (IM) injection. The adjuvants Montanide ISA-206 and Quil A were co-administered adjacent to the DNA vaccination site.

For the third vaccination (V3), a recombinant S protein from SARS-CoV-2, Wuhan-Hu-1 (GenPept: QHD43416) mixed with Montanide ISA-206 and Quil A was administered. The S protein was produced in insect cells using a baculovirus expression system and purified by nickel affinity chromatography. This recombinant protein contains 1196 residues (ectodomain) of the SARS-CoV-2 S protein. It was modified to remove the polybasic S1/S2 cleavage site (RRAR [SEQ ID NO:18] to A; residues 682 to 685), stabilized with a pair of mutations (K986P and V987P, wild type numbering) and includes a thrombin cleavage site, T4 foldon trimerization domain and C-terminal hexa-histidine tag.

Collected plasma was frozen for shipment, thawed, pooled, fractionated by caprylic acid (CA), and clarified by depth filtration. Clarified material containing Tc bovine-derived human immunoglobulin G (IgG) was purified by affinity chromatography, first using an anti-human IgG affinity column to bind Tc bovine-derived human IgG (hIgG) and remove bovine plasma proteins (BPP) followed by a low pH treatment for viral inactivation, and, then, by passing through an anti-bovine IgG (bIgG) heavy chain (HC) specific affinity column to further remove residual IgG molecules that contain a bovine HC or Fc of bovine HC. The Tc bovine-derived human IgG fraction was then concentrated and diafiltered prior to a Q Sepharose chromatography polishing step, nanofiltration, final buffer exchange, concentration and sterile filtration.

Biochemical Characterization of TcB-Produced Human Polyclonal Immunoglobulin

The Tc bovine was engineered to be biased to human IgG1. Human IgG subclasses ratios for normal human plasma and Tc bovine are presented in Table 2. In Tc bovine derived antibodies, the IgG subclasses are in the following ranges:

TABLE 2

IgG Subclasses Present in Normal Human IgG Compared to Tc Bovine Human IgG

| IgG Species | Normal Human IgG % | Human IgG from Tc Bovine % |
|---|---|---|
| IgG1 | 60.3-71.5 | 70.3-98.6 |
| IgG2 | 19.4-31.0 | 1.4-34.5 |
| IgG3 | 5.0-8.4 | 0.0-0.3 |
| IgG4 | 0.7-4.2 | 0.0-0.4 |

Purified immunoglobulin was characterized by SDS-PAGE (FIGS. 2A-2B) and size exclusion chromatograph (FIG. 3). Human immunoglobulin is present at high concentration (Table 3) and high monomer abundance and IgG1 percentage (Table 4).

TABLE 3

| Analytical parameter | Unit | Hizentra original | Hizentra re-formulated | Tc bovine hIgG re-formulated |
|---|---|---|---|---|
| Protein conc., A280 | mg/mL | 204.2 | 201.7 | 192.8 |
| Protein conc., Biuret | mg/mL | 1933 | 208.8 | 188.5 |
| Volume | mL | n.a. | 23 | 35 |
| L-proline | mmol/L | 254 | 219 | 218 |
| P80 | mg/L | 15 | 26 | 67 |
| pH | (1% protein in NaCl 0.9%) | 4.85 | 5.59 | 6.09 |
| Viscosity | mPa*s | 15 | 21 | 14 |
| Endotox LA L | IU/mL | <0.2 | <0.05 | <0.5 |
| Endotox Endosafe | IU/mg protein | <0.001 | <0.005 | <0.005 |

TABLE 4

| Analytical parameter | Unit | Hizentra original | Hizentra re-formulated | Tc bovine hIgG re-formulated |
|---|---|---|---|---|
| SEC-HPLC % | % Aggregates | <0.1 | <0.1 | <0.1 |
| | % Dimers | 8.98 | 13.14 | 0.76 |
| | % Monomers | 91.02 | 86.86 | 99.24 |
| | % Fragments | <0.1 | <0.1 | <0.1 |
| IgG subclasses | % IgG1 | | 70.6 | 93.5 |
| | % IgG2 | | 26.3 | 6.5 |
| | % IgG3 | | 1.6 | 0 |
| | % IgG4 | | 1.6 | 0 |
| Complement activ. | % ACA | 14 | 15 | 16 |
| HBs-Ab | IU/mL | 14.6 | 9.2 | not detectable |
| Parvovirus-Ab | IU/mL | 595 | 509 | 5 |
| Diphteria a antitoxin | IU/mL | 18.1 | 18.1 | 57.8 |

Functional Characterization of TcB-Produced Human Polyclonal Immunoglobulin

Binding to human Fc gamma receptors was assay by biolayer interferometry. Results are shown in Table 5.

TABLE 5

| Receptor | $K_D$ | $K_{on}$ (1/Ms) | $K_{dis}$ (1/s) | Calculation method |
|---|---|---|---|---|
| IgG (Hizentra) | | | | |
| FcγRI (CD64) | 19.7 nM ± 2.0 | $8.7 \times 10^4$ | $1.7 \times 10^{-3}$ | Kinetic fit |
| FcγRIIa (CD32a) | 212.7 nM ± 7.4 | $2.6 \times 10^5$ | $5.5 \times 10^{-2}$ | Kinetic fit |
| FcγRIIb/c (CD32b/c) | 2.7 μM ± 0.3 | n/a | n/a | Steady state |
| FcγRIIIa (CD16a) | 495.9 nM ± 42.6 | $7.3 \times 10^4$ | $3.6 \times 10^{-2}$ | Kinetic fit |
| FcRn | 1.0 nM ± 0.06 | $2.5 \times 10^6$ | $2.5 \times 10^{-3}$ | Kinetic fit |
| IgG (SAb) | | | | |
| FcγRI (CD64) | 19.1 nM ± 3.2 | $1.0 \times 10^5$ | $1.9 \times 10^{-3}$ | Kinetic fit |
| FcγRIIa (CD32a) | 535.0 nM ± 281.7 | n/a | n/a | Steady state |
| FcγRIIb/c (CD32b/c) | 5.3 μM ± 0.6 | n/a | n/a | Steady state |
| FcγRIIIa (CD16a) | 1.3 μM ± 0.09 | $1.6 \times 10^5$ | $2.0 \times 10^{-1}$ | Kinetic fit |
| FcRn | 1.7 nM ± 0.1 | $2.0 \times 10^6$ | $3.4 \times 10^{-3}$ | Kinetic fit |

Figure 4:
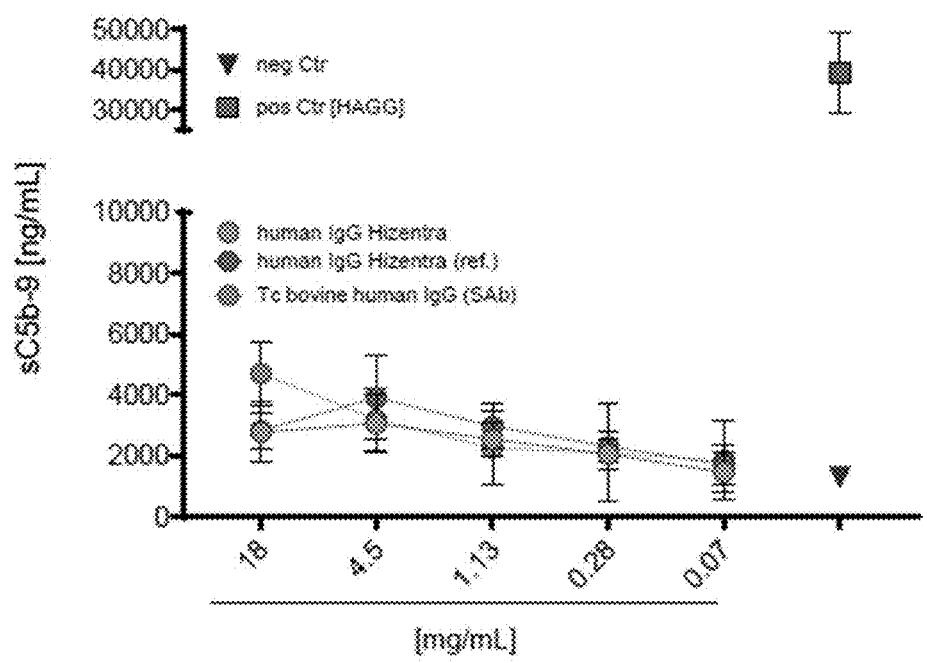
FIG. 4 shows a complement assay comparing TcB-derived product to human-derived polyclonal immunoglobulin product.

Complement activation was assessed by detecting sC5b-9 by ELISA in whole blood. Blood was incubated in the present of polyclonal immunoglobulin for two hours at 37° C., 25 mM. EDTA is added to stop the reaction (Complement activation is Ca2+ and Mg2+ dependent). Heat aggregated IgG (HAGG) was used as positive control for complement activation. Activation is measured by analyzing complement fragments as sC5b-9 by ELISA. No statistical difference was observed between human-derived and TcB samples (FIG. 4).

Figure 5A:
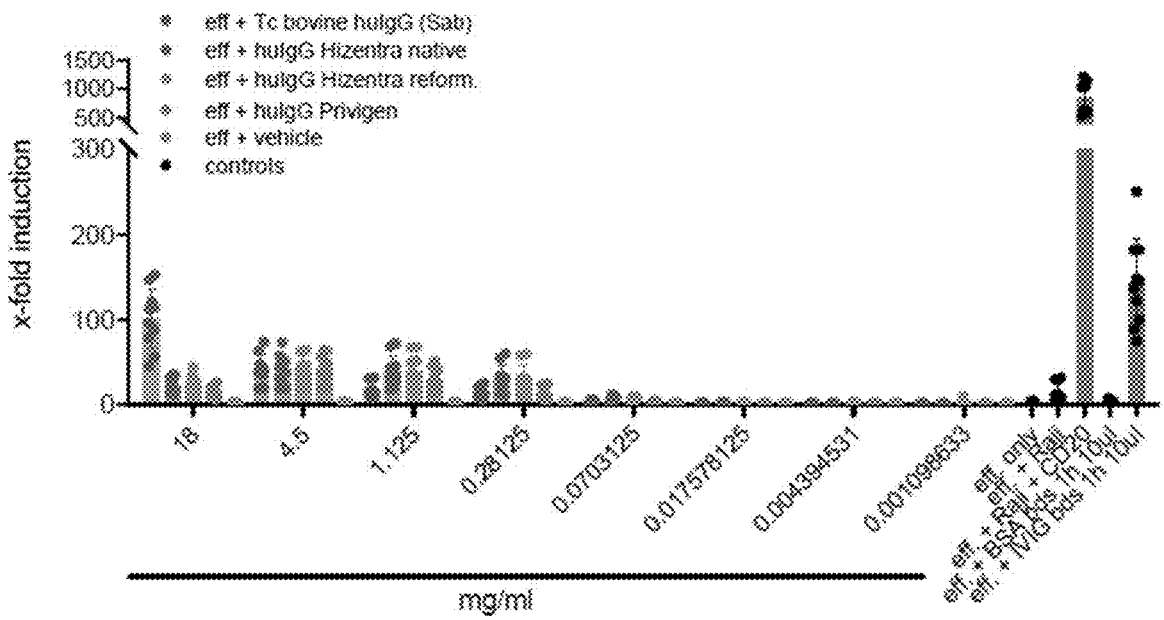
FIG. 5A shows a bar graph of CD16A-mediated signaling in TcB-derived product compared to human-derived product.
Figure 5B:
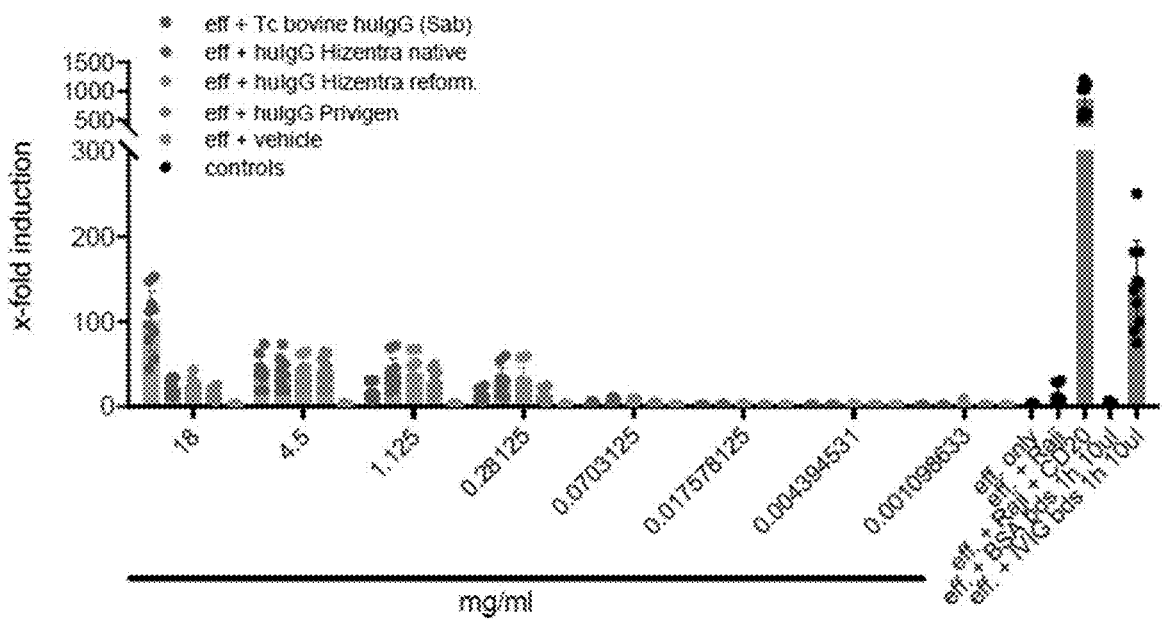
FIG. 5B shows a bar graph of CD32A-mediated signaling in TcB-derived product compared to human-derived product.

Antibody-dependent cellular cytotoxicity (ADDC) was assayed by detecting CD16A-mediated signaling with an ADCC iLite assay (FIG. 5A) and CD32A-mediated signaling using an assay from Promega® (FIG. 5B). No statistical difference was observed between human-derived and TcB samples.

Figure 6A:
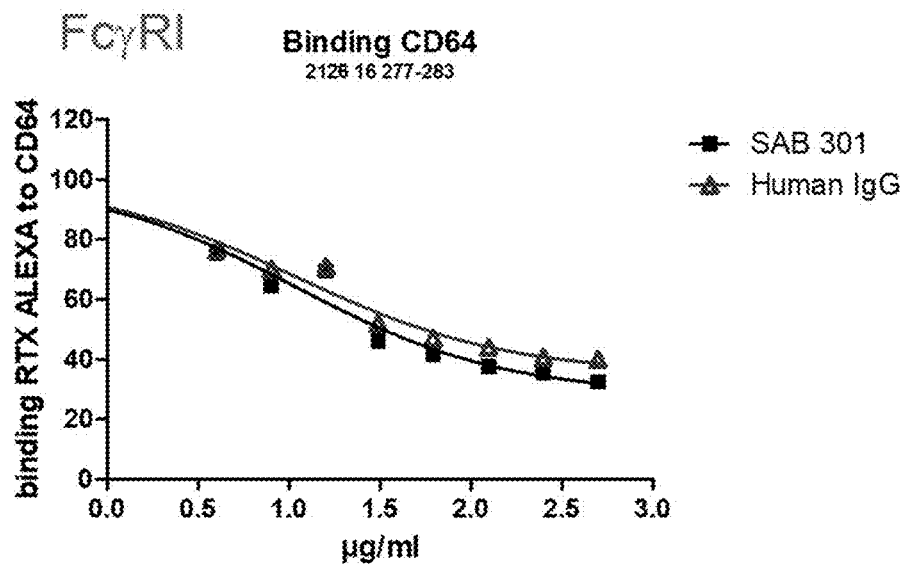
FIG. 6A shows a plot of concentration-dependent binding of TcB-derived product or human-derived product to FcγRI (CD64).
Figure 6B:
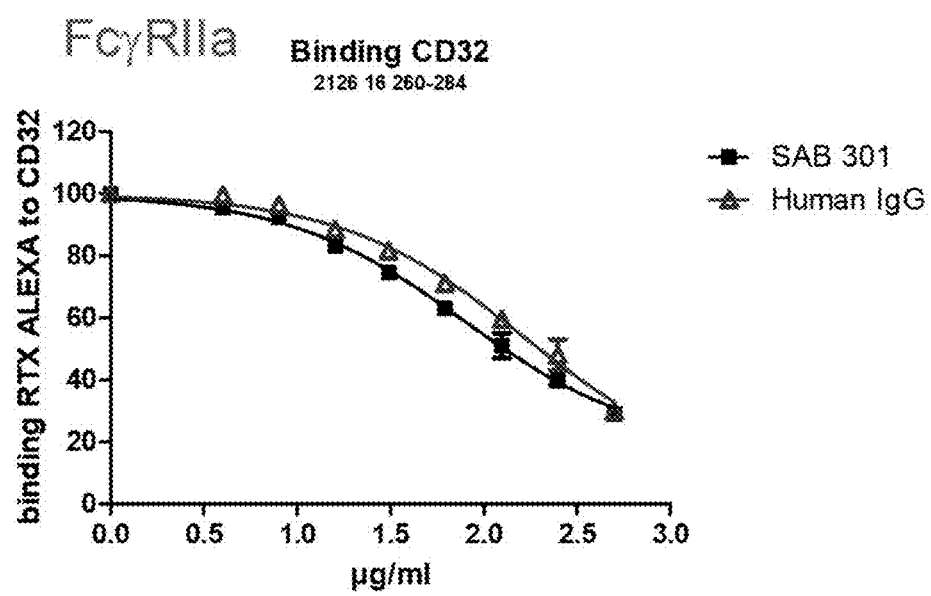
FIG. 6B shows a plot of concentration-dependent binding of TcB-derived product or human-derived product to FcγRIIa (CD32).
Figure 6C:
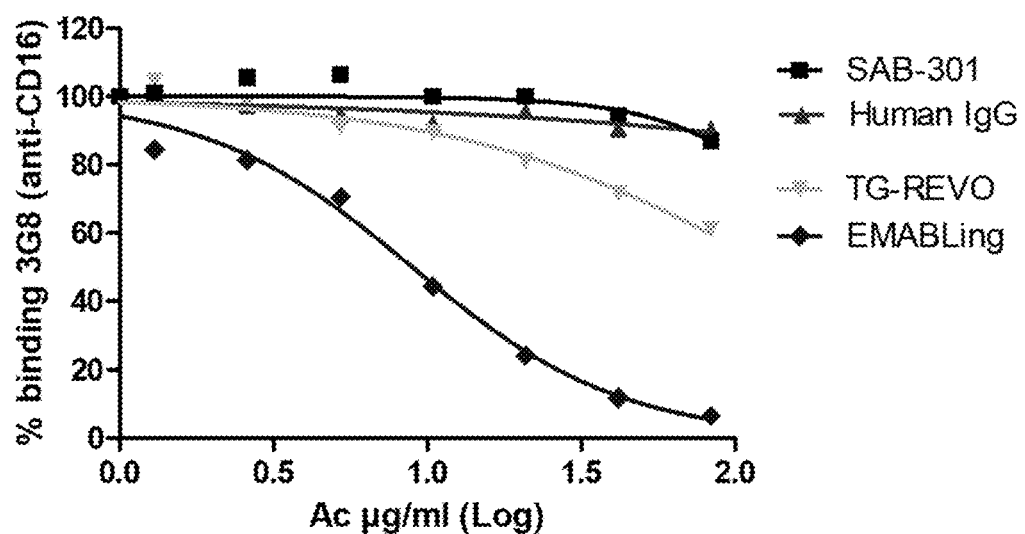
FIG. 6C shows a plot of concentration-dependent binding of TcB-derived product or human-derived product to FcγRIIIa (CD16). EMABLig is a low-fucose monoclonal antibody and TG-REVO is the glycol-modified monoclonal antibody, both engineered to have increased binding to FcγRIIIa compared to human immunoglobulin.
Figure 6D:
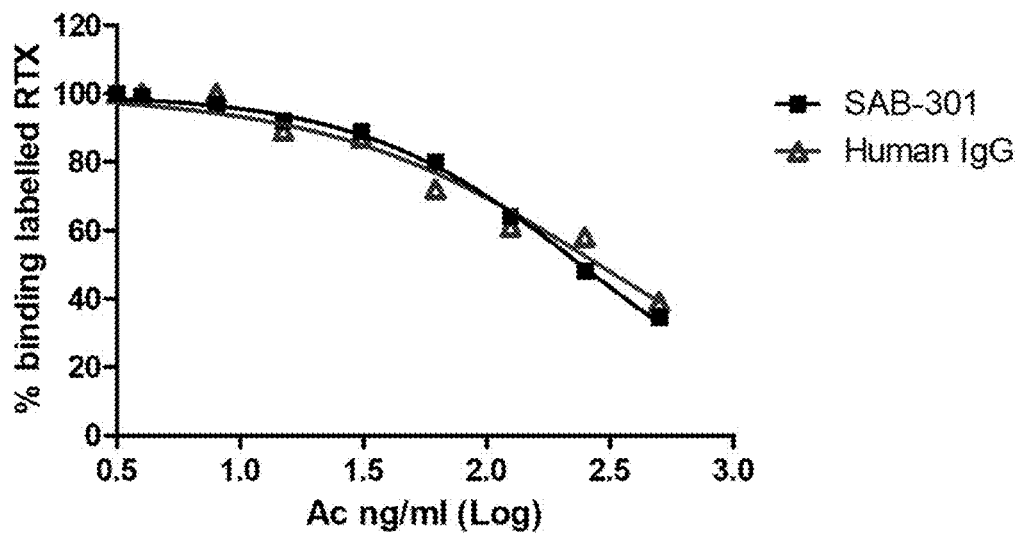
FIG. 6D shows a plot of concentration-dependent binding of TcB-derived product or human-derived product to FcγRn.

Further data demonstrating similar levels of human Fc gamma receptor binding is provided in FIGS. 6A-6B.

Figure 7A:
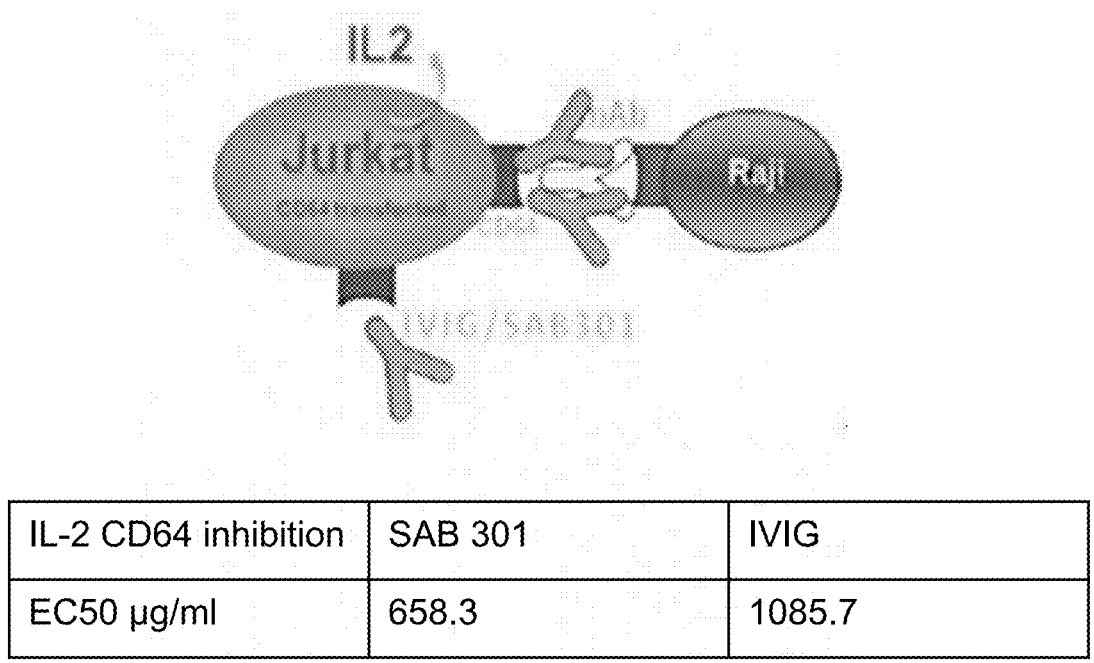
FIG. 7A shows a pictorial representation of an IL-2 production assay.
Figure 7B:
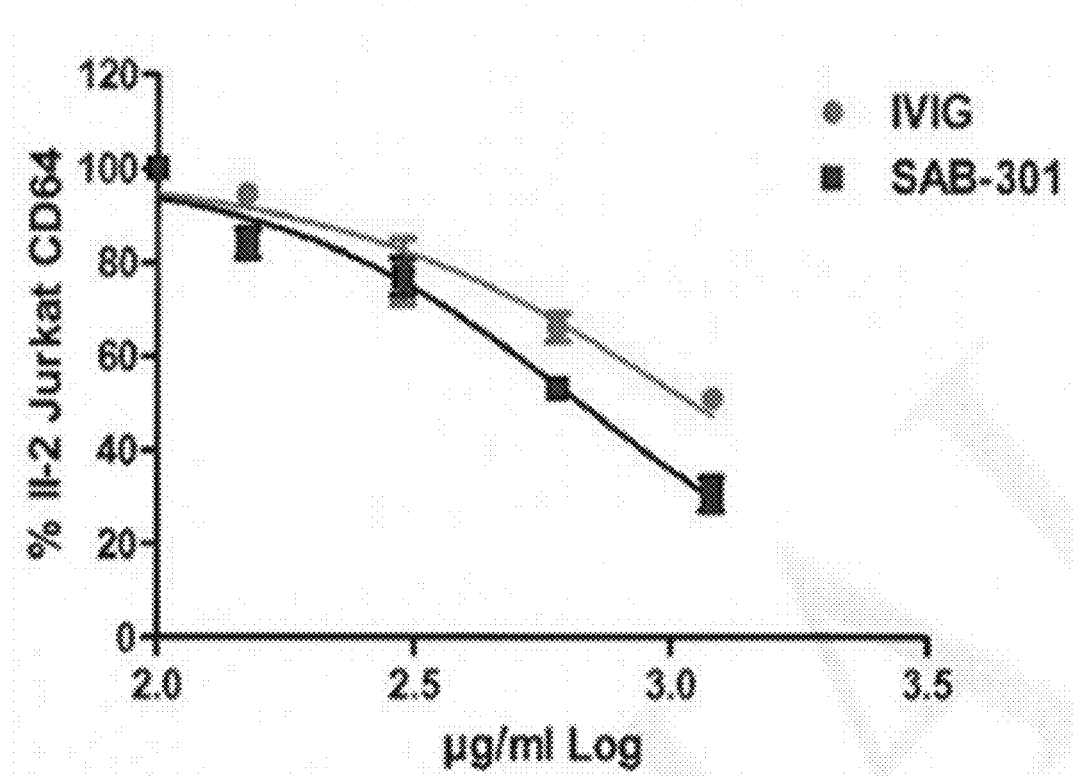
FIG. 7B shows a plot of concentration-dependent inhibition of IL-2 production by TcB-derived immunoglobulin ("SAB-301") or human-derived immunoglobulin ("IVIG").

Inhibition of IL-2 production produced by Jurkat-CD64 in the presence of Raji and anti-CD20 Rituxan was also tested. TcB-derived product demonstrated slightly better inhibition of immune complex interaction with effector cells specifically inhibition of IL-2 production compared to human IgG (FIG. 7).

Glycosylation of TcB-Produced Human Polyclonal Immunoglobulin

Reduction of fucosylation leads of IgG1 have been shown to increased macrophage activation and lung epithelial damage in COVID-19 patients.

Applicants have discovered that, unlike convalescent serum, the ungulate-derived polyclonal immunoglobulin described here, while having a fully human antibody sequence, maintains higher fucosylation. The TcB system maintains high fucosylation at 94% comparable to normal human IgG1 fucosylation level, but distinct from the fucosylation levels observed in human-derived hIgG1 specific to SARS-CoV-2. The disclosure therefore provides a unique method to obtain highly fucosylated human immunoglobulin for treatment of COVID, such as COVID-19 or disease cause by future coronavirus strains. Normal levels of IgG1 fucosylation (e.g., ~94%) distinguish this therapy from others as they may avoid strong activation of ADCC and effector cell function that could lead to epithelial lung tissue damage.

Additionally, TcB-derived produce contains NGNA, which distinguishes the product from human-derived products.

Table 6 provides the glycosylation profile of the TcB-derived product determined by mass spectrometry.

TABLE 6

| Glycosylational features | % |
|---|---|
| Sialylated structures | 14.0 |
| α-Gal structures | 2.3 |
| N-glycolyneuraminic (NG)-cont. Structures | 13.8 |
| N-acetylneuraminic (NA)-cont. Structures | 0.2 |
| Core-fucosylated structures | 94.4 |
| Bisected structures | 14.5 |
| Highmannose structures | 2.9 |
| Hybrid structures | 1.4 |
| Complex structures | 95.7 |

Table 7 compares the NGNA content of the TcB-derived product to human-derived product. Sialic Acid analysis indicates TcB-produced hIgG has >90% NGNA. The only impact expected of NGNA would be higher clearance but prior clinical work demonstrates that TcB-derived product has a half-life of 28 days, the same as human-derived hIgG1.

TABLE 7

| Sample name | NGNA contents | NANA content |
|---|---|---|
| human IgG from #468 | 0.90 | 0.04 |
| Chimeric IgG from #468 | 0.71 | 0.03 |
| Bovine IgG | 0.64 | 0.12 |
| Human IVIG | 0.00 | 0.72 |
| KRN330 (mAb)* | 0.03 | 0.13 |
| NESP* | 0.2 | 20 |

Example 2

Safety, Tolerability, and Pharmacokinetics of SAB-185 in Healthy Participants

Coronavirus disease 2019 (COVID-19) is an infectious disease caused by severe acute respiratory syndrome coronavirus 2 (SARS-CoV-2). SAB Biotherapeutics has developed SAB-185, an Anti-SARS-CoV-2 Human Immunoglobulin Intravenous (transchromosomic [Tc] bovine-derived), as a potential therapeutic to treat COVID-19. This study will evaluate the safety, immunogenicity, and pharmacokinetics of SAB-185 in healthy participants.

Five cohorts received escalating dose levels or product, or placebo:
- 10 mg/kg SAB-185 in normal (0.9%) saline; concentration 4 mg/mL (0.4%)
- 25 mg/kg SAB-185 in normal (0.9%) saline; concentration 20 mg/mL (2%)
- 25 mg/kg SAB-185 in normal (0.9%) saline; concentration 20 mg/mL (2%). Cohort 3 will receive a second 25 mg/kg dose of SAB-185 7 days (+/−2) after the first treatment.
- 50 mg/kg SAB-185 in normal (0.9%) saline; concentration 20 mg/mL (2%)
- Normal (0.9%) saline in approximately the same volume as each cohort in the experimental drug arm.

Primary outcome measures are:
- Number of Participants Having Adverse Events [Time Frame: 29 Days]

Incidence and severity of other adverse events and severe adverse events (SAE)
Number of Participants Having Transfusion-Related Adverse Events [Time Frame: 29 Days]
Transfusion-related adverse events
Secondary outcome measures are:
Number of Participants Having Adverse Events [Time Frame: 90 Days]
Incidence and severity of adverse events and SAEs from Screening through Study Day 90
Pharmacokinetics from screening to day 90 [Time Frame: 90 Days]
SARS-CoV-2 binding (ELISA) and neutralizing (PRNT80) antibody titers from Screening through Study Day 90

Safety, Tolerability, and Pharmacokinetics of SAB-185 in Ambulatory Participants with COVID-19

Coronavirus disease 2019 (COVID-19) is an infectious disease caused by severe acute respiratory syndrome coronavirus 2 (SARS-CoV-2). SAB Biotherapeutics has developed SAB-185, an Anti-SARS-CoV-2 Human Immunoglobulin Intravenous (transchromosomic [Tc] bovine-derived), as a potential therapeutic to treat COVID-19. This study will evaluate the safety, immunogenicity, and pharmacokinetics of SAB-185 in ambulatory participants with COVID-19.

SAB-185 is a purified human immunoglobulin G (hIgG) designed to specifically bind to Severe Acute Respiratory Syndrome Coronavirus 2 (SARS-CoV-2) viruses. SAB-185 is purified from the plasma of immunized Tc bovines that were immunized initially (vaccinations 1 and 2) with a plasmid DNA (pDNA) vaccine that expresses wild-type SARS-CoV-2 spike protein, followed by additional immunizations (vaccinations 3 and beyond) with a recombinant spike protein from SARS-CoV-2 produced in insect cells. The purified hIgG is a sterile liquid formulated in 10 mM glutamic acid monosodium salt, 262 mM D-sorbitol, 0.05 mg/mL Tween 80, pH 5.5. The drug product will be administered intravenously and will be diluted in saline per the clinical protocol.

Four cohorts received escalating dose levels or product, or placebo:
10 mg/kg SAB-185 in normal (0.9%) saline; concentration 4 mg/mL (0.4%)
25 mg/kg SAB-185 in normal (0.9%) saline; concentration 20 mg/mL (2%)
50 mg/kg SAB-185 in normal (0.9%) saline; concentration 20 mg/mL (2%)
Normal (0.9%) saline in approximately the same volume as each cohort in the experimental drug arm.
Primary Outcome Measures are:
Number of Participants Having Adverse Events [Time Frame: 29 Days]
Incidence and severity of other adverse events and severe adverse events (SAE)
Number of Participants Having Transfusion-Related Adverse Events [Time Frame: 29 Days]
Transfusion-related adverse events
Secondary outcome measures are:
Number of Participants Having Adverse Events [Time Frame: 90 Days]
Incidence and severity of adverse events and SAEs from Screening through Study Day 90
Assessment of the PD of SAB-185 administered intravenously [Time Frame: 90 Days]
Measurement of SARS CoV-2 neutralizing (PRNT80) antibody titers from screening through Study Day 90
Immune response elicited by SAB-185 [Time Frame: 90 Days]
Measurement of Rheumatoid factor through day 90
Concentration of subject anti-SAB-185 antibodies elicited by SAB-185 [Time Frame: 90 Days]
Measurement of anti-SAB-185 antibodies through screening day 90
Incidence of SARS-CoV-2 in oropharyngeal (OP) or nasopharyngeal (NP) swab specimens [Time Frame: 29 Days]
Incidence of SARS-CoV-2 in swab specimens as measured by quantitative RT-PCR through Study Day 29
Level of SARS-CoV-2 in oropharyngeal (OP) or nasopharyngeal (NP) swab specimens [Time Frame: 29 Days]
Level of SARS-CoV-2 in swab specimens as measured by quantitative RT-PCR through Study Day 29

Example 3

SAB-185 In Vitro Evaluation Against VSV-SARS-CoV-2 Mutants

Four mutants of concern including (D614G, N501Y, S477N and E484K) are currently highly circulating in humans In this study, we used VSV-SARS-CoV-2 and SAB-185, which was purified from transchromosomic (Tc) bovines hyperimmunized with two doses of plasmid DNA encoding the Wuhan strain S gene and followed by repeated doses of recombinant S protein, to evaluate the ability of SAB-185 to neutralize the wild-type SARS-CoV-2 (D614G variant) and chimeric vesicular stomatitis virus (VSV) SARS-CoV-2 reporter viruses in vitro with Wild-type and D614G, S477N, E484K, and N501Y S protein substitutions in comparison to a neutralizing receptor-binding-domain (RBD) monoclonal to the SARS-CoV-2 Wuhan-Hu-1 S protein.

The genome of transchromosomal (Tc) bovines contains a human artificial chromosome (HAC) comprising the entire human Ig gene repertoire (human Ig heavy chain [IgH] and human kappa light chain) that reside on 2 different human chromosomes (hChr), specifically the IgH locus from hChr14 and the Immunoglobulin kappa (Igk) locus from hChr2. The system maintains the ability to use the genetic information provided by the immunoglobulin gene repertoires for generating a wide diversity of human polyclonal antibodies (pAbs). Fully hIgG (hIgG/hIgκ) can then be produced in these Tc bovines after vaccination with suitable antigens, and these animals produce up to 15 g/L of IgG antibodies in their plasma (similar to humans which have 7-16 g/L IgG). Using this approach polyclonal sera against a swath of emergent threats to humans have been developed and established as safe.

Results

Generation of Human Immunoglobulin Against SARS-CoV-2 Spike in Transchromosomic Bovines.

To generate anti-SARS-CoV-2 polyclonal human immunoglobulin SAB-185, we primed transchromosomic (Tc) bovines with a DNA encoding the Wuhan-Hu-1 strain Spike (S) gene (Wu et al. *Nature* 579:265-69 (2020)). SARS-CoV-2 spike protein for the first vaccination (V1) and the second vaccination (V2) at a 3-week interval, followed by 3 subsequent boosts with recombinant spike ectodomain produced and purified from insect cells for the third vaccination (V3) to the fifth vaccination (V5) at a 4-week interval. Plasma was collected on 8, 11 and 14 days post each booster from V3 to V5. Then the qualified plasma was pooled and subjected to cGMP purification for human IgG SAB-185.

SAB-185 Lot 1 and Lot 5 were purified from pooled V3 plasma and V4 plasma, respectively. SAB-185 Lot 6 was purified from pooled V3, V4 and V5 plasma.

Effect of SAB-185 on Neutralization of VSV-SARS-CoV-2.

Figure 8A:
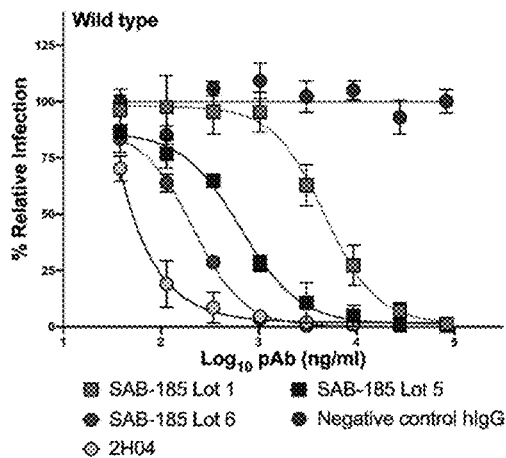
FIGS. 8A-8C. Neutralization of VSV-SARS-CoV-2 mutants by polyclonal antibody.

Here using a neutralization assay based on VSV-SARS-CoV-2, we evaluated the ability of SAB-185 to inhibit infection mediated by the S protein. We incubated VSV-SARS-CoV-2 with increasing concentrations of SAB-185 for 1 h at 37° C. and measured residual infectivity on Vero E6 cells. We observed effective neutralization, with an approximate $IC_{50}$ of 4728 ng/ml for SAR-185 Lot 1, 649.1 ng/ml for SAR-185 Lot 5 and 211.9 ng/ml for SAB-185 Lot 6, which compares to neutralization by potent monoclonal antibodies such as 2H04. (FIG. 8A).

Figure 8B:
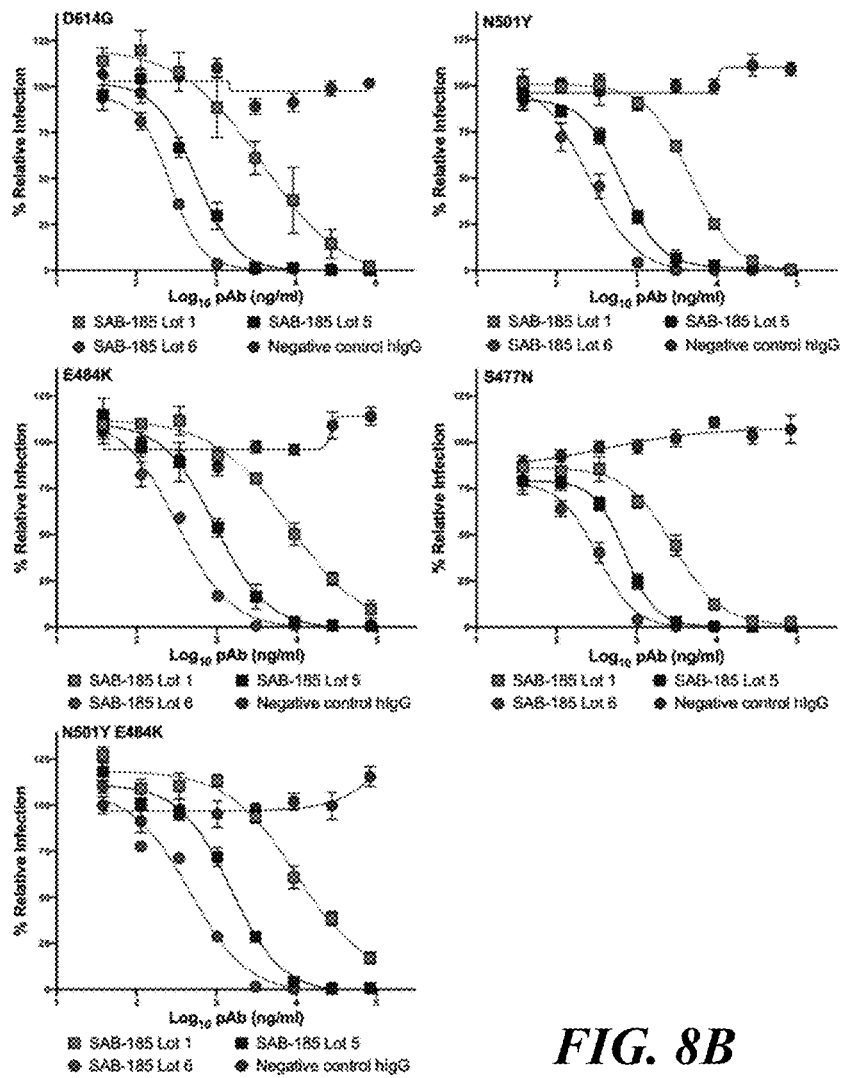
Figure 8C:
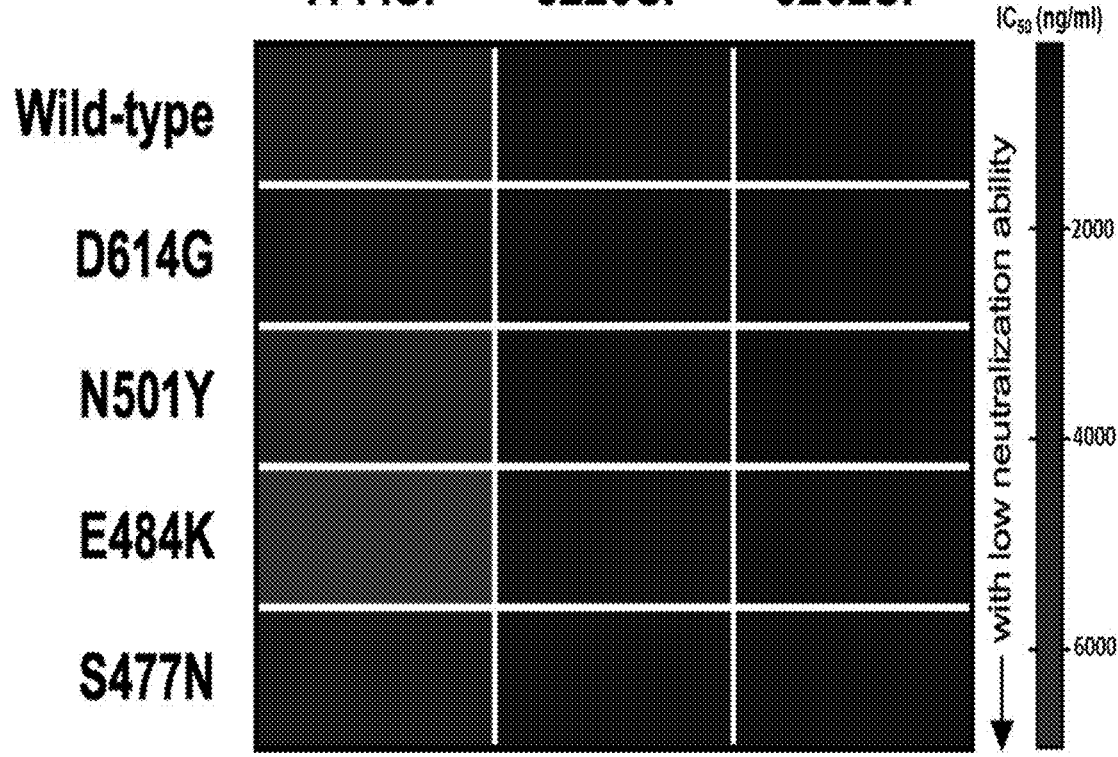

Using monoclonal antibodies, we previously selected >50 mutants in SARS-CoV-2 spike that exhibit resistance to specific monoclonal antibodies. Among those mutants were S477N and E484K which exhibit resistance to multiple antibodies and are present in emerging variants of concern. We also generated the dominant D614G, and the mouse adapted N501Y variants. To determine whether the potency of SAB-185 was altered by any of these individual amino acid substitutions in spike, or the double mutant N501Y E484K, we performed neutralization assays. We incubated each of the indicated VSV-SARS-CoV-2 mutants with increasing concentrations of SAB-185 for 1 h at 37° C. and measured residual infectivity on Vero E6 cells (FIG. 8B). FIG. 8C is a heat map of the same data. All four mutants were dose-dependently inhibited by SAB-185, at levels that were similar to those seen for wild type spike. This data demonstrates that SAB-185 had equivalent neutralizing ability to D614G, N501Y, S477N and E484K mutants that are present in circulating human isolates of SARS-CoV-2.

Selection of SAB-185 Escape Mutants

Figure 9A:
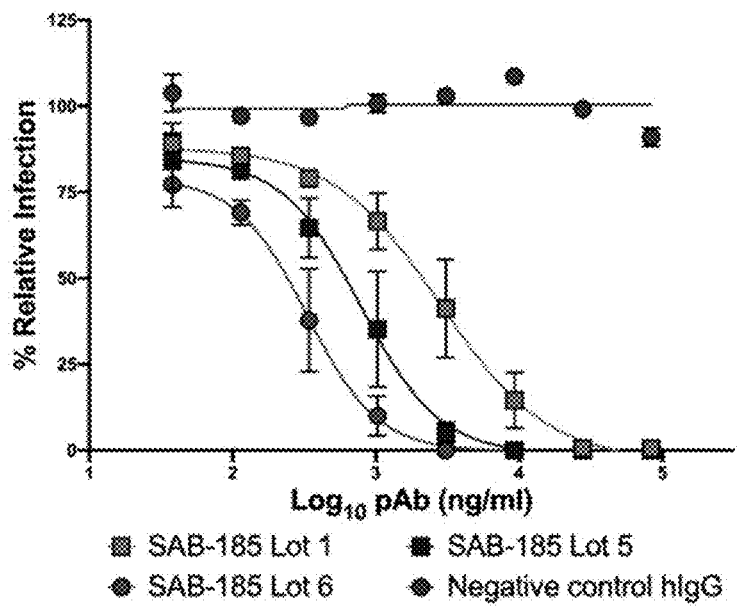
FIGS. 9A-9B. Selection of SAB-185 pAbs escape.
Figure 9B:
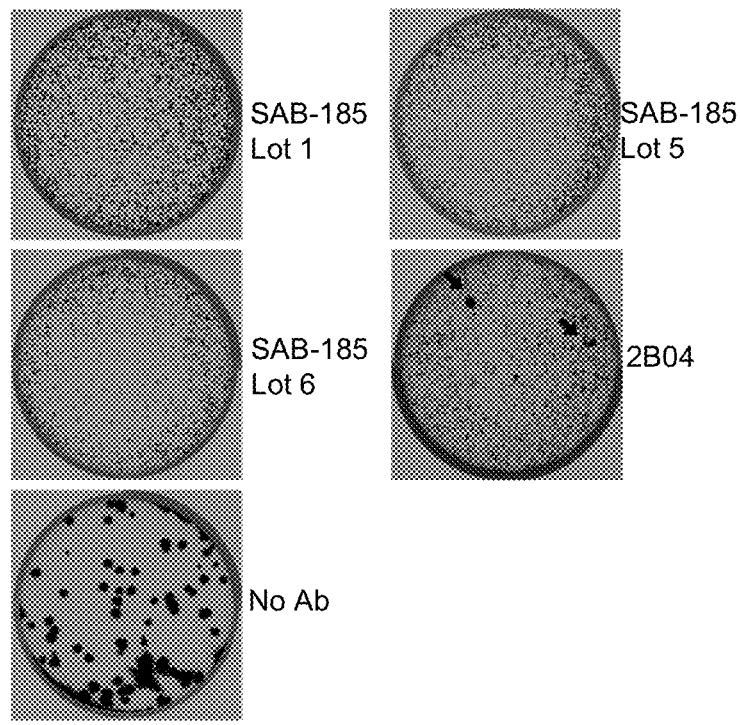
Figure 10:
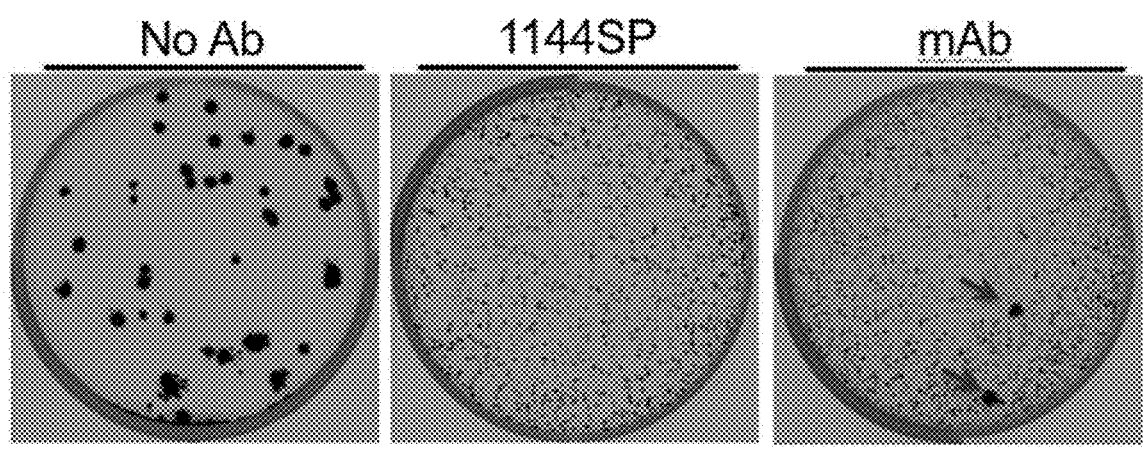
FIG. 10 shows selection for VSV-SARS-CoV-2 E484K escape mutation from SAB-185 vs. mAb. When tested 4 6-well plates: Escape mutants are found from mAb. No escape clone is found from SAB-185 Lot1 confirming that SAB-185 as pAb is superior to mAb against escape mutants.

Taking advantage of the intrinsically error prone nature of the VSV RNA dependent RNA polymerase we and others have previously isolated VSV-SARS-CoV-2 S gene mutants by selection using mAbs and human convalescent serum. SAB-185 and a negative control hIgG were tested for neutralizing activity against VSV-SARS-CoV-2 at the MOI of 1. The concentration of SAB-185 added in the overlay completely inhibited viral infection (FIG. 9A). In contrast to the ability to readily isolate mAb and serum escape mutants, we were unable to isolate mutants resistant to the human immunoglobulin SAB-185 (FIG. 9B). Taken together, this analysis suggests that natural cocktails of pAbs binding distinct epitopes on SARS-CoV-2 S protein pose a barrier to immune escape.

Experimental Model and Subject Details

Cells. Cells were cultured in humidified incubators at 34° or 37° C. and 5% $CO_2$ in the indicated media. Vero CCL81, Vero E6 and Vero E6-TMPRSS2 were maintained in DMEM (Corning or VWR) supplemented with glucose, L-glutamine, sodium pyruvate, and 10% fetal bovine serum (FBS). MA104 cells were propagated in Medium 199 (Gibco) containing 10% FBS. Vero E6-TMPRSS2 cells were generated using a lentivirus vector described as previously (6).

VSV-SARS-CoV-2 mutants. VSV-SARS-CoV-2 was described as previously (6). S477N and E484K were escape mutants isolated from mAbs described as previously (7). N501Y and D614G were constructed using SARS-CoV-2 Wuhan-Hu-1 spike with substitution at N501 or D614 site respectively and rescued by using reverse genetic system. Virus were then plaque purified and the mutations were identified by Sanger sequencing (GENEWIZ). Viral stocks were amplified on MA104 cells at an MOI of 0.01 in Medium 199 containing 2% FBS and 20 mM HEPES pH 7.7 (Millipore Sigma) at 34° C. Viral supernatants were harvested upon extensive cytopathic effect and clarified of cell debris by centrifugation at 1,000×g for 5 min. Aliquots were maintained at −80° C.

Method Details

Plaque assays. Plaque assays were performed on Vero and Vero E6-TMPRSS2 cells. Briefly, cells were seeded into 6 well plates for overnight. Virus was serially diluted using DMEM and cells were infected at 37° C. for 1 h. Cells were cultured with an agarose overlay in the presence of Ab or absence of Ab at 34° C. for 2 days. The concentration of SAB-185 pAbs added in the overlay completely inhibited viral infection. Plates were scanned on a biomolecular imager and expression of eGFP is show at 48 hours post-infection.

Neutralization assays using a recombinant VSV-SARS-CoV-2 and mutants. Briefly, the initial dilution of started at 83 μg/mL and was three-fold serially diluted in 96-well plates over eight dilutions. Indicated dilutions of SAB-185 pAbs were incubated with $10^2$ PFU of VSV-SARS-CoV-2 and mutants for 1 h at 37° C. SAB-185 pAb-virus complexes then were added to Vero E6 cells in 96-well plates and incubated at 37° C. for 7.5 h. Cells were fixed at room temperature in 2% formaldehyde containing 10 μg/mL of Hoechst 33342 nuclear stain for 45 min. Fixative was replaced with PBS prior to imaging. Images were acquired using an In Cell 2000 Analyzer automated microscope (GE Healthcare) in both the DAPI and FITC channels to visualize nuclei and infected cells (×4 objective, 4 fields per well). Images were analyzed using the Multi Target Analysis Module of the In Cell Analyzer 1000 Workstation Software (GE Healthcare). GFP-positive cells were identified using the top hat segmentation method and counted within the InCell Workstation software.

Quantification and Statistical Analysis

All statistical tests were performed as described in the indicated figure legends. Non-linear regression (curve fit) was performed for FIGS. 8A-8B and FIG. 9A using Prism 9.0. The number of independent experiments used are indicated in the relevant Figure legends.

Example 4

Intramuscular Anti-SARS-CoV-2 Immunoglobulin from Transchromosomic Bovines Protects K18 Transgenic Mice Against Live Virus Challenge An anti-SARS-COV-2 product (SAB-185) was produced. SAB-185 was evaluated in a Phase 1 healthy volunteer clinical trial and a Phase 1b ambulatory COVID-19 patient clinical trial using the IV route of administration up to 50 mg/kg [clinicaltrial.gov; NCT04469179, NCT04468958 respectively]. SAB-185 was safe, well-tolerated and non-immunogenic in healthy and COVID-19-infected volunteers (manuscript in preparation). Next a SARS-CoV-2 live virus challenge study in K18 transgenic mice expressing human ACE2 receptors was performed.

To evaluate pre-exposure effectiveness, two groups of K18 mice (n=12 per group) were given IM injections of either a low or high dose of SAB-185 and then challenged 12 hours later with a sub-lethal dose of SARS-COV-2 administered intranasally. To evaluate post-exposure effectiveness, two groups of K18 mice (n=12 per group) were treated with IM administered SAB-185 at either six or 24-hours after sub-lethal virus intranasal challenge. A fifth group of infected saline treated K18 mice served as control (n=12). IM administration of SAB-185 was highly effective in preventing SARS-COV-2 infection. A separate experiment evaluated the effectiveness of SAB-185 against lethal challenge doses of SARS-COV-2. Two groups of K18 mice (n=5) were treated with IM SAB-185 either 12 hours prior to or 6 hours after intranasal SARS-COV-2 challenge. A group of infected saline treated K18 mice (n=5) served as control. All treated mice survived compared to 1 of 5 untreated controls. These results show that SAB-185 is effective as pre- and post-exposure prophylaxis in K18 mice when administered by IM injection. These results support further clinical testing in humans to prevent COVID-19 disease.

Results

Efficacy of SAB-185 in Reducing SARS-CoV-2 Viral Load after Challenge

Figure 11A:
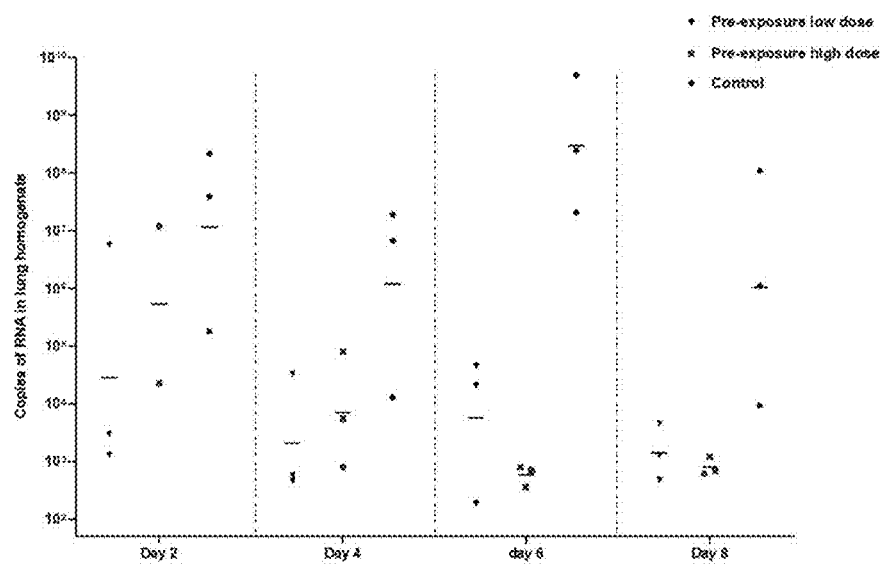
FIGS. 11A-11B shows droplet digital RT-PCR (ddRT-PCR) results from mice administered high (3.75 mg) and low (1.75 mg) dose SAB-185 12 hours prior to intranasal SARS-CoV-2 challenge. Black triangles represent low dose treated animals, red squares high dose treated animals and blue circles saline treated control mice. X-axis indicates the day euthanasia and necropsy and the Y-axis RNA copy number. Lines represent geometric mean RNA copy number of the three animals in that group. (A) Data presented by group and day of euthanasia. (B) Data presented by group; **=$P<0.0001$
Figure 11B:
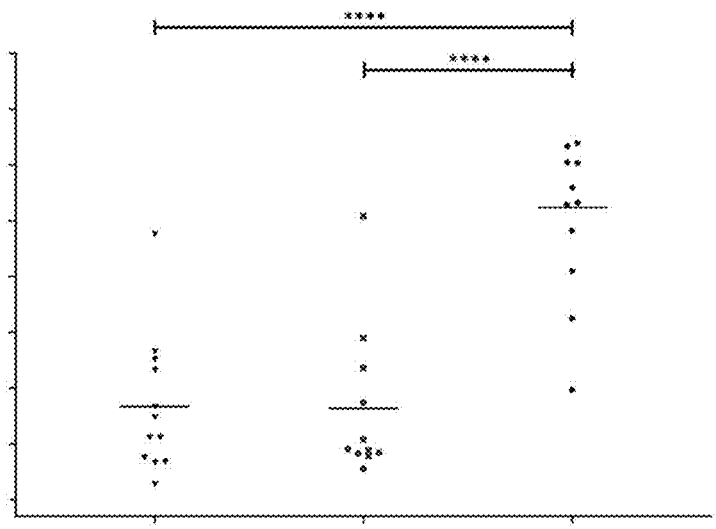

Five groups (n=12 each) of K18 transgenic mice were treated with low (1.87 mg) and high (3.75 mg) doses of SAB-185 before (pre-exposure) or with high dose SAB-185 six and 24 hours after (post-exposure) intranasal challenge with live SARS-CoV-2 virus. Within each group, three mice were euthanized at days 2, 4, 6 and 8 post-challenge. At the time of euthanasia, blood samples were obtained, and lungs, nasal turbinate, brain, liver, kidney and heart removed for analysis. Lung tissue was evaluated for the presence of SARS-Cov-2 by ddRT-PCR and virus isolation to assess the systemic antiviral effects of SAB-185 post-IM administration. FIG. 11A shows the copy number of SARS-CoV-2 RNA present in lung tissue at the various time points from animals in pre-exposure groups. At all time points, groups treated with low or high dose of SB-185 showed lower geometric mean viral RNA copy numbers compared to control saline treated group. Because there were only 3 animals at each time point, a statistical analysis was not done. FIG. 11B shows the ddRT-PCR results for all animals (n=12) in the high and low dose pre-exposure groups compared to the control animals. The geometric mean RNA copy numbers for both pre-exposure groups were similar and significantly lower (p<0.0001) than the geometric mean RNA copy number for the control saline treated mice, demonstrating the effectiveness of pre-exposure IM SAB-185 treatment.

Figure 12A:
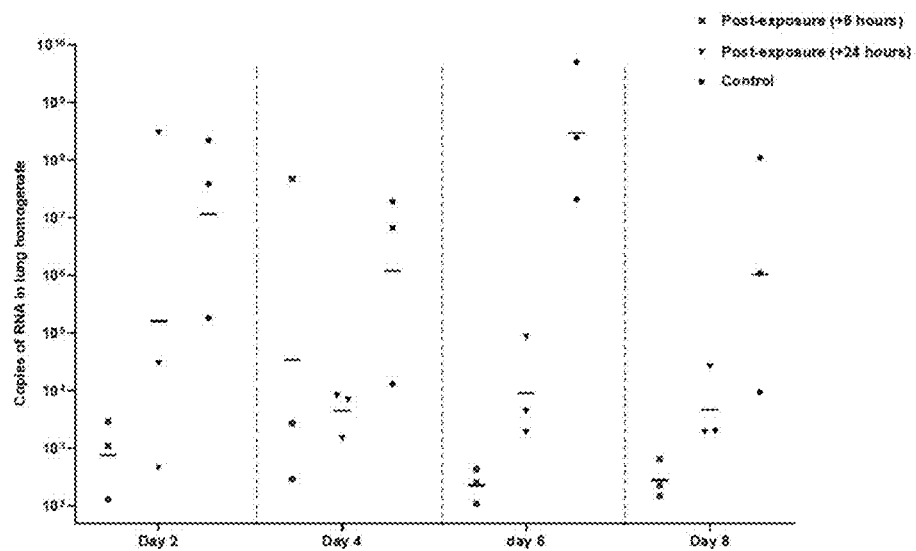
FIGS. 12A-12B shows droplet digital RT-PCR results from mice administered high dose SAB-185 either 6 hours (red squares) or 24 hours (black triangles) after intranasal SARS-CoV-2 challenge. X-axis indicates the day euthanasia and necropsy and the Y-axis RNA copy number. Lines represent geometric mean RNA copy number of the three animals in that group. (A) Data presented by group and day of euthanasia. (B) Data presented by group; **=$P<0.0001$.
Figure 12B:
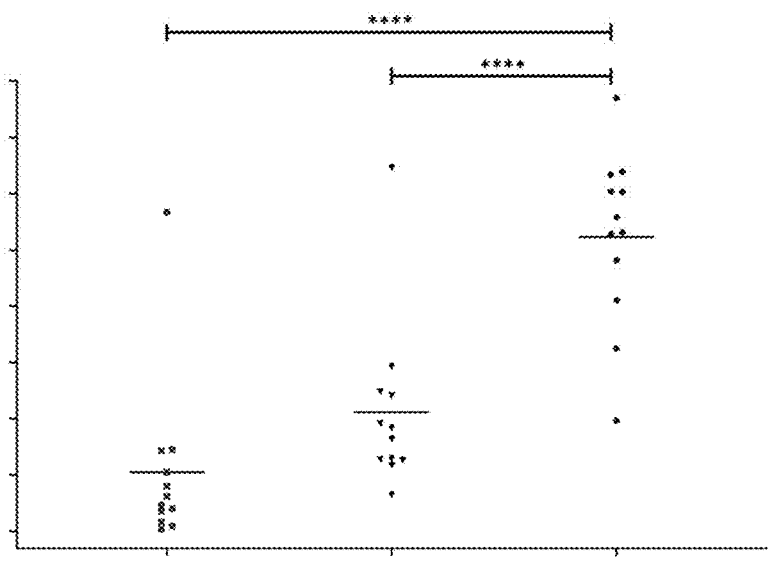

Similarly, the lungs from animals in post-exposure groups (FIG. 12A), which received high dose SAB-185 six and 24 hours after challenge, respectively, showed lower geometric mean SARS-CoV-2 RNA copies at all time points compared to control animals that received saline. FIG. 12B shows the ddRT-PCR results for all animals in each group compared to the control group, irrespective of the time sampled post challenge. The results show that the geometric mean number of SARS-CoV-2 RNA copies was significantly lower than the geometric mean copy number of the saline treated control group (p<0.0001), demonstrating the effectiveness of post-exposure IM SAB-185 treatment.

To evaluate the groups of animals for the presence of live virus in the lungs post-exposure, lung tissue was processed and cultured in VERO81 cells, followed by IFA to detect the presence of SARS-CoV-2. Results are summarized in Table 8. Lung samples from all animals in the low and high dose pre-exposure groups showed no detectable live virus through day 8 post challenge. Similarly, all lung tissues from the 6 hour post-exposure group treated with high dose IM SAB 185 were negative for detectable live virus. Lung samples from four of 12 animals in the 24 hour post exposure SAB-185 treated group had detectable live virus. Of these, two were from specimens taken on day 2 post-challenge and two were from specimens obtained on day 6. Unlike the SAB-185 treated animals, lung tissue from 9 of 12 animals in the control saline treated group had detectable live virus across all time points.

TABLE 8

Lung tissue virus isolation results from treated and untreated mice (# positive/#total).

| Group | Day 2 | Day 4 | Day 6 | Day 8 | Total |
| --- | --- | --- | --- | --- | --- |
| Saline control | 2/3 | 2/3 | 3/3 | 2/3 | 9/12 |
| low dose pre-exposure | 0/3 | 0/3 | 0/3 | 0/3 | 0/12 |
| high dose pre-exposure | 0/3 | 0/3 | 0/3 | 0/3 | 0/12 |
| 6 hour post-exposure | 0/3 | 0/3 | 0/3 | 0/3 | 0/12 |
| 24 hour post-exposure | 2/3 | 0/3 | 2/3 | 0/3 | 4/12 |

Efficacy of SAB-185 on Reducing Organ Pathology after Challenge

Figure 13A:
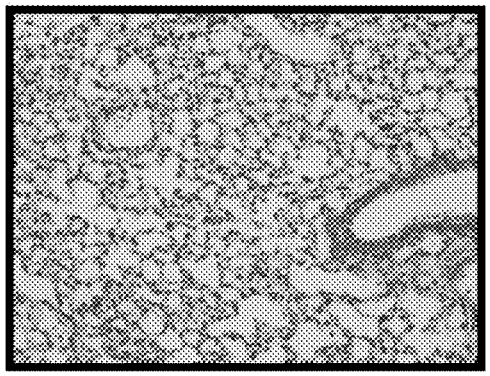
FIGS. 13A-13F show examples of H&E (A, C, E) and immunohistochemical (B, D, F) staining of lung tissue from untreated K18 transgenic mice or mice given SAB-185. A and B are examples of normal lung tissue from animals given SAB-185 12 hours prior to SARS-CoV-2 intranasal challenge. C and D are from an animal euthanized at day 6 post challenge showing mild 1+ to 2+ histopathological changes and immunohistochemical reactivity in the lungs. E and F are examples of lung tissue from untreated control animals showing histopathological changes and immunohistochemical staining consistent with moderate to severe pneumonia. Black arrows represent positive immunohistochemical staining (FIG. 13D and FIG. 13F); and the red arrow indicates perivascular infiltrates (FIG. 13E).
Figure 13B:
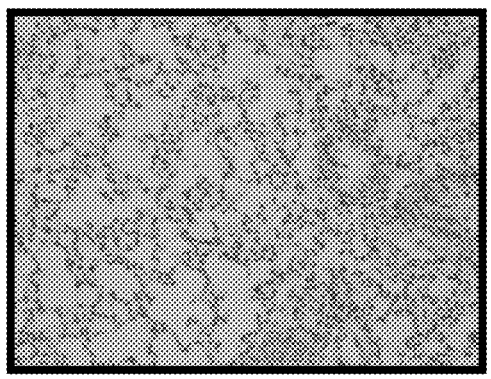
Figure 13C:
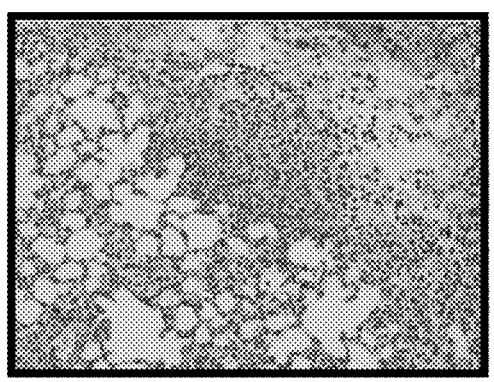
Figure 13D:
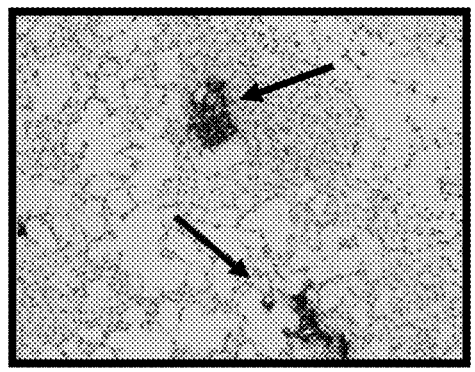
Figure 13E:
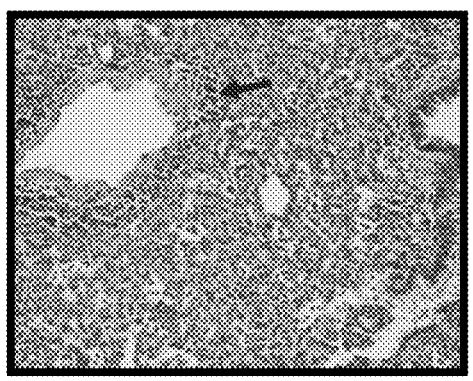
Figure 13F:
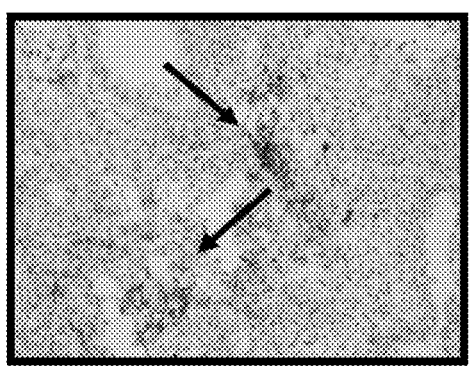

Three mice from each group were euthanized on days 2, 4, 6 and 8 post virus challenge. Nasal turbinate, lung, liver, kidney, heart, and brain tissues were examined by histologic/immuno-histologic staining for organ pathology and scored as described in Table 3. All control saline treated mice except two (one at day 2 and one at day 4) showed 1+ to 3+ histological changes in the lungs up to day 8 post-challenge. Lung tissues showed multifocal perivascular and interstitial mononuclear, eosinophilic infiltrates. Blood vessels demonstrated transmural multifocal mononuclear cells consistent with margination and transmigration of mononuclear leukocytes (FIG. 13E). Alveolar inflammation was also observed showing lymphocytic, histiocytic multifocal infiltrates consistent with interstitial pneumonia. Immunohistochemical staining for the presence of SARS-CoV-2 viral antigen showed multifocal immunoreactivity in the alveolar septa (FIG. 13F). In contrast, lung tissue from SAB-185 treated animals (Pre-Exp low and high dose, Post-Exp 6H and 24H) appeared normal except for one mouse each in the Pre-Exp high dose (day 2), Post-Exp 6H (day 4 and 8) and Post-Exp 24H (day 2 and 6) groups.

When nasal turbinate of animals was examined, all saline treated control mice showed 3+ pathology on day 2 which decreased to 1+ on day 4 and day 6. By day 8, only ⅓ animals showed abnormal histology. In general, the pathology in the nasal turbinates of SAB-185 treated animals were less severe compared to saline treated animals. Pre-exposure low dose group showed a 2+ to 3 pathology on day 2, 1+ on day 4 followed by normal nasal turbinate on days 6 and 8. In the pre-exposure high dose group, mice showed 1+ to 2+ pathology only on day 2. Mice euthanized on days 4, 6 and 8 had normal nasal turbinate. Among the post-exposure treatment groups, all animals except one on day 8 in the 6H post-exposure group showed 1+ to 2+ pathology. Severity was less in the 6 h post-exposure group compared to the 24 h group.

All other organs tested (liver, kidney, heart and brain) showed no infection related pathology in any of the control or SAB-185 treated mice except one control mouse euthanized on day 6. The brain tissue from this animal showed 4+ changes on H&E staining including multifocal, perivascular mononuclear infiltrates affecting the hypothalamus. Mild multifocal vacuolation of neurons affecting the cerebrum and hypothalamus was also observed. Immunohistochemical staining was positive in the olfactory bulbs, cerebrum, hippocampus, thalamus and hypothalamus.

Detection of SAB-185 after IM Administration

Figure 14A:
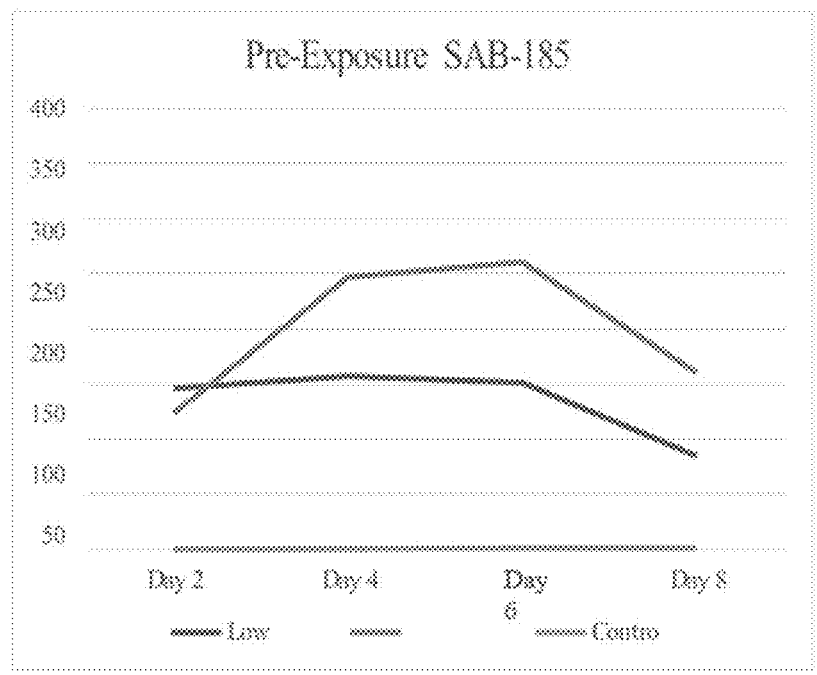
FIGS. 14A-14B show total anti-SARS-CoV-2 IgG antibody. (A) Total antibody expressed as arbitrary units (AU)/ml in animals treated with high and low dose SAB-185 12 hours prior to challenge with SARS-CoV-2. (B) total antibody expressed as AU/ml in animals treated with SAB-185 either six hours or 24 hours after intranasal challenge with SARS-CoV-2.
Figure 14B:
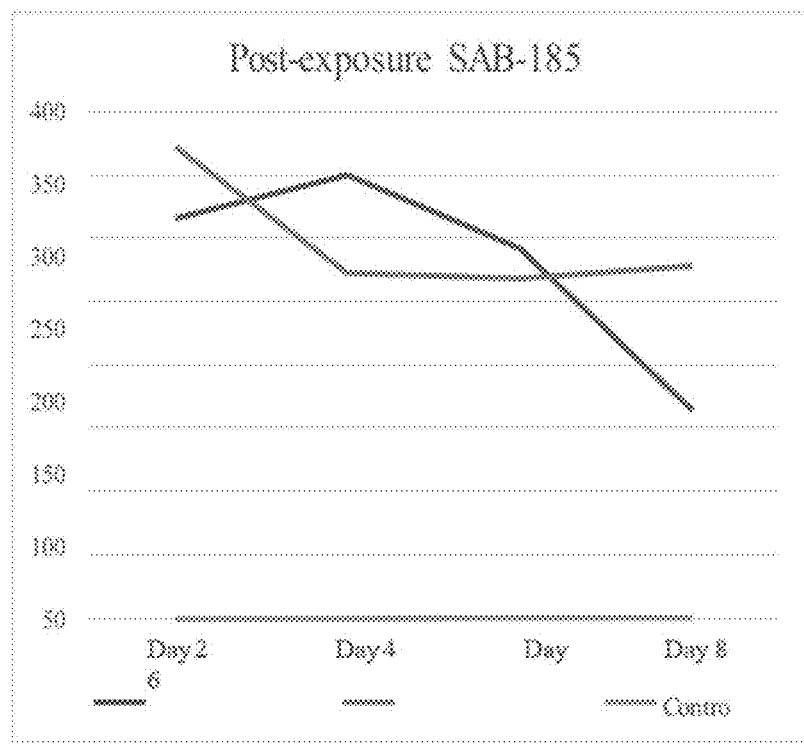

Sera from animals euthanized at the designated time periods were pooled and analyzed for the presence of total human anti-SARS-CoV-2 IgG using a commercially available quantitative ELISA. Any detectable human anti-SARS-CoV-2 IgG was assumed to be representative of SAB-185. FIGS. 14A-14B show that human anti-SARS-CoV-2 antibody was present in the mice treated pre-exposure with either low or high dose of SAB-185 (FIG. 14A) and in those treated 6 h and 24 h post-exposure (FIG. 14B). Anti-SARS-CoV-2 antibody was present in these animals at day 2 post challenge and persisted through day 8 post challenge. In contrast, no detectable antibody was present in control saline treated animals.

cPASS ELISA was utilized as a surrogate to assess anti-SARS-CoV-2 neutralization activity in serum from mice administered IM SAB-185. The 80% neutralizing antibody titer was taken to be the highest dilution resulting in greater than or equal to an 80% reduction in binding to recombinant RBD protein compared to kit negative control samples. It was evident that sera from all SAB-185 treated groups (pre-exposure low and high dose, post-exposure 6 h and 24 h) contained SARS-CoV-2 neutralizing antibody (80% neutralization titer 80-320) at all time points measured during the study. No detectable neutralizing antibody was found in control saline treated group at any point during the study (Table 9).

TABLE 9

SARS-CoV-2 neutralizing antibody
as measured by C-pass ELISA
80% neutralization titer ($NT_{80}$)

|  | Day 2 | Day 4 | Day 6 | Day 8 |
|---|---|---|---|---|
| Saline control | 0 | 0 | 0 | 0 |
| low dose pre-exposure | 160 | 160 | 160 | 80 |
| high dose pre-exposure | 160 | 320 | 160 | 160 |
| 6 hour post-exposure | 320 | 320 | 320 | 160 |
| 24 hour post-exposure | 320 | 160 | 160 | 160 |

Morbidity and Mortality Following Lethal Virus Challenge.

Figure 15A:
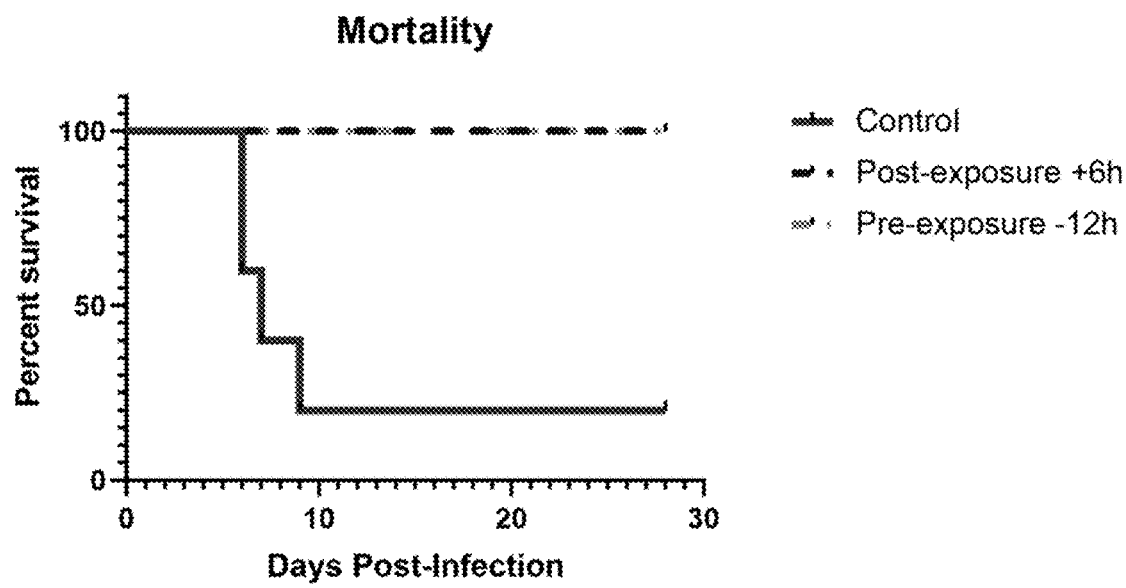
FIG. 15 shows Kaplan Meier plots for animals administered SAB-185 12 hours prior to or 6 hours after intranasal challenge with lethal doses of SARS-CoV-2. (A) mortality endpoints. (B) time to illness endpoint.

Three groups of five animals each were challenged with a lethal dose of SARS-CoV-2 intranasally and followed for 28 days, with daily observations including weight measurements and clinical signs of illness (Table 10). FIG. 15A shows a Kaplan Meier plot displaying the percent of mice surviving following challenge. In the control group, only one of five animals survived beyond day 9 post-challenge whereas all mice in the post-exposure and pre-exposure groups survived, demonstrating significant protection ($p<0.003$) against live SARS-CoV-2 challenge.

TABLE 10

| Clinical Observation | Score |
|---|---|
| Lethargy, ruffled fur, hunched appearance, slow movement, increased body, temp, or 10% weight loss | 1 |
| Decreased mobility, no longer socializing with other animals, or 20%, weight loss | 2 |
| Greatly labored respirations, gasping, inability to move even after stimulation or 25% weight loss | 3 |

Figure 15B:
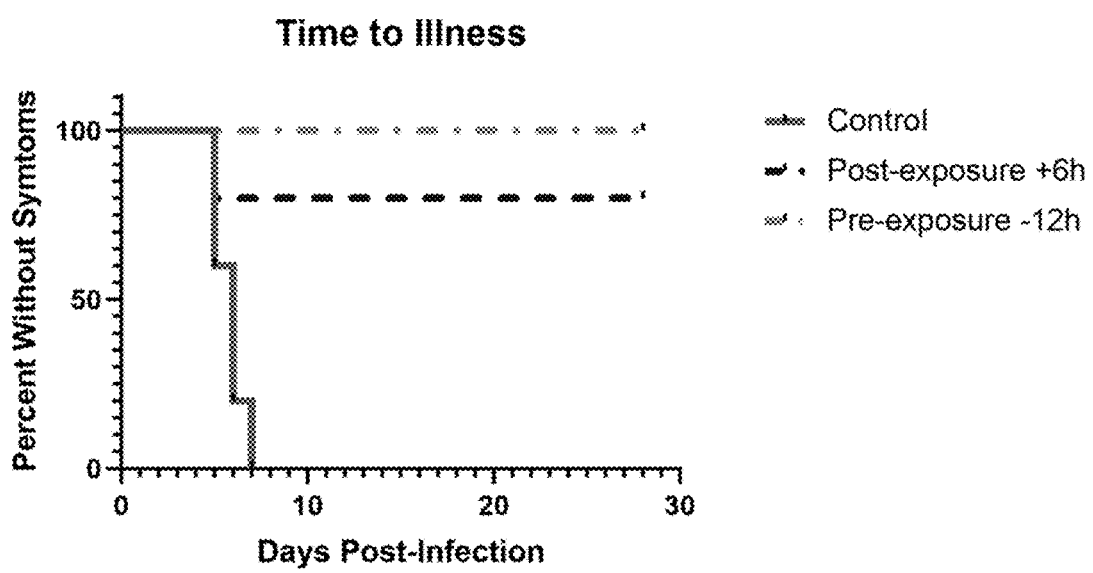

The time to the development of signs of infection is shown in FIG. 15B. By day 7, all five animals in the control group demonstrated one or more signs of infection. In the mice treated with high dose SAB-185 six hours post-challenge, all but one, which developed signs of disease on day 5 (and later recovered), remained symptom free. Mice given high dose IM SAB-185 12 hours prior to intranasal challenge remained symptom free throughout the observation period.

Discussion

The results of this study demonstrated that administering purified anti-SARS-CoV-2 hyperimmune polyclonal antibody product SAB-185 by IM injection provided significant protection against SARS-CoV-2 live virus challenge in K18 transgenic mice expressing the human ACE2 receptor. Low (1.88 mg) and high (3.75 mg) doses of SAB-185 polyclonal IgG antibody, when given pre-exposure 12 hours prior to intranasal challenge, significantly reduced SARS-CoV-2 infection of the lungs as evidenced by absence of or significantly reduced viral RNA detected by ddRT-PCR and by the inability to detect live virus by culture in lung tissue. Furthermore, histological examination and immunohistochemical staining of lung tissue demonstrated the absence of histopathology or infection in the lungs compared to untreated control mice.

Post-exposure animals subjected to high dose treatment with SAB-185 given IM six hours after intranasal SARS-CoV-2 challenge showed almost no lung pathology or infection as evidenced by the inability to recover live virus from the lungs of all 12 mice. High dose post-exposure treatment with SAB-185 administered 24 hours after challenge appeared to be less effective but still resulted in reduced SARS-CoV-2 viral RNA and a lower frequency of virus isolation from lung tissue compared to saline treated control mice. The trend for a greater reduction in viral load by administering SAB-185 six hours after challenge compared to 24 hours post-challenge may be explained by the earlier intervention to limit viral replication and systemic spread.

Human anti-SARS-CoV-2 IgG antibody was detected in pooled serum of mice given IM injections of SAB-185 before and after intranasal live virus challenge. The neutralizing activity of these antibodies was determined utilizing the cPASS assay. High levels of SARS-CoV-2 IgG and neutralizing antibodies in pooled serum samples demonstrated systemic dissemination of SAB-185 from the intramuscular injection site. In the pre-exposure groups, SARS-CoV-2 IgG and neutralizing antibody tended to be higher in the high dose group compared to the low dose group although the titers between groups at each time point were only within one dilution. For the post-exposure groups, both IgG and neutralizing antibody titers tended to be higher at days 2 and 4 in the mice dosed at six hours post-infection compared to those dosed at 24 hours but again the titers between groups were only within one dilution.

All mice demonstrated infection of the nasal turbinate following intranasal administration of live SARS-CoV-2. This was indicated by 2+ to 3+ histological changes upon examination of tissue samples by H&E and immunohistochemical staining. Without being bound by theory, the failure to prevent nasal turbinate infection was due to the lack of sufficient mucosal neutralizing antibody activity and the direct inoculation of high SARS-CoV-2 titers into the nasal passageway.

For mice in the untreated control group, except for one animal, evidence of SARS-CoV-2 infection was not observed in the brain, liver, kidney or heart by RT-PCR or viral culture. For the one animal, brain tissue showed evidence of infection by immunohistochemical staining at day 6 post-challenge. The detection of viral antigens in this lone animal indicates that CNS infection was an infrequent occurrence in our murine study. This contrasts the findings by Golden et al. *JCI Insight* 5(19):e142032 (2020) showing that most of the K18 transgenic mice in their study demonstrated evidence of brain involvement from 5-11 days post challenge.

In summary, IM SAB-185 administered pre- and post-SARS-CoV-2 challenge significantly reduced lung infection, morbidity and mortality in K18 mice compared to controls. This study provides preclinical evidence that IM SAB-185 could be an effective pre- and post-SARS-CoV-2 exposure treatment suitable to protect large populations such as medical and military personnel, immunosuppressed patients, critical infrastructure workers, and nursing home residents. These results support further clinical testing in humans to prevent COVID-19 disease.

Materials and Methods

Anti-SARS-CoV-2 Polyclonal Antibody SAB-185

SAB 185 was produced from transchromosomic cattle (Tc bovine) hyperimmunized in a prime-boost fashion with a DNA construct expressing full-length spike protein of the USA-WA1/2020 SARS-CoV-2 strain as the prime followed by boosts of recombinant ectodomain of spike protein. The prime consisted of two 12 mg doses of DNA formulated in SAB's proprietary adjuvant formulation (SAB-adj-1) given three weeks apart. The DNA vaccine was delivered by using the PharmaJet Stratis® IM injection device. The animals were subsequently boosted twice with 2 mg to 5 mg of recombinant ectodomain spike protein formulated in SAB-adj-1 at four week intervals. The cGMP lot of SAB-185 used in this experiment was pooled and purified from Tc bovine plasma obtained 8, 11 and 14 days after the second protein boost. The geometric mean 80% plaque reduction neutralization titer for this SAB-185 lot against a SARS-CoV-2 D614G strain was 4924. SARS-CoV-2 Challenge Virus The live USA-WA1/2020 strain of SARS-CoV-2 was propagated in VERO81 cells and harvested at passage 6 to prepare virus stocks for use in challenge experiments. The virus stocks were stored at a concentration of 2×105 PFU/mL (lethal challenge) and 2×104 PFU/mL (sub-lethal challenge) as determined by plaque assay. The stocks were maintained in storage at −80° C.

Prophylactic and Post-Exposure Intramuscular Administration of SAB-185

In the first experiment, five groups of K18-hACE2 transgenic mice (12 per group) were used. Groups 1 and 2 represented low and high dose pre-exposure treatment, respectively. The low dose consisted of 1.88 mg and the high dose 3.75 mg of SAB-185 in a total volume of 500 delivered IM 12 hours prior to intranasal challenge of SARS-CoV-2. Groups 3 and 4 represented post-exposure treatment and received high dose SAB-185 six hours and 24 hours, respectively, after intranasal SARS-CoV-2 live virus challenge. Animals in group 5 served as controls and received saline. All animals were infected intranasally with 103 PFU of SARS-CoV-2 in 50 µL on Day 0. On days 2, 4, 6 and 8, three animals from each group were euthanized and blood, lungs, nasal turbinate, brain, liver, kidney and heart removed at necropsy for histological examination. Portions of the lung were processed for the detection of live virus by culture and for detecting viral RNA by quantitative droplet digital RT-PCR (ddRT-PCR).

The second experiment examined the effectiveness of SAB-185 on reducing morbidity and mortality. Three groups of 5 animals each were challenged with lethal doses (1×104 pfu) of live SARS-CoV-2. Group 1 received high dose SAB-185 12 hours before challenge and group 2 received the same dose 6 hours after challenge. Animals in group 3 served as controls and received saline. Following intranasal challenge, the mice were observed for a total of 28 days for clinical symptoms of illness and mortality. Table 10 shows the symptom scale used to quantitate severity of clinical disease.

Pre- and Post-Exposure Efficacy Analysis of IM SAB-185

In the first experiment, lungs were harvested at the indicated times. Half of the organ was fixed in formalin and processed for histological examination. Histological grading of H&E sections of the tissues was performed based on the grading scale in Table 11. The other half was homogenized in PBS and half of the homogenate processed to evaluate viral load by ddRT-PCR analysis. The primer sequences targeted the nucleocapsid genes of the USA-WA1/2020 virus strain. The forward and reverse primer sequences were 5'-GACCCCAAAATCAGCGAAAT-3' (SEQ ID NO: 15) and 5'-TCTGGTTACTGCCAGTTGAATCTG-3' (SEQ ID NO: 16), respectively. The probe sequence used was 5'-ACCCCGCATTACGTTTGGTGGACC-3'-3IABkFQ (SEQ ID NO: 17). The ddRT-PCR results were expressed as total number of RNA copies. The results from SAB 185 treated animals were compared to the untreated controls to assess the effect of SAB 185 on viral burden post-live virus challenge.

TABLE 11

| Histology Description | Severity | Score |
|---|---|---|
| 10% or less Immunoreactive Cells | Minimal | 1+ |
| 11%-25% Immunoreactive Cells | Mild | 2+ |
| 26%-50% Immunoreactive Cells | Moderate | 3+ |
| 51%-79% Immunoreactive Cells | Marked | 4+ |
| 80% or more Immunoreactive Cells | Severe | 5+ |

The other half of the homogenate was processed for recovery of live virus by tissue culture. Briefly aliquots of the homogenate were incubated in flasks containing confluent monolayers of VERO81 cells and incubated for 7 days at 37° C. Following incubation, the cells were scraped, clarified by centrifugation at 3000 rpm, and the cell pellet resuspended and applied to 24-well slides for immunofluorescence assay (IFA). The slides were fixed in Cytofix/Cytoperm and then examined for the presence of fluorescent infected cells using antibodies directed at the spike protein of SARS-CoV-2 (ProSci, Cat. No. 3525).

Detection of SAB-185 Polyclonal Antibody in Mouse Serum

Total anti-SARS-CoV-2 IgG antibody was measured in mouse sera at the various time points using the COVID-SeroIndex quantitative assay. This assay detects human IgG and therefore was used to quantitate serum levels of SAB-185 following IM injection. The assay utilizes recombinant SARS-CoV-2 RBD antigen-coated plates that are reacted with mouse sera. Bound anti-RBD antibody is detected with an enzyme-linked anti-human IgG monoclonal antibody. For quantitation, positive samples are tested in a second orthogonal assay where plates coated with the SARS-CoV-2 spike protein are reacted with the sample, followed by bound antibody detection using the enzyme-linked anti-human IgG monoclonal antibody. The final quantitative readout of arbitrary units per milliliter (AU/mL) is calculated by comparing signal from the test samples to the calibration curve.

GeneScript cPASS technology was used to examine serum anti-SARS-CoV-2 neutralizing antibody activity in mice given SAB-185 by IM injection. This is an inhibition assay that detects total neutralizing antibodies in a specimen by mimicking the interaction between the SARS-CoV-2 virus and the host cell bearing the ACE-2 receptor protein.

Briefly, plates coated with the ACE-2 protein are reacted with a cocktail containing the serum specimen of interest and recombinant receptor binding protein conjugated with HRP. If antibodies are present in the specimen that binds to the RBD protein in such a way as to interfere with binding to the ACE-2 protein, there will be an absence of color, indicating the presence of neutralizing antibodies. Because the assay does not require direct detection of bound antibody, the assay can be used to detect both human and animal anti-SARS-CoV-2 antibodies and is not isotype specific. For this assay, sera from the three animals euthanized on the indicated days were pooled and tested. Two-fold serial dilutions were made of the pooled sera, which was subsequently tested in the cPASS inhibition assay for surrogate neutralization activity as per manufacturer guidelines. The highest serum dilution resulting in 80% or greater inhibition was considered the endpoint neutralization titer.

Data Analyses

Geometric mean RNA copy numbers for the indicated groups were calculated and compared for statistical significance by multiple means comparisons using one way ANOVA (Tukey Method). The results for the mortality and morbidity were analyzed by Log-rank (Mantel-Cox) test using the GraphPad Prism software package.

While embodiments of the present invention have been shown and described herein, those skilled in the art will understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed herein is:

1. A method of making polyclonal human immunoglobulin for treatment of coronavirus disease 2019 (COVID-19), comprising
   a) administering an antigen comprising a polynucleotide encoding a full-length Severe Acute Respiratory Syndrome related Coronavirus type 2 (SARS-CoV-2) spike (S) protein comprising an amino acid sequence of SEQ ID NO: 19 (GenRept: QHD43416), to a transgenic ungulate,
   wherein the transgenic ungulate is a bovine, comprising an artificial chromosome comprising a human heavy chain immunoglobulin (IgH) locus and a human immunoglobulin kappa (IgK) locus; and wherein a bovine immunoglobulin locus has been knocked out;
   b) administering an antigen comprising a SARS-CoV-2 S protein or an antigenic fragment thereof, to the transgenic ungulate;
   wherein the SARS-CoV-2 S protein comprises a deletion of a polybasic S1/S2 cleavage site (SEQ ID NO: 18) corresponding to residues 682 to 685 of SEQ ID NO: 19 (GenPept: QHD43416); amino acid substitutions of K986P and/or V987P relative to SEQ ID NO: 19 (GenPept: QHD43416), that stabilize an ectodomain of SARS-CoV-2 S protein; or a T4 foldon trimerization domain; and
   c) purifying a population of human immunoglobulins from serum or plasma of the transgenic ungulate after a) and b);
   wherein the population of fully human immunoglobulins comprises fully human immunoglobulin G (IgG);
   thereby making the polyclonal human immunoglobulin for treatment of COVID-19.

2. The method of claim 1, comprising administering the antigen comprising the SARS-CoV-2 S protein and/or the antigen comprising the polynucleotide two or more times.

3. The method of claim 1, wherein the antigen is administered in or co-administered with a pharmaceutical composition comprising Montanide ISA-206 and Quil A.

4. The method of claim 1, comprising:
   a) a first immunization comprising administering the polynucleotide encoding the full-length SARS-CoV-2 S protein on day 0 via intramuscular injection;
   b) a second immunization comprising administering the polynucleotide encoding the full-length SARS-CoV-2 S protein via intramuscular injection, about 21 to 28 days after step a);
   c) a third immunization comprising administering the SARS-CoV-2 S protein or an antigenic fragment thereof about 28 days after step b);
   d) a fourth immunization comprising administering the SARS-CoV-2 S protein or an antigenic fragment thereof, about 28 days after step c); and
   e) a fifth immunization comprising administering the SARS-CoV-2 S protein or an antigenic fragment thereof, about 28 days after step d).

5. The method of claim 1, wherein the population of human immunoglobulins comprises at least about 70% N-Glycolylneuraminic acid (NGNA)-bearing glycans.

6. The method of claim 5, wherein the NGNA-bearing glycans comprise at least 70% fucosylated glycans.

7. The method of claim 4, further comprising purifying the population of human immunoglobulins from serum or plasma of the transgenic ungulate after administering the third immunization, the fourth immunization and/or the fifth immunization.

8. The method of claim 7, comprising:
   a) purifying the population of human immunoglobulins from serum or plasma of the transgenic ungulate collected about 8 days after administering the third immunization;
   b) purifying the population of human immunoglobulins from serum or plasma of the transgenic ungulate collected about 11 days after the fourth immunization; and
   c) purifying the population of human immunoglobulins from serum or plasma of the transgenic ungulate collected about 14 days after administering the fifth immunization.

9. The method of claim 4, wherein the serum or plasma from the transgenic ungulate collected after the third immunization, the fourth immunization and/or the fifth immunization, is pooled.

* * * * *